United States Patent
Kubow et al.

(10) Patent No.: US 9,849,153 B2
(45) Date of Patent: *Dec. 26, 2017

(54) COMPOSITIONS AND METHODS FOR PREVENTING AND TREATING DISEASES AND ENVIRONMENTALLY INDUCED HEALTH DISORDERS

(71) Applicant: The Royal Institution For The Advancement of Learning/McGill University, Montreal (CA)

(72) Inventors: Stanley Kubow, Pointe Claire (CA); Danielle Donnelly, Baie d'Urfe (CA); Andre Piccolomini, Montreal (CA); Luis Agellon, Baie d'Urfe (CA)

(73) Assignee: The Royal Institution For The Advancement Of Learning/McGill University, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/235,384

(22) Filed: Aug. 12, 2016

(65) Prior Publication Data
US 2016/0346343 A1    Dec. 1, 2016

Related U.S. Application Data

(63) Continuation of application No. 14/267,719, filed on May 1, 2014, now Pat. No. 9,446,063, and a continuation-in-part of application No. 13/519,049, filed as application No. PCT/CA2010/002052 on Dec. 24, 2010, now abandoned.

(60) Provisional application No. 61/290,098, filed on Dec. 24, 2009.

(51) Int. Cl.
| | |
|---|---|
| *A61K 36/81* | (2006.01) |
| *A23L 33/105* | (2016.01) |
| *A23L 33/15* | (2016.01) |
| *A23L 33/10* | (2016.01) |
| *A61K 31/375* | (2006.01) |
| *A61K 31/192* | (2006.01) |
| *A61K 31/7048* | (2006.01) |
| *A61K 31/341* | (2006.01) |
| *A61K 31/353* | (2006.01) |
| *A61K 31/216* | (2006.01) |

(52) U.S. Cl.
CPC ............ *A61K 36/81* (2013.01); *A23L 33/10* (2016.08); *A23L 33/105* (2016.08); *A23L 33/15* (2016.08); *A61K 31/192* (2013.01); *A61K 31/216* (2013.01); *A61K 31/341* (2013.01); *A61K 31/353* (2013.01); *A61K 31/375* (2013.01); *A61K 31/7048* (2013.01); *A23V 2002/00* (2013.01)

(58) Field of Classification Search
CPC .... A61K 36/81; A61K 31/375; A61K 31/192; A61K 31/7048; A61K 31/341; A61K 31/353; A61K 31/216; A23L 33/105; A23L 33/15; A23L 33/10
See application file for complete search history.

(56) References Cited

FOREIGN PATENT DOCUMENTS

EP    1949792 A3    7/2008

OTHER PUBLICATIONS

Nassar et al., Am. J. Potato Res., 2014, 91, p. 89-100, Published online: Aug. 23, 2013.*
Stushnoff et al., Am. J. Potato Res., 2008, 85, p. 267-276.*
Rodriguez-Soana, L.E., Oregon State University thesis, 1999, 278 pages.*
Paynter et al., "Coffee and Sweetened Beverage Consumption and the Risk of Type 2 Diabetes Mellitus"; Am J Epidemiol (2006) 164:1075-1084 (10 pages).
Morton et al., "Chemistry and Biological Effects of Dietary Phenolic Compounds: Relevance to Cardiovascular Disease"; Clin Exp Pharmacol Physiol (2000) 27:152-59 (8 pages).
Sotillo et al., "Chlorogenic Acid Modifies Plasma and Liver Concentrations of: Cholesterol, Triacylglycerol, and Minerals in (fa/fa) Zucker Rats"; Nutritional Biochem (2002) 13:717-726 (10 pages).
Johnston et al., "Coffee Acutely Modifies Gastrointestinal Hormone Secretion and Glucose Tolerance in Humans: Glycemic Effects of Chlorogenic Acid and Caffeine"; Am J Clin Nutr (2003) 78:728 (6 pages).
Srinivasan et al., "Ferulic Acid: Therapeutic Potential Through Its Antioxidant Property"; J Clin Biochem Nutr. (2007) 10: 92-100 (9 pages).
Selloum et al., "Anti-Inflammatory Effect of Rutin on Rat Paw Oedema, and on Neutrophils Chemotaxis and Degranulation"; Experim Tox Path (2003) 54:313-318 (6 pages).
Umamaheswari, et al., "Antihyperglycaemic Effect of 'Ilogen-Excel', an Ayurvedic Herbal Formulation in Streptozotocin-Induced Diabetes Mellitus"; PSM 2007 Acta Pol Pharma 64:53-61 (9 pages).
Piccolomini, et al, "Unraveling the Chlorogenic Acid and Phenolic Content Among 12 Potato Cultivars for Improved Human Health and Consumer Acceptance"; Hortscience, American Society of Horticultural Science, Alexandria, VA, US, vol. 43, No. 4, Jul. 1, 2008, p. 1222, Abstract (1 pages).
Piccolomini, et al, "Differential Antioxidant Capacity Among 12 Potato Cultivars"; Hortscience, American Society of Horticultural Science, Alexandria, VA, US, vol. 43, No. 4, Jul. 1, 2008, p. 1082, Abstract (1 page).
Database WPI Week 200962, Thomson Scientific, London, GB; AN 2009-L11818 XP002723160 & KR 100 904 859 B1 (Knu Ind Coop Found) Jun. 25, 2009 (1 page).

(Continued)

*Primary Examiner* — Jonathan S Lau
(74) *Attorney, Agent, or Firm* — Hovey Williams LLP

(57) ABSTRACT

Nutraceutical or pharmaceutical compositions, functional foods, extracts, dietary supplements and food/feed additives enriched in phytochemicals having antioxidant and/or anti-inflammatory activity may be derived from the skin, pith, or cortex from stem tubers of select potato cultivars, such as Onaway, Russet Burbank, Purple Valley or Bora Valley cultivars. These cultivars and combinations thereof provide a useful antioxidant source enriched in ferulic acid, caffeic acid, chlorogenic acids, ascorbic acid, anthocyanins, and rutin, isomers or derivatives thereof having antioxidant and/or anti-inflammatory activity.

11 Claims, 13 Drawing Sheets

(56) References Cited

OTHER PUBLICATIONS

Database WPI Week 200676, Thomson Scientific, London, GB; AN 2006-737328 XP002723161 & KR 2005 0110186 A (Potato Valley Inc.) Nov. 23, 2005 (1 page).

Tudela et al., "Induction of Antioxidant Flavonol Biosynthesis in Fresh-Cut Potatoes. Effect of Domestic Cooking", Journal of Agricultural and Food Chemistry, vol. 50, No. 21, Oct. 1, 2002, pp. 5925-5931 (7 pages).

Keller, et al., "Changes in the Accumulation of Soluble and Cell Wall-Bound Phenolics in Elicitor-Treated Cell Suspension Cultures and Fungus-Infected Leaves of Solanum Tuberosum", Phytochemistry, vol. 42, No. 2, May 1, 1996, pp. 389-396 (8 pages).

Supplementary European Search Report in corresponding EP 10 83 8476, dated Apr. 10, 2014 (3 pages).

Wheeler et al., The Onaway Potato, An Early Variety, American Potato Journal, 1961, vol. 38, No. 10, pp. 353-355.

Brown et al., "Antioxidants in Potato," Amer. J. of Potato Res., 2005, vol. 82, pp. 163-172.

* cited by examiner

COMPOSITIONS AND METHODS FOR PREVENTING AND TREATING DISEASES AND ENVIRONMENTALLY INDUCED HEALTH DISORDERS

CROSS-REFERENCE TO RELATED APPLICATIONS

This application is a continuation of U.S. Ser. No. 14/267,719, filed May 1, 2014, incorporated by reference herein, which is a continuation-in-part of U.S. Ser. No. 13/519,049, which is the National Stage of International Application No. PCT/CA2010/002052, filed Dec. 24, 2010, which claims the priority benefit of U.S. Provisional Patent Application Ser. No. 61/290,098, filed Dec. 24, 2009.

FIELD OF INVENTION

The present invention relates to compositions and methods for preventing and treating diseases related to metabolic and stress-related disorders and environmentally induced health disorders. More specifically, the invention relates to compositions enriched in phytochemicals having antioxidant and/or anti-inflammatory activity derived from the skin, pith, or cortex or a combination thereof from select cultivars of potato (*Solanum* spp.).

BACKGROUND OF THE INVENTION

Antioxidants have been studied extensively to identify how they influence human health. They include phytochemicals, vitamins, and other nutrients that protect cells from damage caused by free radicals. They can be found in fruits and vegetables as well as culinary and medicinal herbs.

Oxidative stress is associated with the pathogenesis of a variety of diseases. As a result, antioxidants have been used to combat or minimize the damaging effects of those diseases on the body.

For instance, chlorogenic acid and caffeic acid are two antioxidants implicated in the prevention of type-2 diabetes mellitus (T2DM; Paynter et al., Am J Epidemiol (2006) 164:1075-1084) and in cardiovascular disease (Morton et al., Clin Exp Pharmacol Physiol (2000) 27:152-59). Ingestion of chlorogenic acid improves glucose tolerance in obese Zucker rats resulting in diminished postprandial blood glucose concentrations (Sotillo and Hadley, Nutritional Biochem (2002) 13:717-726) with similar effects indicated in human trials (Johnston et al., Am J Clin Nutr (2003) 78:728). Marketed under the trade name Svetol™, chlorogenic acid has also been approved in Norway and the United Kingdom as a food active ingredient used in coffee, chewing gum, and mints to promote weight reduction.

Ferulic acid, a flavonoid, is another antioxidant having a wide range of therapeutic effects, including anti-inflammatory, anti-atherogenic, anti-diabetic, anti-ageing, neuroprotective, radioprotective and hepatoprotective properties (Srinivasan et al., J Clin Biochem Nutr. (2007) 40: 92-100). Ferulic acid is often added as ingredient of herbal supplements.

Rutin, a citrus flavonoid glycoside found in a variety of fruits and vegetables including asparagus, citrus fruits, and berries, is used in medications for blood vessel protection and as an ingredient in multivitamin preparations and herbal remedies. It has been shown to have anti-inflammatory properties (Selloum et al., Experim Tox Path (2003) 54:313-318), and is a known anti-oxidant.

While plants, vegetables, and fruits are common sources, there are very few that are naturally antioxidant-rich. Thus, a tremendous effort has been deployed in the past several years to find sources of antioxidants that produce a health effect.

One approach to this problem has been to increase antioxidant levels in crops through genetic modification. WO2008/005474 (High level antioxidant-containing foods. Publication Date Jan. 10, 2008 Rommens, C.; PCT/US2007/015437) describes methods of genetically modifying Solanaceous crops, including potato, tobacco, tomato, *capsicum*, and eggplant by inserting a chlorogenic acid-inducing gene (Cai). Despite the scientific merit, genetically modified (GM) plants pose risks to non-transformed food chain crops and regulatory approval must be obtained before widespread use.

Methods of extracting antioxidants from different plants have also been developed to produce nutraceuticals and food additives with health benefits. As an example, EP1949792 (The healthy and functional foods for the obesity patients using purple-colored potatoes. Publication Date Jul. 11, 2007 Lim, H. K et al.; 07013597.5) describes functional foods and food additives with obesity-suppressing activity that are manufactured using an aqueous extract of the purple potato *Solanum tuberosum* L. cv. Bora Valley.

JP2007119346 describes conjugates of quinic acid and caffeic acid derived from the leaves and stems of sweet potatoes (*Ipomoea* spp.) that have anti-diabetic properties. WO2006/014028 (International Application No.: PCT/JP2005/014799. Suzuki, S.; Kitani, S.; Yasutani, I.; Sweet potato stem extract and use thereof Publication Date: Feb. 9, 2006, International Filing Date: Aug. 5, 2005) also describes extracts from the stalk and leaves of sweet potato enriched in polyphenol, and which are useful for preventing and treating obesity. JP2006230225 describes food additives for suppressing increases in blood glucose levels, including triterpene derivatives, hydrolysis-type tannins, ellagic acid or chlorogenic acid, and which are derived from plants of the genus *Gymnema*, guava leaves, plants of the genus *Turminalia*, or sugarcane. Compositions comprising caffeine and chlorogenic acid have even been used in cosmetics with slimming properties (FR2883472) (Milesi et al.; FR20050002886 20050323).

Obesity and type 2 diabetes mellitus have become a significant public health issue. It has been suggested that certain plant metabolites can prevent and treat obesity and diabetes via modulation of cellular signaling pathways. Said plant metabolites, ingested as typical dietary components, are considered as relatively safer alternatives to drug-based therapeutics for obesity, insulin resistance and type 2 diabetes mellitus (Liu et al 2010, Biochim. Biophys. Acta 2010, 1799, 854-865; Shehzad et al., 2011, Eur. J. Nutr. 50, 151-161). As the chemopreventive activity of fruits and vegetables are mainly associated with their phenolic compounds, studies determined the bioactivity of specific polyphenolic compounds (Hanhineva et al 2010, Int. J. Mol. Sci. 11, 1365-1402). Polyphenols were suggested to exert their hypoglycemic properties partly by inhibiting digestive enzymes (Bravo, 1998, Nutr. Rev., 56, 317-3330) and lowered the glycemic index inversely correlated with their intake (Thompson et al., 1984, Am. J. Clin. Nutr. 1984, 39, 745-751).

However, the complexity of phytochemical mixtures in fruits and vegetables could exert additive and/or synergistic effects to provide enhanced health benefits on a variety of physiological and biochemical levels including hormone metabolism, immune system functioning, and gene expression profiles. Plant and vegetable extracts have been shown to possess anti-hyperglycemic properties in animal models of diabetes, such as in mulberry (Andallu and Varadacharyulu 2003, Clin. Chim. Acta, 338, 3-10), Aegle marmelos (Kamalakkannan and Prince, 2003, J. Ethnopharmacol., 87, 207-210), and chard (Bolkent et al., 2000, J. Ethnopharmacol., 73, 251-259).

Potatoes are an excellent source of phenolic compounds Camire et al 2009, Crit. Rev. Food Sci. Nutr., 49, 823-840) that have been linked with glucose-lowering effects in animal feeding trials using potato peel powder (Singh et al., 2005, Plant Foods Hum. Nutr. 60, 49-54). Mild suppression of body weight gain and inhibition of abdominal fat accumulation had been noted in high fat-fed rats supplemented with anthocyanin-rich purple fleshed potato ethanolic extracts (Yoon et al., 2008, J. Ethnopharmacol., 118, 396-404). Feeding pure chlorogenic acid or ferulic acid has been reported to have anti-obesity and hypoglycemic activity in animals (Cho et al., Food Chem. Toxicol. (2010) 48, 937-943; Jin Son et al., J. Clin. Biochem. Nutr. (2010) 46, 150-156, Tunnicliffe, et al., Appl. Physiol. Nutr. Metab. (2011) 36, 650-659; Ohnishi et al.; Biofactors (2004) 21, 315-319. and Shimoda et al., Altern. Med. 2006, 6, 9.

Despite these advances, researchers continue to pursue new ways of deriving health benefits from naturally occurring antioxidants, and to investigate the minimally essential components for a nutraceutical composition to reproducibly show health effects in obesity and type 2 diabetes.

SUMMARY OF THE INVENTION

An object of the invention is accordingly to provide improved compositions and sources of antioxidants and phytochemicals, which provide health benefits and/or improve over those known in the art.

The present invention, accordingly, relates to a composition enriched in chlorogenic acids, including but not limited to chlorogenic, cryptochlorogenic and neochlorogenic acids, ferulic acid, caffeic acid, anthocyanins, ascorbic acid, and the flavonoid rutin, or an isomer or derivative thereof having antioxidant and/or anti-inflammatory activity, wherein said chlorogenic acids and said ferulic acid are in a proportion ranging between 25:1 and 35:1 by weight respectively. The composition may comprise at least one potato cultivar, or an extract or fraction thereof. In certain embodiments, the composition may comprise an extract or fraction of an Onaway, Purple Valley or Bora Valley cultivar, or combinations thereof, and may optionally also be supplemented with a Russet Burbank cultivar. In yet a further non-limiting embodiment, the composition comprises a combination of extracts or fractions of the Onaway cultivar complemented by a Russet Burbank potato cultivar, and optionally one or more of a Purple Valley or Bora Valley cultivar. In other non-limiting embodiments, the extract or fraction is derived from the potato skin, pith, or cortex, or a combination thereof.

In an embodiment, the composition may be prepared as an oral supplement, a functional food, or a food/feed additive. In further embodiments, the composition may be an extract or fraction of the specified potato cultivars, and may optionally be formulated as a pharmaceutical or nutraceutical composition further comprising one or more acceptable carrier or excipient.

The present invention also relates to a commercial package comprising a food enriched in ferulic acid, caffeic acid, chlorogenic acids, ascorbic acid, anthocyanins, and rutin, or an isomer or derivative thereof having antioxidant and/or anti-inflammatory activity. The commercial package may comprise a food or feed enriched with an extract or fraction of at least one potato cultivar, wherein the chlorogenic acids and ferulic acid are in a proportion ranging between 25:1 and 35:1 by weight respectively. In certain embodiments, the food or feed in the commercial package may be supplemented with an extract or fraction of an Onaway, Purple Valley or Bora Valley cultivar, or combinations thereof, and optionally also supplemented with an extract or fraction of a Russet Burbank cultivar. In yet a further non-limiting embodiment, the commercial package may comprise a food or feed enriched with a combination of extracts or fractions from the Onaway and Russet Burbank potato cultivars, and optionally one or more of either the Purple Valley or Bora Valley cultivars.

In addition, the invention relates to a functional food enriched in ferulic acid, caffeic acid, chlorogenic acids, ascorbic acid, anthocyanins, and rutin, or an isomer or derivative thereof having antioxidant and/or anti-inflammatory activity. The functional food is supplemented with an extract or fraction of at least one potato cultivar. In certain embodiments, the functional food may be supplemented with an Onaway, Purple Valley or Bora Valley cultivar, or combinations thereof, and optionally also supplemented with an extract or fraction of a Russet Burbank cultivar. In yet a further non-limiting embodiment, the functional food may be supplemented with a combination of extracts or fractions from the Onaway and Russet Burbank potato cultivars, and optionally one or more of a Purple Valley or Bora Valley cultivar.

The invention further relates to optimization of phytochemical content in the selected cultivars via cold storage conditions, cultivation location and pre- or post-harvest hormetic treatments (such as but not limited to UV exposure or application of any oxidizing agent such as ozone, hydrogen peroxide, etc.). Thus, phytochemical content can in non-limiting embodiments be optimized by treating the source of the potato cultivar or extract or fraction thereof to induce hormesis, and thereby increase the level of one or more of ferulic acid, caffeic acid, chlorogenic acids, anthocyanins, ascorbic acid, rutin, or isomers or derivatives thereof having antioxidant and/or anti-inflammatory activity in the source of the potato cultivar or extract or fraction thereof. The treatment to induce hormesis can be administered before or after harvesting, or during the storage interval of the source of the potato cultivar or extract or fraction thereof, or combinations thereof. In specific embodiments, which are not considered to be limiting in any way, the treatment to induce hormesis can include: treatment with relatively high (e.g. greater than about 40° C., including about 40, 41, 42, 43, 44, 45, 50° C. or higher) or low (e.g. less than about 5° C., including about 5, 4, 3, 2° C. or lower) temperature air or water; treatment with an excess of one or more minerals; partial to severe starvation of one or more minerals; treatment with ionizing radiation (including but not limited to UV-C rays, x-rays, gamma-rays, microwaves, natural or artificial light at high flux density, electron beam irradiation and other radiation sources), treatment with one or more oxidizing agents (including but not limited to peroxide ($H_2O_2$), ozone or other oxidizing agents); wounding (including but not limited to mechanical, biotic or a combination thereof); or treatment with one or more phytochemicals (including but not limited to ethylene, methyl jasmonate, jasmonic acid, absicisic acid, phosphatidic acid or salicylic acid).

In other non-limiting embodiments, phytochemical content can be optimized by shortening the storage interval of the potato source, or otherwise using a fresh source of the potato cultivar or extract or fraction thereof. In certain embodiments the source of the potato cultivar or extract or fraction thereof is obtained within 7 months post-harvest, including within 1, 2, 3, 4, 5, 6 or about 7 months post-harvest including intervening time intervals. In other preferred embodiments, the source of the potato cultivar or extract or fraction thereof is obtained within 2 months post-harvest, or more preferably, within 1 month post-harvest.

In addition, the invention relates to the demonstration of minimal inter-seasonal differences for the identified cultivars to be selected for phytochemical extraction (i.e., Onaway, Bora Valley, and Purple Valley). Other cultivars, such as Goldrush, show large inter-seasonal differences that are therefore not amenable for routine cultivation for phytochemical content.

The invention further relates to a method of treatment. For instance, in a non-limiting embodiment there is provided a method of treating or preventing an oxidative stress-related disease or disorder comprising administering a composition as described herein to a subject in need thereof in an amount sufficient to ameliorate or prevent said oxidative stress-related disease or disorder.

In another non-limiting embodiment there is provided a method of treating or preventing a chronic inflammatory disease or disorder that includes but is not limited to diabetes (type-1 and/or -2), cardiovascular complications including atherosclerosis, plaque formation, ischemia, blood clots, congestive heart failure, heart attacks and strokes, hypertension, liver diseases, respiratory disorders such as asthma, emphysema, bronchitis, chronic obstructive lung disease, and other lung diseases, and comprising administering a composition as described herein to a subject in need thereof in an amount sufficient to ameliorate or prevent said chronic inflammatory disease or disorder. In certain embodiments, the chronic inflammatory disease or disorder may be inflammatory bowel disease.

In yet another non-limiting embodiment, there is provided a method of improving insulin sensitivity and/or glucose tolerance comprising administering a composition as described herein to a subject in need thereof in an amount sufficient to improve insulin sensitivity and/or glucose tolerance in said subject.

There is also provided, in a non-limiting embodiment, a method of improving blood lipids and/or reducing adiposity comprising administering a composition as described herein to a subject in need thereof in an amount sufficient to improve blood lipids and/or reduce adiposity in said subject.

Further provided, in a non-limiting embodiment, is a method of treating or preventing diabetes (type-1 and/or -2) and/or obesity comprising administering a composition as described herein to a subject in need thereof in an amount sufficient to ameliorate or prevent the diabetes (type-1 and/or -2) and/or obesity in said subject.

The invention also relates, in a non-limiting embodiment, to a method of treating or preventing hyperlipidemia comprising administering a composition as described herein to a subject in need thereof in an amount sufficient to ameliorate or prevent the hyperlipidemia in said subject.

Also provided is a non-limiting method of treating or preventing epithelial cell type cancers including but not limited to skin, lung, liver, stomach, ovarian, and colon comprising administering a composition as described herein to a subject in need thereof in an amount sufficient to ameliorate or prevent the cancer in said subject.

The invention further provides, in a non-limiting embodiment, a method of treating a chronic inflammatory disease that is aggravated by particulate, such as but not limited to ultrafine particles and gaseous environmental air and waste pollution, comprising administering a composition as described herein to a subject in need thereof in an amount sufficient to ameliorate said chronic inflammatory disease in said subject. In such an embodiment, the chronic inflammatory disease that is aggravated by particulate and/or pollution may include, without limitation, respiratory disorders such as asthma emphysema, bronchitis, chronic obstructive lung disease, and other lung diseases.

The invention further relates to a process for preparing a composition enriched in ferulic acid, caffeic acid, chlorogenic acids, ascorbic acid, rutin, anthocyanins, or an isomer or derivative thereof having antioxidant and/or anti-inflammatory activity, the process comprising: (i) obtaining a source of at least one potato cultivar, such as an Onaway, Purple Valley or Bora Valley potato cultivar, and optionally complemented with another cultivar such as Russet Burbank, (ii) extracting or fractionating the at least one potato cultivar, and (iii) formulating the extracted or fractionated material into the composition enriched in ferulic acid, caffeic acid, chlorogenic acids, ascorbic acid, rutin, and anthocyanins or derivatives thereof, wherein the chlorogenic acids and ferulic acid are in a proportion ranging between 25:1 and 35:1 by weight respectively.

In certain non-limiting embodiments, the extracting step may comprise one or more liquid extraction steps with a solvent. The solvent may comprise acids (including but not limited to acetic acid, metaphosphoric acid, potassium metabisulphite), and/or alcohols (including but not limited to water, methanol (MeOH), ethanol (EtOH), isopropanol, or combinations thereof). The solvent may comprise, without limitation, from about 5 to about 100% MeOH, from 0 to about 10% metaphosphoric acid, and from 0 to about 10 mM EDTA, preferably about 50% MeOH, about 2.5% metaphosphoric acid, and about 1 mM EDTA.

In further non-limiting embodiments, the extracting step may comprise steps of mixing followed by separation. The process may also include, without limitation, a step of concentrating supernatant fractions obtained during the fractionating. The concentrating step may be carried out using lyophilization (freeze-drying), spray-drying, or evaporating processes, or other non-limiting concentrating process. Further, the process may also include one or more chromatographic separation steps, for instance using high-pressure liquid chromatography (HPLC) but not limited thereto.

Those skilled in the art will recognize, or be able to ascertain using no more than routine experimentation, numerous equivalents to the specific procedures described herein. Such equivalents are considered to be within the scope of this invention and are covered by the following claims.

BRIEF DESCRIPTION OF THE DRAWINGS

These and other features of the invention will become more apparent from the following description in which reference is made to the appended drawings wherein.

DETAILED DESCRIPTION

Figure 1:
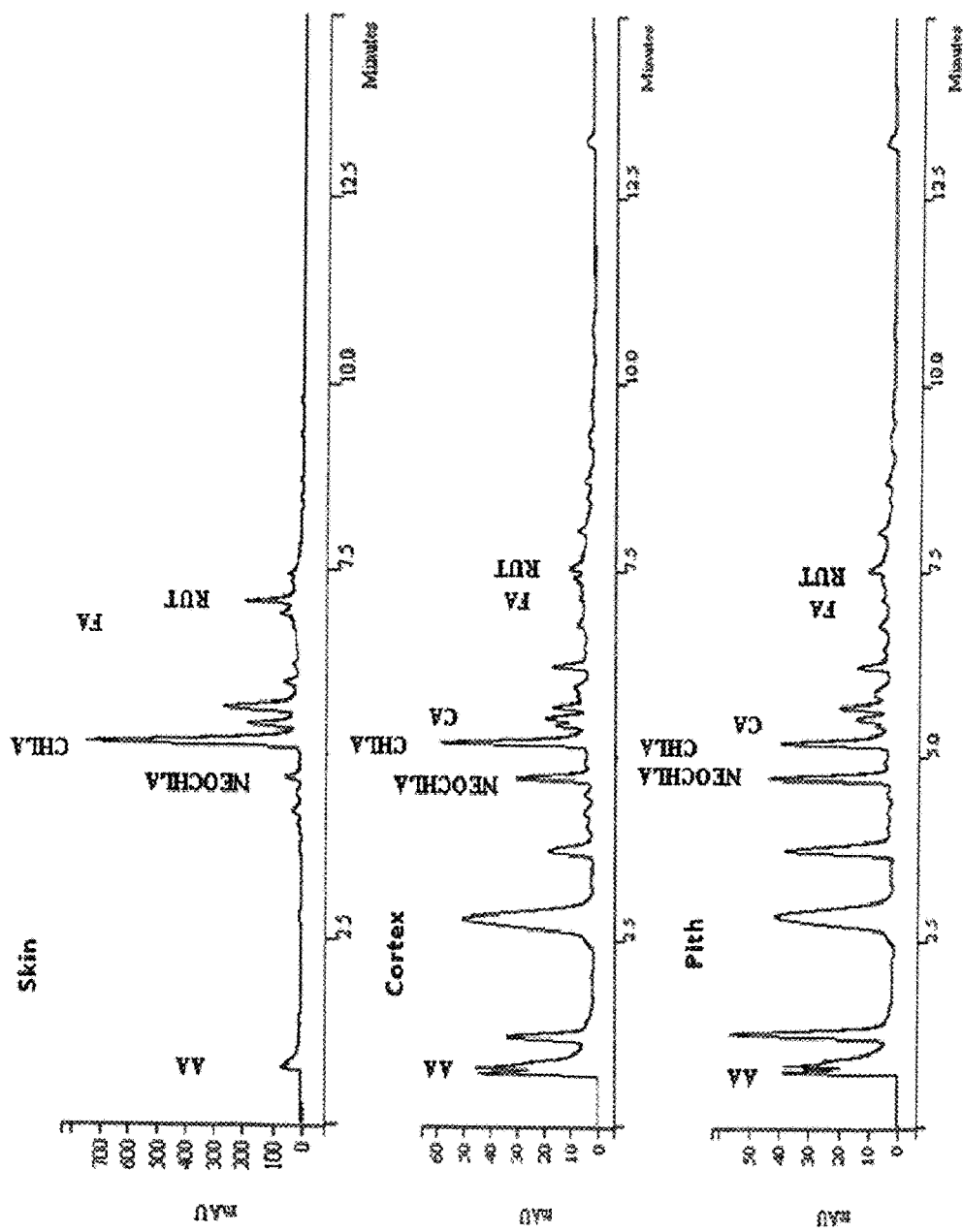
FIG. 1 shows HPLC chromatograms of the phytochemical profile of skin, cortex, and pith sections of stem tubers from Onaway potato cultivar. Analysis was conducted using Onyx (Phenomenex) a monolithic column. Separation was achieved using gradient elution of buffer A (10 mM formic acid, pH 3.5, with NH4OH) and buffer B (100% methanol with 5 mM ammonium formate). Gradient conditions were 0-1 min 100% (buffer A), 1-5 min 0-30% (buffer B), 5-6.5 min 40-70% buffer B, 6.5-8.5 min 70-100% buffer B. UV detection was at 280 nm. Solvent flow rate was 2 mL/min. AA=ascorbic acid, NEOCHLA=neochlorogenic acid, CHLA=chlorogenic acid, CA=caffeic acid, FA=ferulic acid, RUT=rutin.
Figure 2:
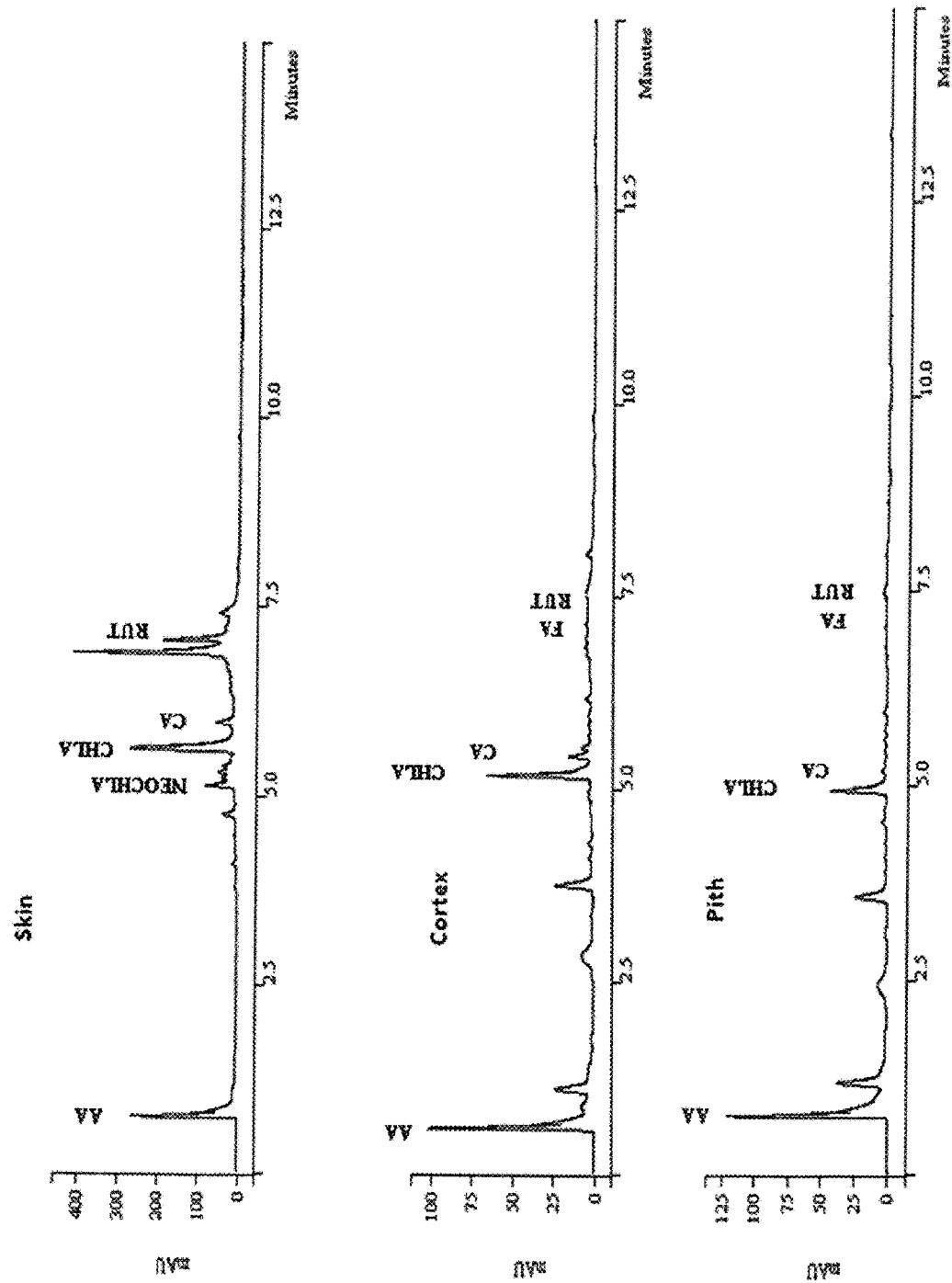
FIG. 2 shows HPLC chromatograms of the phytochemical profile of skin, cortex and pith sections of stem tubers from Russet Burbank potato cultivar. Analysis was conducted using Onyx (Phenomenex) a monolithic column. Separation was achieved using gradient elution of buffer A (10 mM formic acid, pH 3.5, with NH4OH) and buffer B (100% methanol with 5 mM ammonium formate). Gradient conditions were 0-1 min 100% (buffer A), 1-5 min 0-30% (buffer B), 5-6.5 min 40-70% buffer B, 6.5-8.5 min 70-100% buffer B. UV detection was at 280 nm. Solvent flow rate was 2 mL/min. AA=ascorbic acid, NEOCHLA=neochlorogenic acid, CHLA=chlorogenic acid, CA=caffeic acid, FA=ferulic acid, RUT=rutin.
Figure 3:
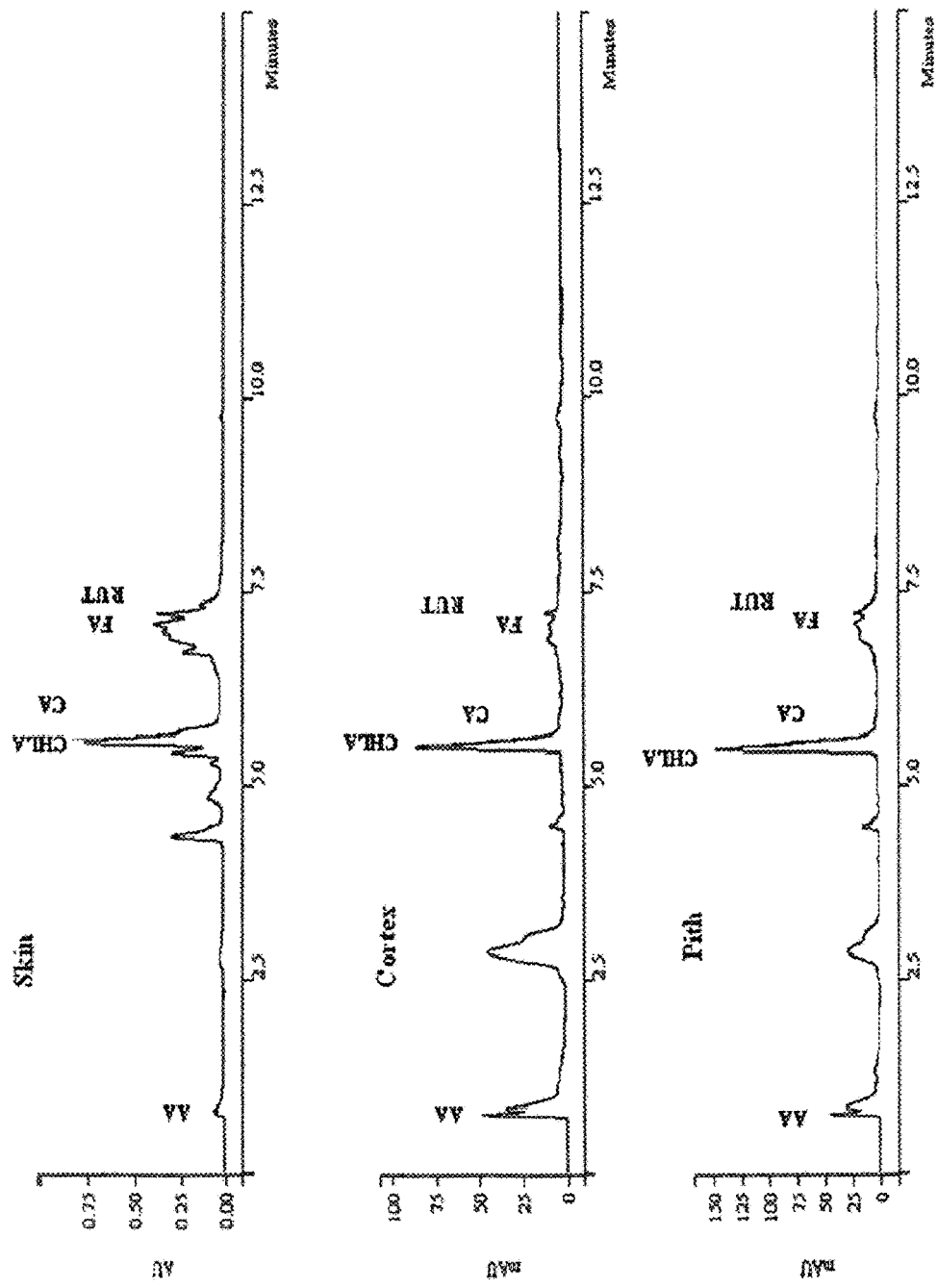
FIG. 3 shows HPLC chromatograms of skin, cortex and pith sections of stem tubers from Purple Valley potato cultivar. Analysis was conducted using Onyx (Phenomenex) a monolithic column. Separation was achieved using gradient elution of buffer A (10 mM formic acid, pH 3.5, with $NH_4OH$) and buffer B (100% methanol with 5 mM ammonium formate). Gradient conditions were 0-1 min 100% (buffer A), 1-5 min 0-30% (buffer B), 5-6.5 min 40-70% buffer B, 6.5-8.5 min 70-100% buffer B. UV detection was at 280 nm. Solvent flow rate was 2 mL/min. AA=ascorbic acid, NEOCHLA=neochlorogenic acid, CHLA=chlorogenic acid, CA=caffeic acid, FA=ferulic acid, RUT=rutin.
Figure 4:
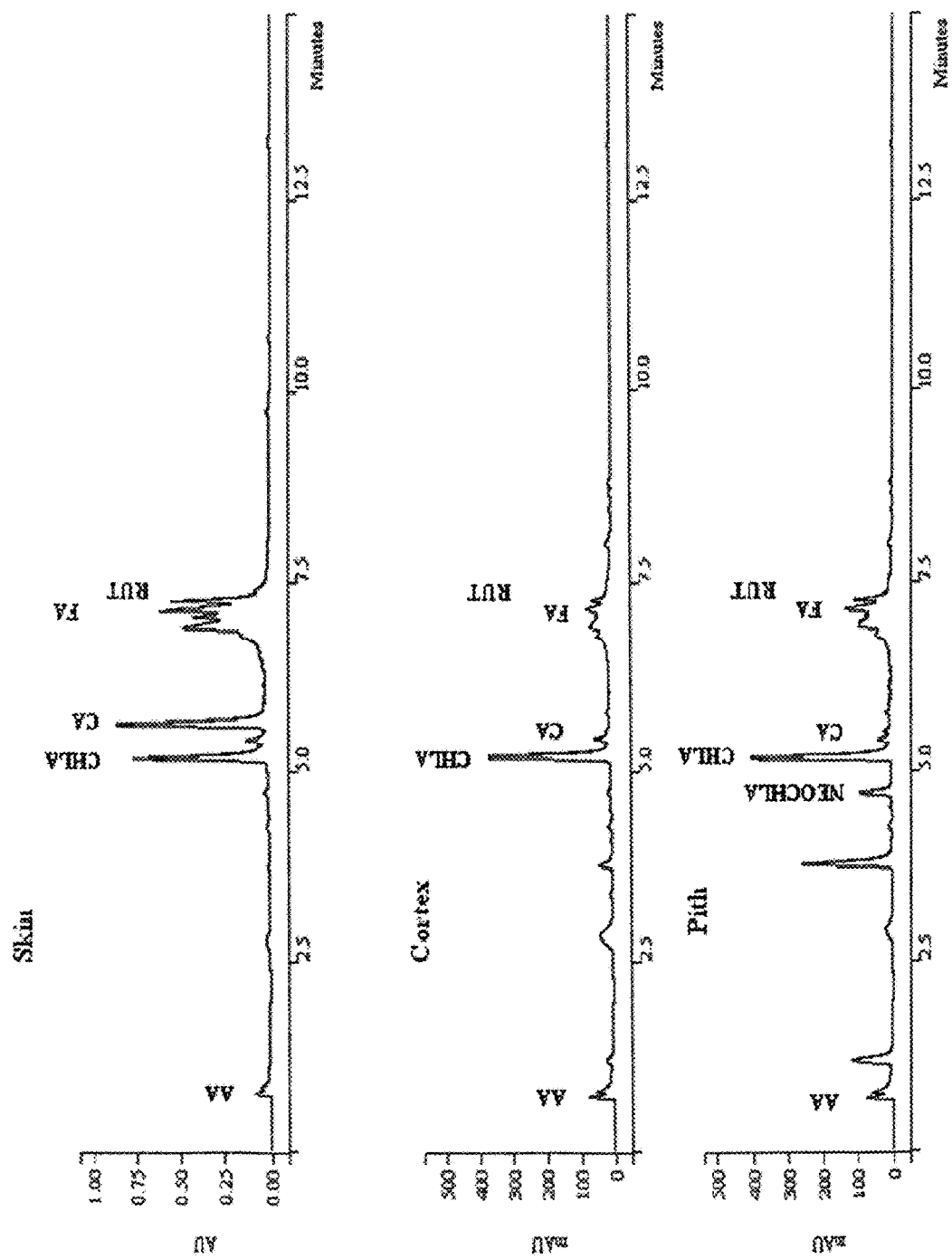
FIG. 4 shows HPLC chromatograms of skin, cortex and pith sections of field-grown Bora Valley potato cultivar. Analysis was conducted using Onyx (Phenomenex) a monolithic column. Separation was achieved using gradient elution of buffer A (10 mM formic acid, pH 3.5, with NH40H) and buffer B (100% methanol with 5 mM ammonium formate). Gradient conditions were 0-1 min 100% (buffer A), 1-5 min 0-30% (buffer B), 5-6.5 min 40-70% buffer B, 6.5-8.5 min 70-100% buffer B. UV detection was at 280 nm. Solvent flow rate was 2 mL/min. AA=ascorbic acid, NEOCHLA=neochlorogenic acid, CHLA=chlorogenic acid, CA=caffeic acid, FA=ferulic acid, RUT=rutin.

In order to combine the positive health effects of three important phenolic antioxidants, i.e., chlorogenic, ferulic, and caffeic acids, the antioxidant bioflavonoid rutin, and the antioxidant vitamin ascorbic acid, as well as anthocyanins, the present inventors have developed a naturally enriched source of these chemicals which is useful as, without being limited to, functional foods or drinks, a food additive, a food ingredient, a supplement, a pharmaceutical composition, and/or a nutraceutical composition.

In particular, the inventors have found that unexpectedly high concurrent levels of these four phytochemicals together with ascorbic acid and anthocyanins can be obtained in potatoes. This is particularly observed in the Onaway potato cultivar, although there are various embodiments that are envisioned including, e.g. Onaway, optionally complemented by Russet Burbank potato cultivar, and/or other cultivars such as the Purple Valley and Bora Valley potato cultivars. Such a combination can be used in a variety of ways to obtain health benefits due to the antioxidant and anti-inflammatory properties of these phytochemicals. Such a combination is, in certain embodiments, optimized to provide a standardized potato extract with the phytochemicals chlorogenic acid (CGA) and ferulic acid (FA) in a proportion ranging between 25:1 and 35:1 by weight.

In certain non-limiting embodiments, an Onaway potato cultivar, and in further embodiments a combination of Onaway optionally complemented by Russet Burbank potato cultivar, or other embodiments comprising one or more of the Purple Valley or Bora Valley potato cultivars, can be provided as an oral supplement, a functional food, or a food/feed additive. In other non-limiting embodiments, extracts of these potato cultivars or combinations thereof can be prepared. In further embodiments, such extracts will be adjusted to contain CGA and FA in a proportion ranging between 25:1 and 35:1 by weight. Such extracts can be used as a supplement or a food/feed additive, or can be formulated with known carriers or excipients to provide a pharmaceutical or nutraceutical composition. For example, the supplement or food/feed additive may be formulated or combined with the extract in such a way as to enrich the supplement or food/feed additive with between 25:1 and 35:1 by weight of CGA and FA. For instance, the food/feed may comprise from 150 to 210 mg of CGA/kg of feed, for every 1 mg of FA/kg of feed. It is also envisioned that, in further non-limiting embodiments, commercial food packages can be prepared comprising an extract or fraction of at least one potato cultivar, such as an Onaway, Purple Valley or Bora Valley potato cultivar or combination thereof, optionally complemented by a Russet Burbank potato cultivar.

In further non-limiting embodiments, the extract or fraction of a potato cultivar or combination of potato cultivars rich in phenolic phytochemicals will be prepared and/or adjusted such that the phenolic acids cholinergic acid and ferulic acid are contained or combined in a proportion ranging between 25:1 and 35:1 by weight, including proportions within this range such as 26:1, 27:1, 28:1, 29:1, 30:1, 31:1, 32:1, 33:1, 34:1 and intermediate proportions therebetween. The extracts or fractions adjusted in this way can be provided as an oral supplement, a functional food, or a food/feed additive.

The combined therapy of phytochemical extracts has been shown to be more effective than treatment involving individual phytochemicals in animal diabetic models (Umamaheswari and Prince, Acta Pol Pharm (2007) 64:53-61). Thus, it is believed that the compositions and combinations described herein, which provide a natural combination of phytochemicals, will provide safer and better health benefits than larger doses of individually provided phytochemicals. Combinations of ascorbic acid with a polyphenol or a phenolic acid, have resulted in antioxidant effects on the in vitro free radical oxidation of LDL that were greater than the sum of the individual effects (Yeomans et al., Eur J Nutr (2005) 44: 422-428). A synergistic interaction of polyphenolics or flavonoids with ascorbic acid has been indicated (Cossins et al., Biochem Mol Biol Int (1998) 45:583-597), possibly due to the ability of ascorbic acid to protect these compounds from oxidative degradation. A synergistic effect between phenolic acids and ascorbic acid can be explained by recycling of the phenoxyl radical by ascorbic acid and thereby yielding a stable ascorbyl radical. Flavonoids with a catechol structure in the B ring such as caffeic acid have a higher oxidation potential in comparison to ascorbic acid and thus a regeneration of the caffeic acid radicals by ascorbic acid could occur.

The extract or fraction of the at least one potato cultivar, and in certain embodiments, the Onaway, Purple Valley or Bora Valley potato cultivar or combination thereof as described herein, optionally complemented by the Russet Burbank potato cultivar, may be used, in certain non-limiting embodiments, to improve insulin sensitivity and glucose tolerance, to improve blood lipids and reduce adiposity, or in a method of preventing or treating diabetes mellitus (type-2) or obesity, since the high content of phenolics in these extracts have been separately shown to exert prophylactic and therapeutic outcomes in such individuals (Paynter et al., Am J Epidemiol (2006) 164:1075-1084; Srinivasan et al., J Clin Biochem Nutr. (2007) 40:92-100).

The extract or fraction of the at least one potato cultivar, and in certain embodiments, the Onaway, Purple Valley or Bora Valley potato cultivar or combination thereof as described herein, optionally complemented by Russet Burbank potato cultivar, may also be used, in other non-limiting embodiments, in methods of treating or preventing hyperlipidemia.

In further non-limiting embodiments, the described extracts of the at least one potato cultivar may be used in a method of treating or preventing cancer.

The extract or fraction of the at least one potato cultivar, in further non-limiting embodiments, may also be used to treat chronic inflammatory diseases, such as rheumatoid arthritis or lupus, diabetes, obesity, reproductive problems, inflammatory bowel disease, appendicitis, cardiovascular complications including atherosclerosis, plaque formation, ischemia, blood clots, congestive heart failure, heart attacks and strokes, liver diseases, respiratory disorders such as asthma emphysema, bronchitis, chronic obstructive lung disease, and other lung diseases, hypertension, or eye and nasal irritation, due to the high levels of antioxidant and anti-inflammatory agents. More specifically, phytochemicals within potato have been shown to exert antioxidant protection equivalent to synthetic counterparts such as butylated hydroxytoluene (BHT) (Rodriguez-Saona L et al., J Food Sci (1999) 64:445-450).

The extract or fraction of at least one potato cultivar as described herein may also be used, in further non-limiting embodiments, to counteract the effects of oxidants associated with air or other waste-related types of pollution. There is increasing evidence that air pollution exposure results in increased oxidative stress and that dietary supplementation may play a modulating role on the acute effect of pollutants (Romieu et al., Eur Respir J (2008) 31:179-97). However, the study of antioxidant supplements until now has shown limited protection, and contrasting results on lung function and inflammatory response in relation to oxidant exposure in humans. It is likely that these trials, which have focused on antioxidant vitamin supplements, were less effective due to the more limited protection afforded by these nutrients when compared to the concept of systemic protection provided by phytochemical cocktails as described herein. Without wishing to be bound by theory, it is thought that the extracts or fractions of at least one potato cultivar as described herein exert systemic protective effects to pollutant-related exposure by concurrently targeting different molecular and physiological processes, such as cytoprotective genes like NRF2 and direct effects on detoxifying enzymes, and has beneficial properties when compared with the targeting of specific pathways with synthetic molecules, drugs, or nutrients.

In a non-limiting embodiment, the invention accordingly provides methods of treating chronic inflammatory diseases that are aggravated by particulates and/or pollution, such as asthma, complications related to heart disease, hypertension, chronic obstructive lung disease, and eye irritation, by administering an extract or fraction of the at least one potato cultivar as described herein. Additionally, these combinations may be used in a method to protect against the development of immune dysregulation and lower IQ associated with chronic pollutant exposures.

The above-described methods may be adapted for human or veterinary (domestic and zoo or other wild animals) therapeutic purposes. As such, the subject may be a human or other mammal including, but not limited to horse (equine), cattle (bovine, beef, or dairy cow), swine (pig, porcine), sheep (ovine) or goat (caprine), dog (canine), cat (feline), rabbit (lapine), chicken, turkey, duck and other poultry, rat, hamsters, guinea pigs or mouse (rodents). In a non-limiting example of a veterinary application, the methods and compositions described herein may be adapted for treatment or prevention of oxidative stress or inflammatory diseases or disorders in livestock in order to increase production yields.

According to the present invention, an extract of at least one potato cultivar, and in certain non-limiting embodiments a combination of stem tubers from Onaway optionally complemented by Russet Burbank potato cultivar, or other varieties such as the Purple Valley or Bora Valley potato cultivars, provides an important source of the phytochemicals and bioflavonoid described herein, and which are important active compounds that exert health benefits. It has also surprisingly been found that these antioxidants can be extracted from the stem tuber cortex and pith of these potato cultivars without any pretreatment, as well as from the stem tuber skin, which is rich in polyphenolics. Accordingly, these phytochemicals and bioflavonoid can be derived from the skin, cortex, or pith of the stem tubers of these potato cultivars, or combinations thereof, without need for pretreatment. Thus, large quantities of these important active compounds can be obtained from potato cultivars grown naturally, with a cost-effective production mode, and which are already considered safe to eat by the general public as compared with genetically modified (GM) counterparts.

As discussed above, extracts or fractions of at least one potato cultivar, such as Onaway or a combination of Onaway with Russet Burbank potato cultivar, or other varieties such as the Purple Valley or Bora Valley potato cultivars, are contemplated herein. In certain non-limiting embodiments, it will be desirable to remove toxic glycoalkaloids (including solanine and chaconine), which are naturally concentrated just beneath the skin (Zhao J et al., J Agric Food Chem (1994) 42: 2570-73) of the tuber. In other non-limiting embodiments, it will be desirable to remove residues of nitrates and chemical sprout inhibitors on the surface (Lang (1992) http://www.geocities.com/willboyne/nosurrender/PeelsBad.html) of the tuber. Drying and leaching techniques can be used to reduce the glycoalkaloids, but care should be taken to monitor these processes since they are known to deplete phytochemical content. Alkaline treatment can also be used as it precipitates ~90% of the glycoalkaloids, but again monitoring is desirable since some anthocyanin degradation (approx. 30%) occurs (Rodriguez-Saona L et al., J Food Sci (1999) 64:445-450) as well as degradation of phenolic acids. In other non-limiting embodiments, it may be preferable to prepare the aforementioned extracts from the pith and cortex regions of the tuber. In these embodiments the need for separate processing to remove the toxic glycoalkaloids, nitrate and chemical sprout inhibitor residues will be significantly reduced or even eliminated. Peel removal could involve mechanical abrasion, the use of steam, or other means.

Extracts and fractions as described herein may be prepared, in certain non-limiting embodiments, using one or more liquid extraction steps. For instance, yet without wishing to be limiting, the source material may be extracted using solvents including water, acids and alcohol(s) such as methanol (MeOH), ethanol (EtOH), isopropanol, or combinations thereof. In a preferred embodiment, the source material is extracted in a solvent system of about 5 to about 100% alcohol such as MeOH, 0 to about 10% acid such as metaphosphoric acid, and 0 to about 10 mM EDTA, more preferably 50% MeOH, 2.5% metaphosphoric acid and 1 mM EDTA.

Liquid extraction steps may be carried out according to a variety of methods, which methods may include without limitation steps of mixing followed by separation. For instance, in a non-limiting embodiment, the source material may be mixed by vortexing followed by centrifugation to remove solid material. Multiple steps of mixing and separating may also be used, including 2, 3, 4, 5 or more steps. In an embodiment, which is not meant to be limiting in any way, the source material may be mixed by vortexing for up to about 2 minutes, preferably up to about 30 seconds, followed by separation of the mixture by centrifugation. In such embodiments, non-limiting centrifugation step(s) may be carried out at sufficient time and speed to remove substantially all of the solid material from solution. Without wishing to be limiting in any way, a centrifugation step may be carried out at about 5,000×g to about 20,000×g, including any centrifugation speed within this range, preferably between about 10,000×g to about 15,000×g, more preferably about 11,070×g. The time required for the centrifugation step will typically be dependent upon the speed, and in certain non-limiting embodiments may be up to 1 hour or even more. The centrifugation time will typically be between about 5 minutes to about 30 minutes, more preferably about 15 minutes. Without limitation, the centrifugation steps as well as any of the additional separation steps may be carried out at room temperature or lower, preferably at about 4° C.

Concentration of supernatant fractions may also be carried out in a variety of ways, including by lyophilization (freeze-drying), spray-drying, rota-evaporating or other evaporating technologies, and other non-limiting concentrating methods.

The extraction process may also include microwave, pressure-processing, or supercritical fluid extraction either separately or in combination with one or more chromatographic separation steps, for instance but not limited to separation by high-pressure liquid chromatography (HPLC), to further separate bioactive components of the extracted materials. The extraction process may also include one or more quantification and identification steps to measure the phytochemical content of the extract, including the content of ascorbic acid, chlorogenic acids, caffeic acid, ferulic acid, rutin, and anthocyanins.

The initial source material of the composition or extract as described herein may comprise, without limitation, whole Onaway, or in further non-limiting embodiments, Onaway complemented by Russet Burbank, or other varieties such as Purple Valley or Bora Valley potatoes, portions of the aforesaid potatoes including but not limited to the pith, cortex, skin, or combinations thereof, and further including processed forms thereof including freeze-dried or spray-dried powder, concentrated solutions, and others.

The pharmaceutical and nutraceutical compositions as described herein may include the described active components or extracts together with an acceptable carrier or excipient, or together with one or more separate active agents or constituents as part of a pharmaceutical or nutraceutical combination. In addition, the pharmaceutical compositions may be administered in a treatment regime with other drugs or pharmaceutical compositions, either separately or in a combined formulation or combination.

Such compositions will preferably be formulated with a vehicle pharmaceutically acceptable for administration to a subject, preferably a human, although veterinary uses (domestic and zoo or other wild animals) are also applicable, in need thereof. Methods of formulation for such compositions are well known in the art and taught in standard reference texts such as *Remington's Pharmaceutical Sciences*, Mack Publishing Co., Easton, Pa., 1985.

Formulations expected to be useful in the present invention may include, but are not limited to, aqueous solutions (where water soluble), dispersions and powders that are stable under the conditions of manufacture and storage and will preferably be preserved against the contaminating action of microorganisms such as bacteria and fungi. The vehicle can be a solvent or dispersion medium containing, for example, water, ethanol, polyol (for example, glycerols, mono- and di-glycerols, propylene glycol, liquid polyethylene glycol, and the like), suitable mixtures thereof, and oils (e.g., edible oils including but not limited to vegetable, fruit, nut, fish oils, and mineral oils). The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition.

Sterile solutions can be prepared by incorporating the composition in the required amount in an appropriate solvent with one or a combination of ingredients enumerated above, as required, followed by filter sterilization. Generally, dispersions are prepared by incorporating the composition into a sterile vehicle which contains a basic dispersion medium and the required other ingredients from those enumerated above. In the case of sterile powders for the preparation of sterile solutions, the preferred methods of preparation are vacuum drying and freeze-drying which yield a powder, optionally plus any additional desired ingredient from a previously sterile-filtered solution thereof.

Suspensions, in addition to the active agent or cell extract as described herein, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Solid dosage forms for oral administration of a compound of the present invention include, but are not limited to, ingestible hard and soft capsules, tablets, pills, candy, chewing gum, lollipops, powders, granules, elixirs, suspensions, syrups, wafers, sublingual or buccal tablets, troches, and the like. In such solid dosage forms the compound is mixed with at least one inert, pharmaceutically acceptable excipient or diluent or assimilable edible carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the compound of the invention in the compositions and preparations may, of course, be varied. The amount of compound in such therapeutically useful compositions is such that a suitable dosage will be obtained.

The solid dosage forms of tablets, dragees, capsules, pills, and granules can be prepared with coatings and shells such as enteric coatings and other coatings well known in the pharmaceutical and nutraceutical formulating art. They may optionally contain opacifying agents and can also be of a composition that they release the compound(s) of the invention only, or preferentially, in a certain part of the intestinal tract, optionally, in a delayed manner. Examples of embedding compositions, which can be used include polymeric substances and waxes. The compositions can also be in microencapsulated form, if appropriate, with one or more of the above-mentioned excipients.

Liquid dosage forms for oral administration include pharmaceutically acceptable emulsions, solutions, suspensions, syrups and elixirs. In addition to the compound of the invention, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the composition or extract as described herein, may contain suspending agents such as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Accordingly, the described compositions can be administered to a subject, preferably a mammal, more preferably a human, to treat and/or prevent disease. The compositions may be administered by various routes including, but not limited to, orally. The formulation and route of administration as well as the dose and frequency of administration can be selected routinely by those skilled in the art based upon the severity of the condition being treated, as well as patient-specific factors such as age, weight, and the like.

One skilled in the art recognizes that interspecies pharmacokinetic scaling can be used to study the underlining similarities (and differences) in drug disposition among species, to predict drug disposition in an untested species, to define pharmacokinetic equivalence in various species, and to design dosage regimens for experimental animal models, as discussed in Mordenti (1986), Man versus Beast: Pharmacokinetic Scaling in Mammals, 1028, J. Pharmaceutical Sciences, 75.

Definitions

The "skin" (periderm) is the thin protective layer on the outside of a stem tuber or potato. Its colour may vary between various shades of brown, white-cream, yellow, orange, red, blue, or purple. Some have two colors. The skin is usually smooth, and in some varieties russet (netted) or rough. It can be easily peeled off by rubbing when the tuber is immature. It is thicker and more difficult to remove as the tuber matures. It is generally industrially removed by mechanical abrasion or steam.

The "cortex" is a narrow band of storage tissue immediately below the skin, contains mainly protein and starch, and constitutes part of the tuber flesh which in commercial varieties is usually white, cream, or pale yellow but may vary between various shades of orange, red, blue, purple, and may be patterned with coloured and white portions.

The "pith" forms the central storage tissue of the tuber, collectively the perimedula and pith area within the vascular ring, and also constitutes part of the tuber flesh. Like the cortex, it contains mainly protein and starch and is similarly coloured to the cortex.

EXPERIMENTS

Experiment 1: Quantification of Antioxidants and Analysis of Seasonal Variation

Oral supplementation with certain phenolics (chlorogenic acids, caffeic acid, and ferulic acid), the vitamin ascorbic acid, the bioflavonoid rutin and anthocyanins has been used in animal and human trials to enhance anti-oxidant and anti-inflammatory protection, improve insulin sensitivity and glucose tolerance, improve blood lipids and reduce adiposity. However, there are no rich food sources in which these four phytochemical groups occur naturally together. The results presented herein indicate surprisingly high levels of these phytochemicals in extracts of several common cultivars: Onaway complemented by Russet Burbank (ascorbic acid, chlorogenic acids, caffeic acid, ferulic acid, and rutin) and Purple Valley or Bora Valley (chlorogenic acids, rutin and anthocyanins). Thus, yet without wishing to be limiting, combined extracts of Onaway complemented by Russet Burbank with Purple Valley or Bora Valley will provide a natural supplement that contains a high content of all five phytochemicals which can work synergistically to provide health benefits Using HPLC, the present inventors have quantified the content of ascorbic acid and the phenolics: chlorogenic acid, caffeic acid, ferulic acid, and rutin (FIGS. 1-4). This assay was based on the method developed by Shakya and Navarre (J Agric Food Chem (2006) 54:5253-5260). Initially, samples (50 mg of freeze-dried powder) were extracted in 0.9 mL of extraction buffer (50% MeOH, 2.5% metaphosphoric acid, 1 mM EDTA) in a 2 mL screw cap tube. Samples were vortexed for 30 sec and centrifuged at 11,070×g for 15 min at 4° C. The supernatant was transferred to a 1.5 mL glass vial. The remaining pellet was re-extracted with 0.6 mL of extraction buffer and centrifuged. The supernatants were combined and concentrated in a Speed Vac (Thermo Savant SC 210A, Waltham, Mass.). The concentrated samples were solubilised with 500 mL of extraction buffer and filtered using 0.45 mm membrane filters (Durapore, PVDF) into 1 mL HPLC glass vials. Samples were kept chilled at all times and shielded from bright light. Samples were analyzed using a Varian HPLC system with a quaternary gradient pump, a single wavelength UV/VIS detector, and an autosampler with refrigerated sample compartment (Varian Canada Inc, Mississauga, ON). Samples were eluted using an Onyx reverse-phase HPLC column (100×4.5 mm) (Phenomenex, Netherlands), a solvent flow rate of 2 mL/min and a solvent gradient of 0-1 min 100% buffer A (10 mM formic acid, pH 3.5, with NH4OH), 1-5 min 0-30% buffer B (100% methanol with 5 mM ammonium formate), 5-6.5 min 40-0% buffer B, 6.5-8.5 min 70-100% buffer B. The phenolic acids in the samples were analyzed qualitatively and quantitatively using standards. The presence of relatively high levels of neochlorogenic acid together with chlorogenic acid in the Onaway and Bora Valley potato cultivar extracts was demonstrated using HPLC techniques (FIGS. 1-4). Significantly, carmitine palmitoyltransferase activity is enhanced by neochlorogenic acid but unaffected by chlorogenic acid (Shimoda et al. BMC Complementary and Alternative Medicine (2006) 6:1-9). Carnitine palmitoyltransferase is the outer mitochondrial membrane enzyme that controls entry of fatty acids into mitochondria and so is the rate-limiting enzyme for fatty acid β-oxidation. Enhancement of carnitine palmitoyltransferase activity is related to protection against dietary-fat induced obesity including by acting at the level of the brain mechanisms signaling satiety (Wolfgang et al., PNAS (2006) 103:7282-7287).

Although previous studies have demonstrated that the skin is a rich source of certain polyphenolics, the present inventors have determined that the skin and flesh of certain potato cultivars commonly grown in North America (i.e., Russet Burbank and Onaway) and the Korean cultivars Purple Valley and Bora Valley contain a surprisingly rich content of potent hypoglycemic and hypolipidemic antioxidant phytochemicals. These include, but are not limited to, chlorogenic acids, rutin, caffeic acid, ferulic acid and anthocyanins together with ascorbic acid. On a per kg fresh weight basis Bora Valley and Purple Valley (3,471 and 2,163 mg/kg, respectively; Table 8), compare exceptionally well relative to some of the richest fruit or vegetable sources of chlorogenic acid i.e., cherry ranges from 180-1150 mg/kg fresh weight (Manach et al., Am J Clin Nutr (2004) 79:727-47). Similarly, the chlorogenic acid, caffeic acid, ferulic acid, and rutin content of Russet Burbank and Onaway cultivars, which summatively ranged from 250-436 mg/kg fresh weight, respectively, have similar content to foods with a high content of these individual phenolics (Manach et al., Am J Clin Nutr (2004) 79:727-47) such as certain blueberries like rabbiteye blueberry with a rich ferulic acid content of 169.7 mg/kg (Sellappan S. et al., J Agricultural Food Chem (2002) 50:2432-2438).

1. Materials and Methods:
1.1 Potato Source Material:
Field-Grown North American Cultivars.

Tubers of 12 North American cultivars grown in the field in Canada: Atlantic, Goldrush, Green Mountain, Kennebec, Norland, Onaway, Red Pontiac, Russet Burbank, Sebago, Shepody, Superior, and Yukon Gold, were received from the Bon Accord Elite Seed Potato Centre (Bon Accord, NB, Canada). These were produced using conventional field practices for New Brunswick and harvested in September 2007 and 2008. The tubers were randomly selected from storage bins, bagged, boxed, and sent to McGill University by bus transport. Tubers were stored in their boxes in a walk-in fridge (4° C.) until analysis.

Minitubers of Foreign Cultivars.

Minitubers (small tubers collected from greenhouse-grown plants) of five foreign cultivars: Alwara (PI639204), Bora Valley (PI634776), Gogu Valley (PI634778), Gui Valley (PI642430), and Purple Valley (PI634780) were ordered from the USDA Potato Gene Bank, (Sturgeon Bay, Wis., USA). These were chosen from a published list of USDA-held cultivars and selections with "high antioxidant activity" or "deep purple colour". Minitubers were harvested, cleaned, bagged, and sent to McGill University by air transport. These were received during the winter of 2007 and 2008 and stored as above until analysis or planting at the McGill Horticultural Centre.

Field-Grown Foreign Cultivars.

Two minitubers per foreign cultivar were planted at the horticulture center, Macdonald Campus, McGill University and grown, using conventional field practices (summer 2008). These tubers were harvested in October 2008. At harvest, they were lifted, washed, bagged, and stored as described above until analysis 2 months later (end of November 2008).

1.2. Time Line for 2008-2009 Analyses:

Tuber samples (field-grown North American and foreign) were extracted in December 2008, freeze-dried, and stored in a −80° C. freezer. Antioxidant analyses using the FRAP and DPPH assays occurred in January and February 2009, respectively. HPLC analysis was done in March 2009.

1.3 Sample Extraction:

For each cultivar, 20 random tubers were weighed and 5 average-sized tubers (five replicates) were selected for analysis. Tubers were separated into 3 different tissues including periderm (skin), cortex, and pith, to find out if antioxidant and phenolic levels varied between different tissues within the same tuber. Periderm was thinly sliced, cortex and pith tissue were sampled (approx. 10 mm$^3$ size) and collected into labeled 20 ml plastic vials (Fisher Scientific, ON, Canada). Care was taken while separating the samples to avoid mixing between tissue samples. Vials were weighed using an analytical balance (Mettler Toledo, Switzerland) and reweighed after sample addition to determine sample fresh weight. Vials containing fresh tissue were placed into a container of liquid nitrogen for rapid freezing. Vials containing frozen samples were transferred to the freeze-dryer or collected in the −80° C. freezer until transfer to the freeze-dryer. The samples were freeze-dried to preserve the chemical properties of the sample. Following freeze-drying, the samples were weighed to determine the dry matter content of the samples compared with the fresh weight of the sample before freeze-drying. The samples were homogenized and stored in the −80° C. freezer until analysis.

1.4 Antioxidant Assay 1—Ferric Reducing Ability of Plasma (FRAP):

The FRAP assay is used to determine the total antioxidant potential of the sample through the reduction of the ferric tripyridyltriazine complex to a ferrous complex (Benzie and Strain, Anal Biochem (1996) 239:70-76). When a ferric tripyridyltriazine complex is reduced to the ferrous form by electron donation from the antioxidant molecules of the sample, an intense blue color is developed which is measured spectrophotometrically by a change in the absorbance at 593 nm. The FRAP reagent was prepared by mixing acetic acid buffer:TPTZ solution:ferric chloride solution in 10:1:1. Acetic acid buffer was prepared by mixing 16 ml of glacial acetic acid (Sigma, MO, USA) and 3.10 g of Sodium acetate trihydrate ($C_2H_3NaO_2 \cdot 3H_2O$) (Sigma, MO, USA) to make the final volume to 1 L with distilled water. TPTZ solution was prepared by mixing 0.3123 g of TPTZ (2, 4, 6-tripyridyl-s-triazine) (Sigma, MO, USA), and 0.33 ml HCl (1 M) (Fisher Scientific, ON, Canada) and making the final volume to 100 ml with distilled water. Ferric chloride solution was prepared by mixing 0.5406 g of ferric chloride solution (ACP Chemicals Inc, QC, Canada) in distilled water and making the final volume to 100 ml. The FRAP reagent was tested for its reactivity using an ascorbic acid dilution series to prepare a standard curve. Ascorbic acid solution was prepared by mixing 0.0088 g of ascorbic acid (Fisher Scientific, ON, Canada) in distilled water and making the final volume to 50 ml.

Using a micropipette, 50 µl of each diluted sample was poured into a 2 ml microcentrifuge tube (labeled 1-9). Later, 1.5 ml of FRAP reagent was added and vortexed for 60 s and the tubes were left to stand for 6 min at room temperature for the reaction to proceed. The samples were poured into 2.5 ml cuvettes (labeled from 1-9, blank, and control) using the transfer pipettes. The blank consisted of 1.5 ml distilled water. The control consisted of 1.5 ml FRAP reagent+50 µl distilled water. The samples were read in the spectrophotometer at 593 nm. The samples were fed to the spectrophotometer in the following order: blank, control, and dilution series samples (from greater to lesser dilution). The spectrophotometer readings were taken and from these a standard curve was prepared. The $R^2$ value was determined from the standard curve. A $R^2$ value >0.95 indicates good reactivity of the FRAP reagent. The potato samples were prepared by placing 10 mg of frozen powdered sample into a 1 ml microcentrifuge tube to which 1 ml of distilled water was added. The tubes were vortexed for 60 s, then centrifuged at 4° C. for 15 min at 5000 rpm. After centrifuging, 50 µl of the supernatant was collected into a 2 ml microcentrifuge tube to which 1.5 ml of FRAP reagent was added. The tubes were vortexed for 60 s and allowed to stand for 6 min at room temperature to enable the reaction to proceed between the FRAP solution and sample supernatant. The samples were then transferred into a 2.5 ml labeled cuvette and read in the spectrophotometer at 593 nm. The control consisted of 1.5 ml FRAP reagent and 50 µl of distilled water. The readings were transferred to an Excel spreadsheet for calculation of the quantity of antioxidants.

1.5 Antioxidant assay 2-DPPH (2, 2-Diphenyl-1-Picrylhydrazyl)

The antioxidant activity of the potato tuber samples was also estimated using the DPPH assay (McCune and Johns, Ethnopharmacol. (2002) 82:197-205). DPPH is a stable free radical, which on reaction with an antioxidant molecule that can donate hydrogen, reduces from a violet to a yellow colored diphenylpicrylhydrazine. This change in color is measured spectrophotometrically at 517 nm. The DPPH solution was prepared by mixing 3.94 mg of DPPH and methanol making the final volume to 100 ml with methanol in a 100 ml beaker. The DPPH reagent was tested for its reactivity using an ascorbic acid dilution series as done for the FRAP assay. The samples were prepared by placing 10 mg of powdered sample into each 1 ml microcentrifuge tube to which 1 ml of distilled water was added and vortexed for 60 s, then centrifuged at 4° C. for 15 min at 5000 rpm. After the centrifuging, 250 µl of the supernatant was collected into a 2 ml microcentrifuge tube into which 1.5 ml of DPPH solution was added and vortexed for 60 s. The tubes were left for 20 min for the reaction to proceed between the DPPH solution and sample supernatant. The samples were transferred into 2.5 ml labeled cuvettes and read in the spectrophotometer at 517 nm. The control consisted of 1.5 ml DPPH solution+250 µl of distilled water. The readings were transferred to an Excel spreadsheet for calculation of the quantity of antioxidants.

1.6 Quantification of Antioxidants, Including Polyphenolics—High Performance Liquid Chromatography (HPLC):

The type of phenolic acids present and their quantity in different tissues were tested using HPLC (Shakya and Navarre (2006); Vipin et al., J. Agric. Food Chem (2007) 55:1707-1711). Potato contains phenolic compounds and the predominant one among them is believed to be chlorogenic acid, which constitutes about 80% of the total according to the literature published to date of species and cultivars studied so far (Brown C R, Am J Potato Res (2005) 82:163-172. Other phenolic compounds may include protocatechoic acid, vanillic acid, and p-coumaric acid. Flavonoids like rutin, catechin, and epicatechin are also reported to be present at relevant concentrations in potato (Brown, 2005 supra). Antioxidant activity appeared to be correlated with total phenolic acids (Brown, 2005 supra).

HPLC was used to identify and quantify three phenolic acids: chlorogenic acid, caffeic acid, ferulic acid, as well as rutin. Ascorbic acid concentration was also determined as it is also an important antioxidant compound present in potato. HPLC determination is based on the retention time of a particular compound within a mixed sample in the column compared with purchased pure standards. Three different buffers (Buffer A, Buffer B, & Extraction buffer) were prepared. Buffer A was 10 mM formic acid (Fisher Scientific, ON, Canada) (0.46 g of formic acid in 1 L distilled water adjusted to pH 3.5 using 1 M $NH_4OH$ solution). Buffer A was kept in a fridge (4° C.) until used. Buffer B was 5 mM ammonium formate (Sigma-Aldrich Chemicals, Germany) (0.32 g of ammonium formate in 1 L 100% methanol with agitation on a magnetic stirrer as ammonium formate is highly insoluble). Buffer B was also refrigerated. The extraction buffer was 50% methanol (Fisher Scientific, ON, Canada), 2.5% metaphosphoric acid (Aldrich Chemicals, WI, USA) and 1 mM ethylenediaminetetraacetic acid (EDTA; Sigma-Aldrich Chemicals, Germany) (50 ml of 100% methanol, 2.5 g of metaphosphoric acid, and 0.4 g of EDTA in 100 ml distilled water with stirring followed by filtering using a cup filter (Millipore Corporation, MS, USA). The extraction buffer was also refrigerated.

1.6.1 Sample Preparation for Analysis:

The samples were prepared by placing 50 mg of powered sample into a 1.5 ml microcentrifuge tube along with 0.9 ml extraction buffer. The tubes were vortexed for 60 s and centrifuged at 4° C. for 15 min at 3000 rpm. The supernatant was collected into a 1.5 ml glass vial using a micropipette. 0.6 ml of extraction buffer was added to the same microcentrifuge tube from which the supernatant was collected. The tubes were again vortexed, then centrifuged at 4° C. for 15 min at 3000 rpm. This supernatant was collected into the same glass vial. The microcentrifuge tubes with supernatant were kept in a speed vac for 6-8 h until the extraction buffer had evaporated from the supernatant. 500 µl of extraction buffer was added to the glass vials containing supernatant that were run in the speed vac. These glass vials were vortexed for 60 s. The sample was extracted with a 1 ml syringe and filtered through a 0.2 µm Whatman™ nylon filter into a 1 ml glass vial and the vial was sealed using a rubber-topped metal lid. The phenolic acids of the samples were thereafter separated and quantified via HPLC chromatography. Based on peaks and the retention times of peaks in the chromatographs of the samples as compared with standards, the specific phenolic acids were identified and quantified based on standard curves obtained when the purchased standards were run.

1.7. Quantification of Potato Polyphenols and Glycoalkaloids α-Chaconine, and α-Solanine by ESI-TOF-MS Analysis Electrospray time-of-flight mass spectrometry (ESI-TOF-MS) was carried out for confirmation and verification of polyphenols for a routine HPLC-UV/Vis analysis. Phenolic compounds were separated based on the modified method of Shakya and Navarre 2006, using a reverse phase HPLC Gemini-NX (5 µm, 100 mm×4.6 mm) column (Phenomenex, Torrance, Calif., USA) and a 4.6 mm×2.0 mm guard column. Elution was achieved using solvent A (10 mM formic acid, pH 3.5) and B (5 mM ammonium formate solution in 100% methanol). Gradient conditions were: 0 min 5% B, 2 min 5% B, 5 min 30% B, 7 min 70% B, 9 min 100% B and 12 min 100% B with a flow rate of ml/min and 20 µL of sample were injected. Accurate mass data were obtained using an Agilent 1200 series high-performance liquid chromatography (HPLC) system equipped with an Agilent 6210 time-of-flight (ESI-TOF) mass spectrometer (Santa Clara, Calif.). The analyses were conducted using a dual ESI source in both positive and negative mode (injected in two different methods): data was acquired over a mass range of m/z 100-1000. The source was operated with the following parameters: temperature 350° C., gas flow 12 l/min, nebulizer 50 psi Capillary Voltage 4000V, Fragmentor 100V, Skimmer voltage 60V. Reference masses (internal calibration of high res spectra) were: Positive mode: m/z 121.050873, 922.009798 Negative mode: m/z 119.03632, 966.000725.

2. Experimental Design and Statistical Analysis:

Randomly selected tubers from seventeen field-grown cultivars (12 familiar North American, 5 foreign) were used. Five replicates (tubers with weight close to the average weight of 20 tubers) were tested from each cultivar. Analysis of variance (ANOVA) test using General Linear Model (GLM) was done to investigate differences between cultivars (main factors) and tissues, including periderm, cortex, and pith (sub-factors) of each cultivar.

Concentration data for each tissue was transformed using volume measurements recommended for specific cultivars (or averages from 20 cultivars) as in Ortiz-Medina et al. (2009) [(Ortiz-Medina et al., J Food Sci (2009) 74:S177-S181) to obtain a virtual tuber of 100 g FW. This enables logical inter-cultivar comparisons. Virtual tuber means were compared using Tukey's comparison test at $P \le 0.05$. Pearson's correlation test was conducted to determine the correlation among different analysis means at $P \le 0.05$. The results of year 2008/2009 were compared with those from a 2007/2008 Kubow/Donnelly data set (extractions, FRAP and DPPH assays, HPLC analysis performed in 2008) to investigate the inter-seasonal variations.

3. Results 3.1 Antioxidant Activities:

3.1.1 FRAP (Ferric Reducing Ability Plasma):

For the field-grown North American cultivars there was a greater spread in antioxidant activity values in 2008 compared with 2007 (Table 1), as well as greater antioxidant values overall (Table 2). Inter-seasonal variation in FRAP antioxidant values was evident, which could be caused by growing conditions and duration of tuber storage before the analysis. Storage duration was longer in 2007 than in 2008.

'Red Pontiac' was consistently in the top group for FRAP in both 2007 and 2008. 'Kennebec' and 'Sebago' were similar in FRAP value to 'Red Pontiac' in 2007 and were again among the top cultivars in 2008 (Table 1). 'Norland' and 'Atlantic' had the least FRAP value in both 2007 and 2008. The antioxidant activities of the foreign cultivars, which were analyzed only in year 2008, were in the middle of a wide range of domestic cultivars. On average, the field-grown North American and foreign cultivars were not different in FRAP value (Table 3).

Individual tuber tissues had significantly different FRAP values in the field-grown North American cultivars, when averaged over 2 years for all cultivars. Pith had the greatest amount of antioxidant activity (and greatest volume) followed by cortex (lesser volume), and skin (least volume) (Table 4).

TABLE 1

Virtual tuber FRAP means as ascorbic acid equivalents (μg/100 g FW) for field-grown North American cultivars harvested 2007, 2008 and Foreign cultivars harvested 2008.

| 2007 | | 2008 | |
|---|---|---|---|
| Cultivars | Means | Cultivars | Means |
| Kennebec | 2762.7 $^a$ | Red Pontiac | 4249.4 $^a$ |
| Sebago | 2698.9 $^{ab}$ | Shepody | 2972.4 $^b$ |
| Red Pontiac | 2007.7 $^{abc}$ | Onaway | 2954.3 $^{bc}$ |
| Goldrush | 1830.2 $^{bcd}$ | Sebago | 2916.4 $^{bc}$ |
| Green Mountain | 1761.1 $^{cd}$ | Bora Valley | 2574.5 $^{bcd}$ |
| Onaway | 1729.9 $^{cd}$ | Kennebec | 2526.7 $^{bcd}$ |
| Shepody | 1687.2 $^{cd}$ | Goldrush | 2506.0 $^{bcd}$ |
| Yukon Gold | 1552.4 $^{cd}$ | Purple Valley | 2080.3 $^{bcde}$ |
| Russet Burbank | 1421.3 $^{cd}$ | Green Mountain | 1904.2 $^{bcde}$ |
| Superior | 1335.1 $^{cd}$ | Gui Valley | 1806.6 $^{cdef}$ |
| Atlantic | 1062.9 $^d$ | Gogu Valley | 1713.6 $^{def}$ |
| Norland | 1042.9 $^d$ | Superior | 1684.0 $^{def}$ |
| | | Alwara | 1524.8 $^{def}$ |
| | | Russet Burbank | 1508.8 $^{defg}$ |
| | | Yukon Gold | 960.8 $^{efg}$ |
| | | Norland | 715.5 $^{fg}$ |
| | | Atlantic | 372.1 $^g$ |

The means with same superscript are not significantly different at P ≤ 0.05 (Tukey's test).

TABLE 2

Virtual tuber FRAP mean for field-grown North American cultivars showing inter-seasonal differences in 2007 and 2008.

| 2008 | 2075.16 $^a$ |
|---|---|
| 2007 | 1752.06 $^b$ |

The means with same superscript are not significantly different at P ≤ 0.05 (Tukey's test).

TABLE 3

Virtual tuber FRAP mean for field-grown North American cultivars compared with field-grown foreign cultivars showing no difference (2008).

| Field-grown North American cultivars | 2075.2 $^a$ |
|---|---|
| Foreign cultivars | 1934.1 $^a$ |

The means with same superscript are not significantly different at P ≤ 0.05 (Tukey's test).

TABLE 4

Virtual tuber FRAP mean of field-grown North American cultivars averaged over 2 years (2007 and 2008).

| Pith | 1252.53 $^a$ |
|---|---|
| Cortex | 612.15 $^b$ |
| Periderm (skin) | 47.03 $^c$ |

The means with same superscript are not significantly different at P ≤ 0.05 (Tukey's test).

3.1.2 DPPH (2, 2-Diphenyl-1-Picrylhydrazyl):

As with the FRAP values, there was a greater spread in antioxidant values (Table 5) and significantly greater overall DPPH values in 2008 compared with 2007 (Table 6). In 2008, the DPPH values for field-grown foreign cultivars were significantly greater than for the field-grown North American cultivars (Table 7).

In 2007, Kennebec, Sebago, and Red Pontiac were in the top group (as for FRAP) but this group also included Russet Burbank, Shepody, and Superior. Norland and Atlantic were in the bottom group (as for FRAP) that also included Goldrush, Onaway, and Yukon Gold (Table 5).

In 2008, the foreign cultivars Purple Valley and Bora Valley showed significantly greater DPPH antioxidant activity than other cultivars. 'Kennebec', 'Red Pontiac' and others were the North American cultivars in the top group while 'Yukon Gold' had the least DPPH antioxidant value.

Some cultivars identified as having greater antioxidant levels in the FRAP assay were also closer to the top for DPPH (Kennebec, Red Pontiac, Sebago, Shepody). In both years there were some inconsistencies in the order of the cultivars with greatest to least antioxidant values, as compared with the FRAP, and there was also inter-seasonal variation. For example, 'Russet Burbank', which had the greatest antioxidant activity in 2007 showed significantly lower antioxidant activity relative to some domestic cultivars in 2008. This inter-seasonal variation could be because of the difference in the growing conditions and duration of storage of the tubers before the analysis.

TABLE 5

Virtual tuber DPPH means (μg/100 g FW) of cultivars analyzed in 2007 and 2008.

| Virtual Tuber DPPH Means 2007 (μg/100 g FW) | | Virtual Tuber DPPH Means 2008 (μg/100 g FW) | |
|---|---|---|---|
| Cultivars | Means | Cultivars | Means |
| Russet Burbank | 3028.0 $^a$ | Purple Valley | 4793.2 $^a$ |
| Superior | 2653.8 $^{ab}$ | Bora Valley | 3840.8 $^{ab}$ |
| Sebago | 2354.8 $^{abc}$ | Alwara | 2817.9 $^{bc}$ |
| Kennebec | 2109.9 $^{abc}$ | Onaway | 2453.5 $^{cd}$ |
| Shepody | 2091.0 $^{abc}$ | Red Pontiac | 2333.2 $^{cde}$ |
| Red Pontiac | 1896.3 $^{abc}$ | Kennebec | 2162.8 $^{cdef}$ |
| Green Mountain | 1701 $^{bc}$ | Gogu Valley | 1898.9 $^{cdef}$ |
| Yukon Gold | 1591.5 $^{bcd}$ | Sebago | 1791.4 $^{cdefg}$ |
| Onaway | 1383.7 $^{cd}$ | Shepody | 1742.3 $^{cdefg}$ |
| Atlantic | 1316.4 $^{cd}$ | Goldrush | 1671.5 $^{cdefg}$ |
| Goldrush | 1290.8 $^{cd}$ | Gui Valley | 1469.5 $^{defg}$ |
| Norland | 380.3 $^d$ | Atlantic | 1337.1 $^{defg}$ |
| | | Green Mountain | 1193.6 $^{efg}$ |
| | | Superior | 1129 $^{fg}$ |
| | | Norland | 1076.8 $^{fg}$ |
| | | Russet Burbank | 1059.3 $^{fg}$ |
| | | Yukon Gold | 677.7 $^g$ |

The means with same superscript are not significantly different at P ≤ 0.05 (Tukey's test).

TABLE 6

Virtual tuber DPPH mean of field-grown North American cultivars showing inter-seasonal differences over 2 years (2007 and 2008).

| 2008 | 1774.68 $^a$ |
|---|---|
| 2007 | 1553.96 $^b$ |

The means with same superscript are not significantly different at P ≤ 0.05 (Tukey's test).

TABLE 7

Virtual tuber DPPH mean of field-grown North American cultivars and foreign cultivars (2008).

| Foreign cultivars | 2887.90 $^a$ |
|---|---|
| Field-grown North American cultivars | 1554.0 $^b$ |

The means with same superscript are not significantly different at P ≤ 0.05 (Tukey's test).

3.2 HPLC (High Performance Liquid Chromatography):
3.2.1 Total Antioxidants and Total Phenolics "Total antioxidants" were derived by summing the values for ascorbic acid, chlorogenic acid, caffeic acid, ferulic acid, and rutin. This value may be adjusted based on confirmation and quantification of isomers of chlorogenic acid (crypto- and neo-chlorogenic acid) and several other phenolics.

"Total phenolics" were derived by summing the values for chlorogenic acid, caffeic acid, ferulic acid, and rutin. This value may be adjusted based on confirmation and quantification of isomers of chlorogenic acid (crypto- and neo-chlorogenic acid) and several other phenolics.

In 2007, Atlantic, Goldrush, Green Mountain Red Pontiac, Russet Burbank, and Sebago were in the group with the greatest total antioxidants. These cultivars also had high ascorbic acid levels, while Goldrush was also the top cultivar for total phenolics. The phenolic profiles of these cultivars varied, with Goldrush having the greatest chlorogenic acid content and Onaway showing the greatest content of caffeic acid, ferulic acid and rutin (Table 8). Comparison of the 2007 and 2008 data on the same cultivars showed distinct inter-seasonal differences for some, but not all cultivars. Thus, Goldrush did not show consistently high levels of chlorogenic acid whereas Onaway was of interest for the consistent year-to-year high levels of caffeic acid, ferulic acid and rutin. Similarly, Russet Burbank was of interest for consistently high levels of ferulic acid and rutin in both 2007 and 2008.

The foreign cultivars had lesser ascorbic acid levels but significantly greater chlorogenic acid levels compared with the North American-grown cultivars. Two Korean cultivars were particularly notable. Bora Valley showed significantly more total phenolic compounds compared with the North American and the other foreign cultivars, with Purple Valley showing the second greatest total phenolic content among all cultivars.

The virtual tuber means of the North American cultivars of ascorbic acid, rutin, total antioxidants (TA) and total phenolics (TP) of cultivars tested in 2008 were significantly greater than the same cultivars tested in 2007 (Table 9). On the other hand, chlorogenic, caffeic and ferulic acids did not have significantly different values between the two years (Table 9). Between the North American and foreign cultivars tested for 2008, North American cultivars were significantly greater than foreign cultivars in terms of ascorbic acid, caffeic acid, ferulic acid, and total antioxidant virtual tuber mean concentrations (Table 10). Conversely, foreign cultivars had significantly greater virtual tuber mean concentrations of chlorogenic acids, rutin, and total phenolics as compared with the North American cultivars (Table 10).

In 2007, FRAP and DPPH were highly significantly positively correlated with each other but not significantly correlated with total antioxidants (TA) or total phenolics (TP) (Table 11). Total antioxidants were weakly positively correlated with total phenolics but highly correlated with ascorbic acid, moderately with chlorogenic acid, and moderately negatively with ferulic acid.

In 2008, FRAP and DPPH were again significantly correlated with one another for the field-grown North American cultivars, even more so than in 2007 (Table 12) and were moderately positively correlated for the foreign cultivars. FRAP and DPPH were significantly correlated with total phenolics but not total antioxidants in the North American cultivars but highly significantly positively correlated with both in the foreign cultivars (Table 13). Total antioxidants were not correlated with total phenolics but highly correlated with ascorbic acid in the North American cultivars (Table 12). In contrast, total antioxidants and total phenolics were highly significantly correlated with one another, chlorogenic acid, and rutin in the foreign cultivars (Table 13).

TABLE 8

Virtual tuber HPLC values (μg/100 g FW) for ascorbic acid and four major phenolic compounds (chlorogenic acid, caffeic acid, ferulic acid, rutin) in 12 field-grown Canadian cultivars and 5 foreign field grown cultivars

| Cultivars | Ascorbic acid 2007 | Ascorbic acid 2008 | Chlorogenic acid 2007 | Chlorogenic acid 2008 | Caffeic acid 2007 | Caffeic acid 2008 | Ferulic acid 2007 | Ferulic acid 2008 |
|---|---|---|---|---|---|---|---|---|
| Goldrush | $2034.3^a$ | $4339.9^a$ | $679.48^a$ | $100.61^b$ | $22.64^{bcde}$ | $17.59^b$ | $11.60^{de}$ | $2.41^g$ |
| Shepody | $1191.4^{abc}$ | $4149.9^{ab}$ | $99.34^{cde}$ | $171.51^b$ | $6.61^e$ | $35.52^b$ | $30.79^{bcde}$ | $30.97^{cdef}$ |
| Sebago | $1888^{ab}$ | $3545.4^{abc}$ | $178.44^c$ | $182.41^{ab}$ | $10.83^e$ | $36.62^b$ | $31.54^{bcde}$ | $21.61^{defg}$ |
| Onaway | $496.7^c$ | $3472.2^{abc}$ | $106.83^{cde}$ | $265.74^a$ | $73.88^a$ | $88.04^a$ | $83.43^a$ | $84.12^b$ |
| Atlantic | $2072.0^a$ | $3459.1^{abc}$ | $118.06^{cd}$ | $132.68^b$ | $14.05^{de}$ | $30.23^b$ | $17.18^{de}$ | $12.78^{efg}$ |
| Superior | $1371.3^{abc}$ | $3037.3^{bcd}$ | $59.22^{de}$ | $157.66^b$ | $54.20^{abcd}$ | $21.72^b$ | $13.17^{de}$ | $24.06^{defg}$ |
| Norland | $385.3^c$ | $3030.1^{bcd}$ | $27.62^e$ | $175.25^{ab}$ | $39.48^{abcde}$ | $20.43^b$ | $51.86^{abc}$ | $38.58^{cd}$ |
| Yukon Gold | $883.8^{bc}$ | $3004.3^{bcd}$ | $135.09^{cd}$ | $122.35^b$ | $19.41^{cde}$ | $29.43^b$ | $30.62^{bcde}$ | $27.15^{cdefg}$ |
| Kennebec | $1332.3^{abc}$ | $2744.9^{cde}$ | $55.2^{de}$ | $155.91^b$ | $39.91^{abcde}$ | $17.22^b$ | $40.71^{bcd}$ | $35.68^{cde}$ |
| Red Pontiac | $1883.2^{ab}$ | $2304.4^{cde}$ | $69.92^{de}$ | $148.71^b$ | $59.5^{abc}$ | $35.52^b$ | $21.71^{cde}$ | $51.49^e$ |
| Green Mountain | $2089.4^a$ | $1891.3^{de}$ | $277.66^b$ | $125.17^b$ | $14.94^{de}$ | $18.37^b$ | $7.83^c$ | $18.33^{defg}$ |
| Russet Burbank | $1439.5^{abc}$ | $1754.8^e$ | $100.24^{cde}$ | $100.38^b$ | $65.72^{ab}$ | $18.51^b$ | $62.34^{ab}$ | $110.04^a$ |
| Alwara | | $913.2^{de}$ | | $871.6^c$ | | $15.75^b$ | | $8.22^{fg}$ |
| Gui Valley | | $858.4^{de}$ | | $407^d$ | | 0 | | $19.33^{defg}$ |
| Purple valley | | $454.2^e$ | | $2162.8^b$ | | 0 | | $3.67^g$ |
| Bora Valley | | $146.2^e$ | | $3470.9^a$ | | 0 | | $18.14^{defg}$ |
| Gogu Valley | | $145.9^e$ | | $319.9^d$ | | 0 | | $5.453^g$ |

TABLE 8-continued

Virtual tuber HPLC values (μg/100 g FW) for ascorbic acid and four major phenolic compounds
(chlorogenic acid, caffeic acid, ferulic acid, rutin) in 12 field-grown Canadian cultivars and
5 foreign field grown cultivars

| Cultivars | Rutin 2007 | Rutin 2008 | Total Antioxidants (TP + ascorbic acid) 2007 | Total Antioxidants (TP + ascorbic acid) 2008 | Total Phenolics (TP) 2007 | Total Phenolics (TP) 2008 |
|---|---|---|---|---|---|---|
| Goldrush | 22.35$^{de}$ | 82.69$^{b}$ | 2770.37$^{a}$ | 4543.2$^{a}$ | 736.07$^{a}$ | 203.3$^{e}$ |
| Shepody | 39.72$^{cde}$ | 119.57$^{b}$ | 1367.86$^{bcde}$ | 4507.4$^{ab}$ | 176.45$^{ef}$ | 357.6$^{dc}$ |
| Sebago | 46.62$^{bcde}$ | 80.31$^{b}$ | 2155.43$^{abc}$ | 3866.35$^{abcd}$ | 267.43$^{bcdef}$ | 320.9$^{de}$ |
| Onaway | 75.37$^{ab}$ | 263.95$^{a}$ | 836.21$^{de}$ | 4174.05$^{abc}$ | 339.51$^{b}$ | 701.8$^{cd}$ |
| Atlantic | 53.03$^{bcd}$ | 74.37$^{b}$ | 2274.32$^{ab}$ | 3709.16$^{abcd}$ | 202.31$^{cdef}$ | 250.1$^{de}$ |
| Superior | 24.66$^{de}$ | 64.81$^{b}$ | 1522.55$^{bcde}$ | 3305.55$^{cde}$ | 151.24$^{f}$ | 268.3$^{de}$ |
| Norland | 60.36$^{bc}$ | 87.36$^{b}$ | 564.62$^{e}$ | 3351.8$^{bcd}$ | 179.31$^{def}$ | 321.6$^{de}$ |
| Yukon Gold | 98.63$^{a}$ | 86.76$^{b}$ | 1167.55$^{cde}$ | 3269.99$^{cde}$ | 283.74$^{bcde}$ | 265.7$^{de}$ |
| Kennebec | 41.12$^{cde}$ | 75.93$^{b}$ | 1509.76$^{bcde}$ | 3029.7$^{cdef}$ | 176.93$^{ef}$ | 284.7$^{de}$ |
| Red Pontiac | 40.26$^{cde}$ | 117.77$^{b}$ | 2074.59$^{abc}$ | 2903.6$^{def}$ | 191.39$^{def}$ | 355.2$^{de}$ |
| Green Mountain | 20.54$^{e}$ | 99.68$^{b}$ | 2410.37$^{ab}$ | 2152.85$^{efg}$ | 320.96$^{bc}$ | 261.5$^{de}$ |
| Russet Burbank | 73.80$^{ab}$ | 122.1$^{b}$ | 1741.6$^{abcd}$ | 2105.83$^{fg}$ | 302.09$^{bcd}$ | 351$^{de}$ |
| Alwara | | 65.46$^{b}$ | | 1874.3$^{fg}$ | | 961.6$^{c}$ |
| Gui Valley | | 71.04$^{b}$ | | 1376.4$^{gh}$ | | 518$^{cde}$ |
| Purple valley | | 232.34$^{a}$ | | 2931.5$^{def}$ | | 2413.6$^{b}$ |
| Bora Valley | | 287.23$^{a}$ | | 3937.7$^{abcd}$ | | 3791.5$^{a}$ |
| Gogu Valley | | 74.74$^{b}$ | | 529$^{h}$ | | 398$^{de}$ |

The means with same superscript are not significantly different at $P \leq 0.05$ (Turkey's test).

TABLE 9

Mean virtual tuber HPLC values (μg/100 g FW) for ascorbic acid, four major
phenol compounds (chlorogenic acid, caffeic acid, ferulic acid, rutin), for
12 field-grown North American cultivars over 2 years (2007, 2008).*

| | Ascorbic acid | Chlorogenic acid | Caffeic acid | Ferulic acid | Rutin | Total Phenolics | Total Antioxidants |
|---|---|---|---|---|---|---|---|
| 2008 | 3091.81$^{a}$ | 153.85$^{a}$ | 31.26$^{a}$ | 37.94$^{a}$ | 108.76$^{a}$ | 331.80$^{a}$ | 3423.61$^{a}$ |
| 2007 | 1422.26$^{b}$ | 158.93$^{a}$ | 35.09$^{a}$ | 33.56$^{a}$ | 49.70$^{b}$ | 277.29$^{b}$ | 1699.54$^{b}$ |

The means with same superscript are not significantly different at $P \leq 0.05$ (Tukey's test).
*These units do not include the isomers neo- or crypt-chlorogenic acid (data to come)

TABLE 10

Mean virtual tuber HPLC values (μg/100 g FW) for ascorbic acid, four major
phenolic compounds (chlorogenic acid, caffeic acid, ferulic acid, rutin),
total phenolics and total antioxidants (ascorbic acid + total phenolics)
for 12 field-grown North American and 5 foreign cultivars (2008).*

| | Ascorbic acid | Chlorogenic acid | Caffeic acid | Ferulic acid | Rutin | Total Antioxidants | Total Phenolics |
|---|---|---|---|---|---|---|---|
| North American | 3034.30$^{a}$ | 151.51$^{b}$ | 30.87$^{a}$ | 37.74$^{a}$ | 108.03$^{b}$ | 3362.40$^{a}$ | 328.14$^{b}$ |
| Foreign | 506.20$^{b}$ | 1392.81$^{a}$ | 15.75$^{b}$ | 10.39$^{b}$ | 146.16$^{a}$ | 2053.60$^{b}$ | 1558.42$^{a}$ |

The means with same superscript are not significantly different at $P \leq 0.05$ (Tukey's test).
C—North American cultivars;
F—Foreign cultivars
*These units do not include the isomers neo- or crypto-chlorogenic acid (data to come)

TABLE 11

Pearson correlation coefficient results for field-grown North American cultivars
(2007) - Virtual tuber FRAP, DPPH, and HPLC.[1]

| | Ascorbic | Chlorogenic | Caffeic | Ferulic | Rutin | TA | TP | FRAP | DPPH |
|---|---|---|---|---|---|---|---|---|---|
| Ascorbic | | (+) W* NS | (−) W *** | (−) M | (−) M* | (+) H *** | (+) W NS | (+) W NS | (+) W NS |

TABLE 11-continued

Pearson correlation coefficient results for field-grown North American cultivars (2007) - Virtual tuber FRAP, DPPH, and HPLC.[1]

| | Ascorbic | Chlorogenic | Caffeic | Ferulic | Rutin | TA | TP | FRAP | DPPH |
|---|---|---|---|---|---|---|---|---|---|
| Chlorogenic | (+) W * | | (−) W NS | (−) W * | (−) W * | (+) M *** | (+) H *** | (+) W NS | (−) W NS |
| Caffeic | (−) W NS | (−) W NS | | (+) M *** | (+) W NS | (−) W NS | (+) W NS | (+) W NS | (+) W NS |
| Ferulic | (−) M *** | (−) W * | (+) M *** | | (+) M *** | (−) M *** | (−) W NS | (+) W NS | (+) W NS |
| Rutin | (−) M * | (−) W * | (+) W NS | (+) M *** | | (−) M * | (−) W NS | (−) W NS | (−) W NS |
| TA | (+) H *** | (+) M *** | (−) W NS | (−) M *** | (−) M * | | (+) M * | (+) W NS | (+) W NS |
| TP | (+) W NS | (+) H *** | (+) W NS | (−) W NS | (−) W NS | (+) M * | | (+) W NS | (−) W NS |
| FRAP | (+) W NS | (+) W NS | (+) W NS | (+) W NS | (−) W NS | (+) W NS | (+) W NS | | (+) M *** |
| DPPH | (+) W NS | (−) W NS | (+) W NS | (+) W NS | (−) W NS | (+) W NS | (−) W NS | (+) M *** | |

(+) = Positively correlated;
(−) = negatively correlated.
W = weakly correlated (Pearson correlation coefficient 0.01-0.4);
M = moderately correlated (Pearson correlation coefficient (0.41-0.7);
H = highly correlated (Pearson correlation coefficient 0.71-1)
Significance: NS = not significant; * $P < 0.05$;  $P < 0.001$; * $P < 0.0001$.
[1]These values did not include the isomers neo- or crypto-chlorogenic acid (data to come)

TABLE 12

Pearson correlation coefficient results for field-grown North American cultivars (2008) - Virtual tuber FRAP, DPPH, HPLC.[1]

| | Ascorbic | Chlorogenic | Caffeic | Ferulic | Rutin | TA | TP | FRAP | DPPH |
|---|---|---|---|---|---|---|---|---|---|
| Ascorbic | | (+) W NS | (+) W NS | (−) W * | (+) W NS | (+) H *** | (+) W NS | (+) W NS | (+) W NS |
| Chorogenic | (+) W NS | | (+) M *** | (+) W NS | (+) M ** | (+) W * | (+) H *** | (+) W * | (+) M ** |
| Caffeic | (+) W NS | (+) M *** | | (+) M * | (+) H *** | (+) W * | (+) H *** | (+) W * | (+) M ** |
| Ferulic | (−) W * | (+) W NS | (+) M * | | (+) M *** | (−) W NS | (−) M *** | (+) W NS | (+) W NS |
| Rutin | (+) W NS | (+) M ** | (+) H *** | (+) M *** | | (+) W NS | (+) H *** | (+) W * | (+) W * |
| TA | (+) H *** | (+) W * | (+) W * | (−) W NS | (+) W NS | | (+) W NS | (+) W NS | (+) W NS |
| TP | (+) W NS | (+) H *** | (+) H *** | (−) M *** | (+) H *** | (+) W NS | | (+) W * | (+) M ** |
| FRAP | (+) W NS | (+) W * | (+) W * | (+) W NS | (+) W * | (+) W NS | (+) W * | | (+) H *** |
| DPPH | (+) W NS | (+) M ** | (+) M ** | (+) W NS | (+) W * | (+) W NS | (+) M ** | (+) H *** | |

(+) = Positively correlated;
(−) = negatively correlated.
W = weakly correlated (Pearson correlation coefficient 0.01-0.4);
M = moderately correlated (Pearson correlation coefficient (0.41-0.7);
H = highly correlated (Pearson correlation coefficient 0.71-1)
Significance: NS = not significant; * $P < 0.05$;  $P < 0.001$; * $P < 0.0001$.
[1]These values did not include the isomers neo- or crypto-chlorogenic acid (data to come)

TABLE 13

Pearson correlation coefficient results - foreign cultivars (2008) virtual tuber FRAP, DPPH, HPLC.[1]

| | Ascorbic | Chlorogenic | Caffeic | Ferulic | Rutin | TA | TP | FRAP | DPPH |
|---|---|---|---|---|---|---|---|---|---|
| Ascorbic | | (−) W* | (+) M NS | (+) W NS | (−) M * | (−) W NS | (−) M * | (−) M NS | (−) W NS |
| Chlorogenic | (−) W * | | (+) M NS | (−) W NS | (+) H *** | (+) H *** | (+) H *** | (+) H *** | (+) H *** |
| Caffeic | (+) M NS | (−) M NS | | (−) M NS | (+) H * | (+) M NS | (+) M NS | (+) W NS | (+) W NS |

TABLE 13-continued

Pearson correlation coefficient results - foreign cultivars (2008) virtual tuber FRAP, DPPH, HPLC.[1]

| | Ascorbic | Chlorogenic | Caffeic | Ferulic | Rutin | TA | TP | FRAP | DPPH |
|---|---|---|---|---|---|---|---|---|---|
| Ferulic | (+) W NS | (−) W NS | (−) M NS | | (−) W NS | (−) W NS | (−) W NS | (+) W NS | (−) M *S |
| Rutin | (−) M * | (+) H *** | (+) H * | (−) W NS | | (+)H *** | (+)H *** | (+) H *** | (+) H *** |
| TA | (−) W NS | (+) H *** | (+) M NS | (−) W NS | (+)H *** | | (+) H *** | (+) H *** | (+) H *** |
| TP | (−) M * | (+) H *** | (+) M NS | (−) W NS | (+) H *** | (+) H *** | | (+) H *** | (+) H *** |
| FRAP | (−) M NS | (+) H *** | (+) W NS | (+) W NS | (+) H *** | (+) H *** | (+) H *** | | (+) M * |
| DPPH | (−) W NS | (+) H *** | (+) W NS | (−) M *S | (+) H *** | (+) H *** | (+) H *** | (+) M * | |

(+) = Positively correlated;
(−) = negatively correlated.
W = weakly correlated (Pearson correlation coefficient 0.01-0.4);
M = moderately correlated (Pearson correlation coefficient (0.41-0.7);
H = highly correlated (Pearson correlation coefficient 0.71-1)
Significance: NS = not significant; * $P < 0.05$;  $P < 0.001$; * $P < 0.0001$.
[1]These values did not include the isomers neo- or crypto-chlorogenic acid Based on the two antioxidant activity analyses performed (FRAP, DPPH) and HPLC determination of total phenolic and ascorbic acid content, Onaway is the cultivar that showed consistently, from year to year, the greatest amount of total antioxidant activity and phenolics in its extracts.

The extracts can contain Onaway complemented with Russet Burbank with either Bora Valley or Purple Valley for this unique blend of combinational extracts. The combination of extracts from (i) Onaway with its consistently high phenolic content, (particularly in terms of rutin, ferulic acid, and caffeic acid) and its the total antioxidant activity complemented by Russet Burbank the high levels of ferulic acid and rutin of Russet Burbank, together with (ii) Bora Valley and Purple Valley with the high total antioxidant activity and very high levels of chlorogenic acids, rutin and anthocyanin will provide a unique and potent antioxidant and phytochemical content of these combinational extracts.

Experiment 2: Analysis of Storage Conditions on Antioxidant Capacity and Polyphenolic Content of Potato Tubers 4. Materials and Methods:
4.1 Potato Source Material:
Field-Grown North American Cultivars.

Tubers were as described in section 1.1, produced using conventional field practices for New Brunswick and harvested in September 2008. The tubers were randomly selected from storage bins, bagged, boxed, and sent to McGill University by bus transport. Tubers were stored in their boxes in a walk-in cold room (5±1° C.) until analysis.
Minitubers of Foreign Cultivars.

Minitubers were as described in section 1.1, harvested, cleaned, bagged, and sent to McGill University by air transport. These were received during the winter of 2008 and stored as above until analysis or planting at the McGill Horticultural Centre.
Field-Grown Foreign Cultivars.

Two minitubers per foreign cultivar were planted at the horticulture center, Macdonald Campus, McGill University and grown, using conventional field practices (summer 2008).

These tubers were harvested in October 2008. At harvest, they were lifted, washed, bagged, and stored as described above until analysis 2 months later (end of November 2008).
4.2 Time Line for Analyses:

Tuber samples (field-grown North American and foreign) were extracted twice; after 1 month storage (November, 2008) and again after 7 months storage (May, 2009).
4.3 Sample Extraction:

For each cultivar, 20 random tubers were weighed and 5 average-sized tubers (five replicates) were selected for analysis at each sampling time. Tubers were otherwise treated as described in section 1.3.
4.4 Antioxidant Assays:
Ferric Reducing Ability of Plasma (FRAP): as described in section 1.4 above.
DPPH (2, 2-Diphenyl-1-Picrylhydrazyl): as described in section 1.5 above.
4.6 Quantification of Antioxidants, Including Polyphenolics—High Performance Liquid Chromatography (HPLC):
As described in section 1.6 and 1.6.1 above.
5. Experimental Design and Statistical Analysis:

The experiment was designed as Completely Randomized Design (CRD) with two main factors; cultivar and storage time (1 and 7 months), three sub-factors within each cultivar; skin, cortex and pith. For each cultivar, five replicates were tested and each replicate was represented by one tuber. The tubers for analysis in each cultivar were selected based on confidence interval values of tuber masses. Results were analyzed for variance (ANOVA) test using General Linear Model (GLM) of Statistical Analysis System (SAS) (SAS v 9.2, 2010) (SAS Institute Inc., Cary, N.C., USA). Means of the results were compared using Duncan's Multiple Comparison tests (P≤0.05). The results from 1 and 7 months storage were compared using t-tests to investigate the effect of storage on antioxidant capacity and polyphenolics in individual cultivars. Pearson's correlation test was conducted to determine the correlation among different analysis means.

Concentration data (mg/g DM) for each tissue was transformed into whole/virtual tuber data (mg/100 g FM) using unique conversion factors recommended for specific cultivars which were based on volume measurements (Ortiz-Medina et al., 2009). Conversion-factor mean values for 20 cvs. (Ortiz-Medina et al., 2009) were used for the foreign cultivars whose conversion factors were not determined. This enables logical comparison across the cultivars with different tuber shapes and masses.

6. Results 6.1 Antioxidant Determination Assay—2,2 Diphenyl-1-Picryl Hydrazyl (DPPH)

a. Twelve Canadian Grown Cultivars

DPPH analysis on potato tubers stored for 1 month, showed significant variation in AOC among Canadian-grown cultivars, which ranged from 43.18±13.21 to 12.80±2.45 mg AAE/100 g FM (Table 14). Cultivars Onaway and Red Pontiac had the greatest tuber DPPH values, while Green Mountain, Yukon Gold, Russet Burbank, Superior, and Norland had the least.

TABLE 14

T-test for significance between virtual tuber (100 g FM) DPPH means of 12 Canadian-grown cultivars analyzed 1 and 7 months after storage. Values expressed as means ± SE (n = 5). Data arranged based on alphabetical order of cultivars.

| Cultivars | 1 month storage (mg AAE/ 100 g FM) | 7 month storage (mg AAE/ 100 g FM) | Significance | (% reduction from 1 to 7 months storage) |
|---|---|---|---|---|
| Atlantic | 23.53 ± 1.60 $^{cd}$ | 12.41 ± 0.58 $^{cd}$ | 0.000* | 47.24 |
| Green Mountain | 21.00 ± 1.49 $^{de}$ | 11.47 ± 0.62 $^{d}$ | 0.000* | 45.41 |
| Goldrush | 32.71 ± 1.75 $^{b}$ | 14.08 ± 1.23 $^{c}$ | 0.000* | 56.95 |
| Kennebec | 38.06 ± 3.26 $^{ab}$ | 11.28 ± 0.55 $^{d}$ | 0.000* | 70.37 |
| Norland | 18.95 ± 1.17 $^{de}$ | 20.53 ± 0.15 $^{a}$ | 0.216 | −8.33 |
| Onaway | 43.18 ± 5.91 $^{a}$ | 17.24 ± 0.65 $^{b}$ | 0.002* | 60.07 |
| Russet Burbank | 18.64 ± 1.03 $^{de}$ | 5.89 ± 0.33 $^{e}$ | 0.000* | 68.38 |
| Red Pontiac | 42.03 ± 4.04 $^{a}$ | 12.85 ± 0.40 $^{cd}$ | 0.000* | 69.42 |
| Sebago | 31.53 ± 2.23 $^{bc}$ | 11.99 ± 0.74 $^{cd}$ | 0.000* | 61.97 |
| Shepody | 30.66 ± 2.75 $^{bc}$ | 12.89 ± 0.54 $^{cd}$ | 0.000* | 57.97 |
| Superior | 19.87 ± 1.28 $^{de}$ | 11.42 ± 0.44 $^{d}$ | 0.000* | 42.53 |
| Yukon Gold | 12.80 ± 1.10 $^{e}$ | 13.77 ± 0.93 $^{c}$ | 0.519 | −7.58 |
| Mean | 27.75 ± 1.43 | 12.99 ± 0.47 | | 47.03 |

*T-test significance at $P \leq 0.05$; Values with same superscript in the columns are not significantly different at $P \leq 0.05$.

Storage period (1 and 7 months) affected tuber AOC; with significant reduction in all the cultivars except Norland and Yukon Gold (Table 14). Response to storage, however, varied with cultivar. Three of the cultivars with the greatest AOC at 1 month (Onaway, Red Pontiac and Kennebec) demonstrated major decreases in AOC by 7 months whereas cultivars with lower values at 1 month showed a lesser effect of storage on AOC (Table 14). However, two cultivars with among the least AOC at 1 month had either the greatest (Norland; 20.53±0.34 mg AAE/100 g FM) or the least AOC (Russet Burbank; 5.89±0.74) at 7 months, underlining cultivar-specific effects of storage on AOC. Tuber tissues showed significant variation in AOC as skin showed the greatest AOC (DPPH) values, followed by pith and cortex, at both storage intervals (Table 15).

TABLE 15

Tuber tissue (skin, cortex, and pith) concentrations; DPPH and FRAP means of 12 Canadian-grown and 5 foreign cultivars analyzed 1 and 7 months after storage. Values expressed as means ± SE (n = 60 and 25 in Canadian and foreign cultivars respectively).

| | 12 Canadian-grown cultivars (mg AAE/g DM) | | 5 Foreign cultivars (mg AAE/g DM) | |
|---|---|---|---|---|
| | DPPH | FRAP | DPPH | FRAP |
| | 1 month storage | | | |
| Cortex | 1.13 ± 0.05 $^{c}$ | 1.37 ± 0.10 $^{c}$ | 1.25 ± 0.06 $^{b}$ | 1.10 ± 0.04 $^{b}$ |
| Pith | 1.28 ± 0.08 $^{b}$ | 1.79 ± 0.14 $^{b}$ | 1.09 ± 0.05 $^{c}$ | 1.18 ± 0.06 $^{b}$ |
| Skin | 3.33 ± 0.09 $^{a}$ | 2.88 ± 0.09 $^{a}$ | 2.74 ± 0.06 $^{a}$ | 4.59 ± 0.17 $^{a}$ |
| | 7 months storage | | | |
| Cortex | 0.49 ± 0.02 $^{c}$ | 0.52 ± 0.03 $^{c}$ | 0.54 ± 0.04 $^{b}$ | 0.61 ± 0.05 $^{b}$ |
| Pith | 0.62 ± 0.03 $^{b}$ | 0.58 ± 0.03 $^{b}$ | 0.55 ± 0.04 $^{b}$ | 0.60 ± 0.05 $^{b}$ |
| Skin | 1.95 ± 0.09 $^{a}$ | 1.60 ± 0.04 $^{a}$ | 1.64 ± 0.07 $^{a}$ | 1.98 ± 0.13 $^{a}$ |

Values with same superscript in the columns are not significantly different at $P \leq 0.05$.

At 1 month, tuber AOC measured using DPPH was significantly positively correlated with AOC measured using FRAP, and with chlorogenic acid, caffeic acid, and rutin but not ascorbic acid or ferulic acid (Table 16). After 7 months storage, tuber AOC as assessed by the DPPH assay was significantly positively correlated with AOC measured with FRAP as well as with chlorogenic acid, rutin, and ascorbic acid and not with caffeic acid demonstrating altered relationships between AOC measures and phytochemical content with storage (Table 17).

TABLE 16

Virtual tuber mean correlations among ascorbic acid, chlorogenic acid, caffeic acid, ferulic acid, rutin, FRAP and DPPH in 12 Canadian-grown cultivars after 1 month storage (Pearson's Correlation Coefficient test).

| | AA | CHA | CFA | FA | RT | FRAP | DPPH |
|---|---|---|---|---|---|---|---|
| AA | 1.00 | (0.24) NS | (0.26) * | (−0.40) ** | (0.02) NS | (0.16) NS | (0.23) NS |
| CHA | (0.24) NS | 1.00 | (0.63) *** | (0.23) NS | (0.46) *** | (0.27) * | (0.40) ** |
| CFA | (0.26) * | (0.63) *** | 1.00 | (0.38) ** | (0.72) *** | (0.33) * | (0.50) *** |
| FA | (−0.40) ** | (0.23) NS | (0.38) ** | 1.00 | (0.57) *** | (0.11) NS | (0.14) NS |
| RT | (0.02) NS | (0.46) *** | (0.72) *** | (0.57) *** | 1.00 | (0.27) * | (0.35) ** |
| FRAP | (0.16) NS | (0.27) * | (0.33) * | (0.11) NS | (0.27) * | 1.00 | (0.81) *** |
| DPPH | (0.23) NS | (0.40) ** | (0.50) *** | (0.14) NS | (0.35) ** | (0.81) *** | 1.00 |

(Pearson's $r^2$);
NS—Not significant;
* Significant at the 0.05 probability level;
** Significant at the 0.01 probability level;
*** Significant at the 0.001 probability level.
Ascorbic acid (AA), chlorogenic acid (CHA), caffeic acid (CFA), ferulic acid (FA), rutin (RT), FRAP and DPPH.

TABLE 17

Virtual tuber mean correlations among ascorbic acid, chlorogenic acid, caffeic acid, ferulic acid, rutin, FRAP and DPPH in 12 Canadian-grown cultivars after 7 months storage (Pearson's Correlation Coefficient test).

|      | AA          | CHA         | CFA         | FA          | RT          | FRAP        | DPPH        |
|------|-------------|-------------|-------------|-------------|-------------|-------------|-------------|
| AA   | 1.00        | (0.41) **   | (−0.30) *   | (−0.18) NS  | (0.15) NS   | (0.27) *    | (0.38) **   |
| CHA  | (0.41) **   | 1.00        | (−0.24) NS  | (−0.30) NS  | (−0.31) *   | (0.01) NS   | (0.64) ***  |
| CFA  | (−0.30) NS  | (−0.24) NS  | 1.00        | (−0.36) NS  | (0.23) NS   | (0.00) NS   | (−0.09) NS  |
| FA   | (−0.18) NS  | (−0.30) NS  | (−0.36) NS  | 1.00        | (0.14) NS   | (−0.17) NS  | (−0.21) NS  |
| RT   | (0.15) NS   | (−0.31) *   | (0.23) NS   | (0.14) NS   | 1.00        | (0.38) **   | (0.38) **   |
| FRAP | (0.27) *    | (0.01) NS   | (0.00) NS   | (−0.17) NS  | (0.38) **   | 1.00        | (0.40) **   |
| DPPH | (0.38) **   | (0.64) ***  | (−0.09) NS  | (−0.21) NS  | (0.38) **   | (0.40) **   | 1.00        |

(Pearson's $r^2$);
NS—Not significant;
* Significant at the 0.05 probability level;
** Significant at the 0.01 probability level;
*** Significant at the 0.001 probability level.
Ascorbic acid (AA), chlorogenic acid (CHA), caffeic acid (CFA), ferulic acid (FA), rutin (RT), FRAP and DPPH.

b. Five Foreign Cultivars

As seen with the Canadian-grown potatoes, the foreign cultivars showed that AOC (DPPH) varied with cultivar at 1 month storage (Table 18). Tuber AOC was greatest in cvs. Bora Valley and Purple Valley (35.97±3.94 and 35.05±2.21 mg AAE/100 g FM, respectively) whereas tuber AOC was not significantly different among the other three foreign cultivars. Cultivar variation in tuber AOC was also evident at 7 months storage with cv. Bora Valley still showing the greatest AOC (21.04±0.73 mg AAE/100 g FM) and the smallest % decline in DPPH AOC with storage. Purple Valley had an intermediate AOC value at 7 months (18.09±1.80 mg AAE/100 g FM), while the other three cultivars had the lowest AOC values at 1 month. Purple Valley also demonstrated the greatest decrease in AOC with storage time. Overall, a significant reduction in AOC occurred from 1 to 7 months storage in tubers of all the cultivars with average AOC values at 7 months of 12.16±6.31 mg AAE/100 g FM as compared with an average AOC at 1 month of 25.31±8.84 mg AAE/100 g FM (Table 18). As observed with the Canadian-grown potatoes, the skin in foreign cultivars also had the greatest AOC at both 1 and 7 months storage. The cortex had a higher DPPH AOC value than the pith at 1 month storage whereas they showed no differences in DPPH AOC at 7 months storage in the foreign cultivars (Table 15).

TABLE 18

T-test for significance between virtual tuber (100 g FM) DPPH means of 5 foreign cultivars analyzed 1 and 7 months after storage. Values expressed as means ± SE (n = 5). Data arranged based on alphabetical order of cultivars.

| Cultivars | 1 month storage (mg AAE/ 100 g FM) | 7 month storage (mg AAE/ 100 g FM) | Signif-icance | (% reduc-tion from 1 to 7 months storage) |
|---|---|---|---|---|
| Alwara | 20.43 ± 0.67 [b] | 7.58 ± 0.16 [c] | 0.000* | 62.92 |
| Bora | 35.97 ± 1.76 [a] | 21.04 ± 0.33 [a] | 0.000* | 41.49 |
| Gogu | 17.19 ± 0.36 [b] | 7.24 ± 0.18 [c] | 0.000* | 57.89 |
| Gui Valley | 17.92 ± 1.02 [b] | 6.86 ± 0.32 [c] | 0.000* | 61.69 |
| Purple | 35.05 ± 0.99 [a] | 18.09 ± 0.80 [b] | 0.000* | 48.40 |
| Mean | 25.31 ± 1.77 | 12.16 ± 1.26 | | 54.47 |

*T-test significance at $P \leq 0.05$; Values with same superscript in the columns are not significantly different at $P \leq 0.05$.

For the foreign cultivars at 1 month of storage, AOC measured by DPPH was significantly positively correlated with the FRAP AOC, chlorogenic acid, and rutin. DPPH AOC was negatively correlated with ferulic acid content in the 1 month stored tubers (Table 19). At 7 months storage, tuber AOC measured with DPPH was again significantly positively correlated with the FRAP AOC, chlorogenic acid, and also with caffeic acid, and no longer with rutin and ferulic acid (Table 20).

TABLE 19

Virtual tuber mean correlations among ascorbic acid, chlorogenic acid, caffeic acid, ferulic acid, rutin, FRAP and DPPH in 5 foreign cultivars after 1 month storage (Pearson's Correlation Coefficient test).

|      | AA          | CHA         | CFA         | FA          | RT          | FRAP        | DPPH        |
|------|-------------|-------------|-------------|-------------|-------------|-------------|-------------|
| AA   | 1.00        | (−0.35) NS  | (−0.23) NS  | (0.45) *    | (−0.43) *   | (−0.36) NS  | (−0.27) NS  |
| CHA  | (−0.35) NS  | 1.00        | (0.41) NS   | (−0.42) *   | (0.94) ***  | (0.94) ***  | (0.89) ***  |
| CFA  | (−0.23) NS  | (0.41) NS   | 1.00        | (0.33) NS   | (0.30) NS   | (0.29) NS   | (0.22) NS   |
| FA   | (0.45) *    | (−0.42) *   | (0.33) NS   | 1.00        | (−0.48) *   | (−0.40) NS  | (−0.52) **  |
| RT   | (−0.43) *   | (0.94) ***  | (0.30) NS   | (−0.48) *   | 1.00        | (0.91) ***  | (0.88) ***  |
| FRAP | (−0.36) NS  | (0.94) ***  | (0.29) NS   | (−0.40) NS  | (0.91) ***  | 1.00        | (0.92) ***  |
| DPPH | (−0.27) NS  | (0.89) ***  | (0.22) NS   | (−0.52) **  | (0.88) ***  | (0.92) ***  | 1.00        |

(Pearson's $r^2$);
NS—Not significant;
* Significant at the 0.05 probability level;
** Significant at the 0.01 probability level;
*** Significant at the 0.001 probability level.
Ascorbic acid (AA), chlorogenic acid (CHA), caffeic acid (CFA), ferulic acid (FA), rutin (RT), FRAP and DPPH.

TABLE 20

Virtual tuber mean correlations among ascorbic acid, chlorogenic acid, caffeic acid, ferulic acid, rutin, FRAP and DPPH in 5 foreign cultivars after 7 months storage (Pearson's Correlation Coefficient test).

|      | AA          | CHA         | CFA         | FA          | RT          | FRAP         | DPPH         |
|------|-------------|-------------|-------------|-------------|-------------|--------------|--------------|
| AA   | 1.00        | (0.10) NS   | (−0.10) NS  | (0.59) *    | (0.31) NS   | (−0.08) NS   | (0.30) NS    |
| CHA  | (0.10) NS   | 1.00        | (0.79) ***  | (−0.50) NS  | (0.27) NS   | (0.76) ***   | (0.90) ***   |
| CFA  | (−0.10) NS  | (0.79) ***  | 1.00        | (−0.33) NS  | (0.38) NS   | (0.69) ***   | (0.54) **    |
| FA   | (0.59) *    | (−0.50) NS  | (−0.33) NS  | 1.00        | (0.30) NS   | (−0.43) NS   | (−0.50) NS   |
| RT   | (0.31) NS   | (0.27) NS   | (0.38) NS   | (0.30) NS   | 1.00        | (0.18) NS    | (0.20) NS    |
| FRAP | (−0.08) NS  | (0.76) ***  | (0.69) ***  | (−0.43)     | (0.18)      | 1.00         | (0.71) ***   |
| DPPH | (0.30) NS   | (0.90) ***  | (0.54) **   | (−0.50) NS  | (0.20) NS   | (0.71) ***   | 1.00         |

(Pearson's $r^2$);
NS—Not significant;
* Significant at the 0.05 probability level;
** Significant at the 0.01 probability level;
*** Significant at the 0.001 probability level.
Ascorbic acid (AA), chlorogenic acid (CHA), caffeic acid (CFA), ferulic acid (FA), rutin (RT), FRAP and DPPH.

6.2 Antioxidant Determination Assay—Ferric Reducing Antioxidant Power (FRAP)

a. Twelve Canadian Grown Cultivars

A wide range of variation was also found in the tuber AOC of cultivars analyzed using the FRAP assay, which showed a 6-fold variation between the cultivars with the greatest (Red Pontiac) and least (Atlantic) AOC (69.43±23.42 and 11.69±2.23 mg AAE/100 g FM respectively at 1 month storage (Table 21). The cv. Red Pontiac showed the greatest AOC. Cultivars Shepody, Onaway, Sebago had significantly higher FRAP AOC relative to the Atlantic, Green Mountain, Norland, Russet Burbank, Superior and Yukon Gold cvs. Cultivars Atlantic, Norland, and Yukon Gold showed the least AOC. The order of the cvs. with greatest and least AOC measured using FRAP and DPPH was the same. At 7 months, the AOC of cultivars varied widely, although the relative order was maintained with storage as Red Pontiac showed the greatest AOC (18.59±0.63) whereas Atlantic and Russet Burbank had the lowest AOC of 2.87±1.26 and 05.69±0.22 mg AAE/100 g FM, respectively.

TABLE 21

T-test for significance between virtual tuber (100 g FM) FRAP means of 12 Canadian-grown cultivars analyzed 1 and 7 months after storage. Values expressed as means ± SE (n = 5). Data arranged based on alphabetical order of cultivars.

| Cultivars | 1 month storage (mg AAE/ 100 g FM) | 7 month storage (mg AAE/ 100 g FM) | Significance | (% reduction from 1 to 7 months storage) |
|-----------|------------------------------------|------------------------------------|--------------|------------------------------------------|
| Atlantic  | 11.69 ± 1.00 $^g$                  | 2.87 ± 0.56 $^f$                   | 0.000*       | 75.47                                    |
| Green     | 32.23 ± 0.61 $^{cd}$               | 12.35 ± 1.06 $^{cde}$              | 0.000*       | 61.69                                    |
| Goldrush  | 42.41 ± 2.84 $^{bc}$               | 14.59 ± 1.26 $^{cde}$              | 0.000*       | 65.59                                    |
| Kennebec  | 42.57 ± 2.15 $^{bc}$               | 11.64 ± 0.24 $^{de}$               | 0.000*       | 72.66                                    |
| Norland   | 12.84 ± 1.69 $^{fg}$               | 12.50 ± 0.99 $^{cde}$              | 0.868        | 02.58                                    |
| Onaway    | 50.00 ± 5.20 $^b$                  | 15.06 ± 0.15 $^{abcd}$             | 0.000*       | 69.88                                    |
| Russet Burbank | 24.64 ± 2.65 $^{def}$         | 5.69 ± 0.22 $^f$                   | 0.000*       | 76.93                                    |
| Red Pontiac | 69.43 ± 10.47 $^a$               | 18.59 ± 0.28 $^a$                  | 0.001*       | 73.72                                    |
| Sebago    | 49.35 ± 5.44 $^b$                  | 12.03 ± 0.55 $^{cde}$              | 0.000*       | 75.63                                    |
| Shepody   | 51.60 ± 3.86 $^b$                  | 15.82 ± 2.18 $^{abc}$              | 0.000*       | 69.34                                    |
| Superior  | 28.50 ± 1.40 $^{de}$               | 10.95 ± 2.14 $^e$                  | 0.000*       | 61.57                                    |
| Yukon     | 18.58 ± 1.75 $^{efg}$              | 17.82 ± 2.29 $^{ab}$               | 0.798        | 04.07                                    |
| Mean      | 36.15 ± 2.46                       | 12.49 ± 0.66                       |              | 59.09                                    |

*T-test significance at P ≤ 0.05; Values with same superscript in the columns are not significantly different at P ≤ 0.05.

Storage of 7 months significantly reduced FRAP AOC in all the cvs. except Norland and Yukon Gold. A mean decline of 59.09% occurred in the AOC between 1 and 7 months (36.15±19.07 and 12.49±5.10 mg AAE/100 g FM at 1 and 7 months, respectively; Table 21). Cultivars showed varied response to storage. Cvs. Russet Burbank and Sebago had the greatest decline in AOC, with 76.93 and 75.63% respectively (Table 21), while cvs. Norland and Yukon Gold showed the least decline in AOC, with 2.58 and 4.07%, respectively.

Significant variation was found at 1 and 7 months storage in the FRAP AOC among the tuber tissues, with skin showing the greatest AOC values versus the pith and cortex (Table 15). The pith had significantly greater FRAP AOC versus the cortex at both 1 and 7 months storage (Table 15).

The AOC (FRAP) of tubers, measured at 1 month storage, was significantly positively correlated with AOC (DPPH), and with chlorogenic acid, caffeic acid, and rutin but not ascorbic acid (Table 16). At 7 months storage, AOC (FRAP) showed a significant positive correlation with DPPH, ascorbic acid, and rutin (Table 17).

b. Five Foreign Cultivars

Variation in AOC (FRAP) of the tubers from the foreign cultivars ranged from 38.64±4.15 to 17.98±1.25 mg AAE/ 100 g FM (Table 22). While cv. Bora Valley (38.64±4.15 mg AAE/100 g FM) showed the greatest AOC, followed by cv. Purple Valley (31.96±5.69 mg AAE/100 g FM), the cvs. Gogu Valley (17.98±1.25 mg AAE/100 g FM), Alwara (21.89±1.35 mg AAE/100 g FM), and Gui Valley (19.27±0.95 mg AAE/100 g FM) showed the least AOC. Cultivar variation in AOC of the tubers was also evident with storage period. The cv. Bora Valley still showed the greatest AOC value for FRAP after 7 mo storage, whereas the cv. Purple Valley had a higher FRAP AOC than Alwara, Gogu Valley, and Gui Valley cultivars.

TABLE 22

T-test for significance between virtual tuber (100 g FM) FRAP means of 5 foreign cultivars analyzed 1 and 7 months after storage. Values expressed as means ± SE (n = 5). Data arranged based on alphabetical order of cultivars.

| Cultivars | 1 month storage (mg AAE/ 100 g FM) | 7 month storage (mg AAE/ 100 g FM) | Signif- icance | (% reduc- tion from 1 to 7 months storage) |
|---|---|---|---|---|
| Alwara | 21.89 ± 1.35 $^c$ | 7.16 ± 0.24 $^c$ | 0.000* | 67.27 |
| Bora Valley | 38.64 ± 1.86 $^a$ | 23.68 ± 3.78 $^a$ | 0.007* | 38.73 |
| Gogu Valley | 17.98 ± 0.56 $^c$ | 11.11 ± 1.76 $^{bc}$ | 0.005* | 38.20 |
| Gui Valley | 19.27 ± 0.95 $^c$ | 8.95 ± 1.91 $^c$ | 0.001* | 53.57 |
| Purple Valley | 31.96 ± 2.54 $^b$ | 16.38 ± 1.86 $^b$ | 0.001* | 48.76 |
| Mean | 25.95 ± 1.76 | 13.46 ± 1.52 | | 49.31 |

*T-test significance at P ≤ 0.05; Values with same superscript in the columns are not significantly different at P ≤ 0.05.

Significant reduction in tuber AOC with prolonged storage was evident in all the foreign cultivars (Table 22). Cultivars varied widely in storage impact on AOC as the cv. Alwara showed the greatest reduction due to long-term storage (67.27%) while cvs. Gogu Valley and Bora Valley showed the least reduction (38.20 and 38.73%, respectively). Significant variation in AOC of the tuber tissues was found, with skin showing greatest AOC and no significant variation in FRAP AOC was observed between cortex and pith after short- or long-term storage (Table 15).

The FRAP AOC showed significant positive correlation with chlorogenic acid, rutin, and DPPH AOC in 1-month stored tubers (Table 19) and with chlorogenic acid, caffeic acid, and DPPH AOC in the 7-months stored tubers (Table 20). The above correlations were similar to those found with DPPH AOC in 1- and 7-months stored tubers.

6.3 Quantification of the Major Antioxidants—High Performance Liquid Chromatography (HPLC)

a. Twelve Canadian Cultivars

Five antioxidant compounds, including ascorbic acid, chlorogenic acid, caffeic acid, ferulic acid, and rutin were present in tubers of all 12 cvs. (Table 23). Ascorbic acid content varied significantly among cultivars; Goldrush and Shepody had the greatest levels (43.40±8.32 and 41.34±1.21 mg/100 g FM, respectively) and Russet Burbank and Green Mountain the least levels (14.39±3.01 and 18.91±1.05 mg/100 g FM, respectively) at 1-month storage. Chlorogenic acid also varied significantly between cultivars; cv. Onaway had the greatest content (2.66±0.52 mg/100 g FM) and cvs. Russet Burbank, Goldrush, Green Mountain, and Yukon Gold the least, with much lower values (0.98±0.15, 1.01±0.15, 1.25±0.14, and 1.28±0.46 mg/100 g FM, respectively). Cultivar Onaway tubers had relatively greater ascorbic acid content and significantly greatest chlorogenic acid, caffeic acid, and rutin content, at 1-month storage. Curiously, cv. Red Pontiac, which showed the greatest tuber AOC in both FRAP and DPPH assays, had relatively low ascorbic and chlorogenic acid contents at both 1- and 7-months storage.

TABLE 23

T-test for HPLC results showing the virtual tuber (100 g FM) means of ascorbic acid, chlorogenic acid, caffeic acid, ferulic acid, and rutin of 12 Canadian-grown cultivars analyzed 1 and 7 months after storage. Values expressed as means ± SE (n = 5). Data arranged based on alphabetical order of cultivars.

| Cultivars | 1 month | 7 months | Signif- icance |
|---|---|---|---|
| Ascorbic acid (mg/100 g FM) | | | |
| Atlantic | 34.59 ± 0.92 $^{bcd}$ | 6.52 ± 0.07 $^{cd}$ | 0.000* |
| Green Mountain | 18.91 ± 0.47 $^{fg}$ | 4.47 ± 0.17 $^f$ | 0.000* |
| Goldrush | 43.40 ± 3.72 $^a$ | 7.05 ± 0.18 $^{bc}$ | 0.000* |
| Kennebec | 27.45 ± 1.18 $^{de}$ | 6.38 ± 0.11 $^d$ | 0.000* |
| Norland | 30.30 ± 0.52 $^{cde}$ | 6.51 ± 0.06 $^{cd}$ | 0.000* |
| Onaway | 34.72 ± 0.85 $^{bcd}$ | 6.04 ± 0.54 $^{de}$ | 0.000* |
| Russet Burbank | 14.39 ± 1.35 $^g$ | 3.06 ± 0.20 $^g$ | 0.087 |
| Red Pontiac | 25.28 ± 0.43 $^{ef}$ | 4.26 ± 0.06 $^f$ | 0.000* |
| Sebago | 35.66 ± 2.48 $^{bc}$ | 5.46 ± 0.04 $^e$ | 0.000* |
| Shepody | 41.34 ± 0.54 $^{ab}$ | 10.03 ± 0.26 $^a$ | 0.000* |
| Superior | 31.97 ± 2.66 $^{cde}$ | 4.71 ± 0.05 $^f$ | 0.000* |
| Yukon Gold | 29.99 ± 0.31 $^{cde}$ | 7.34 ± 0.05 $^b$ | 0.000* |
| Mean | 30.67 ± 1.21 | 5.99 ± 0.23 | |
| Chlorogenic acid (mg/100 g FM) | | | |
| Atlantic | 1.33 ± 0.25 $^{bcd}$ | 0.93 ± 0.02 $^b$ | 0.146* |
| Green Mountain | 1.25 ± 0.06 $^{cd}$ | 0.31 ± 0.02 $^e$ | 0.000* |
| Goldrush | 1.01 ± 0.07 $^d$ | 0.38 ± 0.04 $^{de}$ | 0.000* |
| Kennebec | 1.56 ± 0.13 $^{bc}$ | 0.29 ± 0.01 $^e$ | 0.000* |
| Norland | 1.75 ± 0.11 $^{bc}$ | 1.61 ± 0.02 $^a$ | 0.240 |
| Onaway | 2.66 ± 0.23 $^a$ | 0.43 ± 0.02 $^d$ | 0.000* |
| Russet Burbank | 0.98 ± 0.07 $^d$ | 0.16 ± 0.00 $^f$ | 0.000* |
| Red Pontiac | 1.46 ± 0.05 $^{bcd}$ | 0.36 ± 0.02 $^{de}$ | 0.000* |
| Sebago | 1.83 ± 0.16 $^b$ | 0.46 ± 0.05 $^d$ | 0.000* |
| Shepody | 1.76 ± 0.21 $^{bc}$ | 0.76 ± 0.08 $^c$ | 0.001* |
| Superior | 1.76 ± 0.20 $^{bc}$ | 0.76 ± 0.04 $^c$ | 0.001* |
| Yukon Gold | 1.28 ± 0.21 $^{cd}$ | 0.93 ± 0.02 $^b$ | 0.127 |
| Mean | 1.55 ± 0.07 | 0.62 ± 0.05 | |
| Caffeic acid (mg/100 g FM) | | | |
| Atlantic | 0.30 ± 0.06 $^{bcd}$ | 0.02 ± 0.00 $^b$ | 0.002* |
| Green Mountain | 0.18 ± 0.01 $^d$ | 0.15 ± 0.00 $^a$ | 0.062 |
| Goldrush | 0.18 ± 0.01 $^d$ | traces$^c$ | 0.000* |
| Kennebec | 0.17 ± 0.01 $^d$ | traces$^c$ | 0.000* |
| Norland | 0.20 ± 0.01 $^d$ | 0.01 ± 0.00 $^c$ | 0.000* |
| Onaway | 0.88 ± 0.09 $^a$ | 0.02 ± 0.00 $^b$ | 0.000* |
| Russet Burbank | 0.19 ± 0.01 $^d$ | traces$^c$ | 0.000* |
| Red Pontiac | 0.37 ± 0.06 $^{bc}$ | Nil | |
| Sebago | 0.39 ± 0.05 $^b$ | Nil | |
| Shepody | 0.36 ± 0.03 $^{bc}$ | Nil | |
| Superior | 0.22 ± 0.00 $^{cd}$ | 0.01 ± 0.00 $^c$ | 0.000* |
| Yukon Gold | 0.27 ± 0.08 $^{bcd}$ | traces$^c$ | 0.012* |
| Mean | 0.31 ± 0.03 | 0.02 ± 0.01 | |
| Ferulic acid (mg/100 g FM) | | | |
| Atlantic | 0.13 ± 0.02 $^{gh}$ | 0.01 ± 0.00 $^d$ | 0.000* |
| Green Mountain | 0.18 ± 0.01 $^{fg}$ | traces$^d$ | 0.000* |
| Goldrush | 0.02 ± 0.00 $^h$ | Nil | 0.000* |
| Kennebec | 0.36 ± 0.06 $^{de}$ | 0.14 ± 0.02 $^a$ | 0.005* |
| Norland | 0.39 ± 0.02 $^{cd}$ | 0.04 ± 0.00 $^c$ | 0.000* |
| Onaway | 0.84 ± 0.09 $^b$ | Nil | |
| Russet Burbank | 1.07 ± 0.08 $^a$ | 0.07 ± 0.00 $^b$ | 0.000* |
| Red Pontiac | 0.49 ± 0.04 $^c$ | 0.02 ± 0.00 $^d$ | 0.000* |
| Sebago | 0.23 ± 0.03 $^{efg}$ | traces$^d$ | 0.000* |
| Shepody | 0.31 ± 0.01 $^{def}$ | 0.02 ± 0.00 $^d$ | 0.000* |
| Superior | 0.24 ± 0.01 $^{efg}$ | Nil | |
| Yukon Gold | 0.27 ± 0.00 $^{def}$ | 0.01 ± 0.00 $^d$ | 0.000* |
| Mean | 0.38 ± 0.04 | 0.04 ± 0.01 | |
| Rutin (mg/100 g FM) | | | |
| Atlantic | 0.74 ± 0.02 $^{de}$ | 0.05 ± 0.01 $^e$ | 0.000* |
| Green Mountain | 0.95 ± 0.12 $^{bcde}$ | Nil | |
| Goldrush | 0.83 ± 0.06 $^{cde}$ | 0.25 ± 0.01 $^{bc}$ | 0.000* |
| Kennebec | 0.76 ± 0.03 $^{cde}$ | 0.18 ± 0.01 $^{cd}$ | 0.000* |
| Norland | 0.87 ± 0.04 $^{bcde}$ | 0.17 ± 0.01 $^{cd}$ | 0.000* |
| Onaway | 2.64 ± 0.12 $^a$ | 0.47 ± 0.02 $^a$ | 0.000* |
| Russet Burbank | 1.24 ± 0.19 $^b$ | Nil | |
| Red Pontiac | 1.14 ± 0.16 $^{bc}$ | 0.16 ± 0.01 $^d$ | 0.000* |
| Sebago | 0.78 ± 0.04 $^{cde}$ | 0.18 ± 0.01 $^{cd}$ | 0.000* |

TABLE 23-continued

T-test for HPLC results showing the virtual tuber (100 g FM) means of ascorbic acid, chlorogenic acid, caffeic acid, ferulic acid, and rutin of 12 Canadian-grown cultivars analyzed 1 and 7 months after storage. Values expressed as means ± SE (n = 5). Data arranged based on alphabetical order of cultivars.

| Cultivars | 1 month | 7 months | Significance |
|---|---|---|---|
| Shepody | 1.10 ± 0.22 $^{bcd}$ | 0.27 ± 0.08 $^{b}$ | 0.008* |
| Superior | 0.70 ± 0.04 $^{e}$ | 0.11 ± 0.02 $^{de}$ | 0.000* |
| Yukon Gold | 0.90 ± 0.11 $^{bcde}$ | 0.12 ± 0.01 $^{de}$ | 0.000* |
| Mean | 1.05 ± 0.07 | 0.19 ± 0.02 | |

*T-test significance at P ≤ 0.05; Values with same superscript in the columns are not significantly different at P ≤ 0.05.

Significant reduction in quantity of the five antioxidant compounds analysed was shown from 1- to 7-months storage except for chlorogenic acid in cvs. Atlantic, Norland and Yukon Gold, and caffeic acid in cv. Green Mountain. While storage appeared to have the greatest impact on caffeic and ferulic acid content (average reduction of 92.16 and 90.21%, respectively), ascorbic acid and rutin (average decline of 80.48 and 81.50%, respectively) and chlorogenic acid levels (average reduction of 60.27%) appeared to be less affected (Table 24).

TABLE 24

Virtual tuber (100 g FM) HPLC means of 12 Canadian-grown cultivars analyzed after 1 or 7 months storage. Values expressed as means ± SE (n = 60). Data arranged based on alphabetical order of antioxidants.

| | 1 month (mg/100 g FM) | 7 months (mg/100 g FM) | (% reduction; from 1 to 7 months storage) |
|---|---|---|---|
| Ascorbic acid | 30.67 ± 1.21 $^{a}$ | 5.99 ± 0.23 $^{b}$ | 80.48 |
| Chlorogenic acid | 1.55 ± 0.07 $^{a}$ | 0.62 ± 0.05 $^{b}$ | 60.27 |
| Caffeic acid | 0.31 ± 0.03 $^{a}$ | 0.02 ± 0.01 $^{b}$ | 92.16 |
| Ferulic acid | 0.38 ± 0.04 $^{a}$ | 0.04 ± 0.01 $^{b}$ | 90.21 |
| Rutin | 1.05 ± 0.07 $^{a}$ | 0.19 ± 0.02 $^{b}$ | 81.50 |

Values with same superscript in the columns are not significantly different at P ≤ 0.05.

Significant variation in the quantity of the compounds analyzed was found in different tissues of the tuber with skin consistently showing the greatest concentration for all five phytochemicals measured (Table 25). The cortex and pith did not differ significantly in terms of the five phytochemicals measured (Table 25).

TABLE 25

Tuber tissue (skin, cortex, and pith) concentrations; HPLC means of 12 Canadian-grown cultivars over 1 and 7 months storage. Values expressed as means ± SE (n = 120).

| | Ascorbic acid (mg/g DM) | Chlorogenic acid (mg/g DM) | Caffeic acid (mg/g DM) | Ferulic acid (mg/g DM) | Rutin (mg/g DM) |
|---|---|---|---|---|---|
| Cortex | 0.86 ± 0.06 $^{b}$ | 0.04 ± 0.00 $^{b}$ | 0.01 ± 0.00 $^{b}$ | 0.01 ± 0.00 $^{b}$ | 0.03 ± 0.00 $^{b}$ |
| Pith | 0.79 ± 0.06 $^{b}$ | 0.03 ± 0.03 $^{b}$ | 0.01 ± 0.00 $^{b}$ | 0.01 ± 0.00 $^{b}$ | 0.03 ± 0.00 $^{b}$ |
| Skin | 1.42 ± 0.10 $^{a}$ | 1.40 ± 0.09 $^{a}$ | 0.06 ± 0.01 $^{a}$ | 0.22 ± 0.02 $^{a}$ | 0.17 ± 0.03 $^{a}$ |

Values with same superscript in the columns are not significantly different at P ≤ 0.05.

In tubers stored for 1 month, significant positive correlations were found between ascorbic acid and caffeic acid; between chlorogenic acid and caffeic acid, rutin, FRAP, and DPPH; between caffeic acid and all other compounds, FRAP and DPPH (Table 16). Significant negative correlations were found between ascorbic and ferulic acids in tubers stored for 1 month.

b. Five Foreign Cultivars

HPLC results showed the presence of significant quantities of ascorbic acid, chlorogenic acid, caffeic acid, ferulic acid, and rutin in all five foreign cultivars at 1 month of storage, but no caffeic acid was observed in cv. Gogu Valley (Table 26). Chlorogenic acid was the predominant compound present in the foreign cultivars and ranged widely from 35.05±3.15 to 3.20±0.53 mg/100 g FM. The purple coloured cv. Bora Valley which showed the greatest tuber AOC in both FRAP and DPPH assays also showed significantly greater quantities of chlorogenic acid, caffeic acid, and rutin among the five cultivars. Similarly, cv. Purple Valley that had relatively higher FRAP and DPPH AOC values relative to cv. Gogu Valley, Alwara, and Gui Valley, also had significantly higher concentrations of chlorogenic acid and rutin in comparison to the above cultivars. In contrast, cv. Gui Valley had the greatest concentrations of ferulic acid relative to the other five cultivars with cv. Purple Valley showing the lowest concentrations.

TABLE 26

T-test for HPLC results showing the virtual tuber (100 g FM) means of ascorbic acid, chlorogenic acid, caffeic acid, ferulic acid, and rutin of 5 foreign cultivars analyzed 1 and 7 months after storage. Values expressed as means ± SE (n = 5). Data arranged based on alphabetical order of cultivars.

| Cultivars | 1 month | 7 months | Significance |
|---|---|---|---|
| Ascorbic acid (mg/100 g FM) | | | |
| Alwara | 8.50 ± 0.64 $^{a}$ | 3.10 ± 0.67 $^{b}$ | 0.000* |
| Bora Valley | 2.31 ± 0.87 $^{c}$ | 3.41 ± 0.66 $^{ab}$ | 0.342 |
| Gogu Valley | 1.32 ± 0.17 $^{c}$ | 1.56 ± 0.03 $^{c}$ | 0.209 |
| Gui Valley | 8.82 ± 0.61 $^{a}$ | 4.36 ± 0.08 $^{ab}$ | 0.000* |
| Purple Valley | 5.51 ± 0.96 $^{b}$ | 4.49 ± 0.04 $^{a}$ | 0.315 |
| Mean | 5.29 ± 0.45 | 3.38 ± 0.18 | |
| Chlorogenic acid (mg/100 g FM) | | | |
| Alwara | 8.74 ± 1.07 $^{c}$ | 1.37 ± 0.38 $^{c}$ | 0.000* |
| Bora Valley | 35.05 ± 1.41 $^{a}$ | 13.91 ± 0.52 $^{a}$ | 0.000* |
| Gogu Valley | 3.20 ± 0.24 $^{d}$ | 0.99 ± 0.01 $^{c}$ | 0.000* |
| Gui Valley | 3.87 ± 0.55 $^{d}$ | 0.50 ± 0.02 $^{c}$ | 0.000* |
| Purple Valley | 21.41 ± 2.04 $^{b}$ | 5.30 ± 0.04 $^{b}$ | 0.000* |
| Mean | 14.45 ± 1.64 | 4.41 ± 0.67 | |
| Caffeic acid (mg/100 g FM) | | | |
| Alwara | 0.16 ± 0.00 $^{c}$ | 0.03 ± 0.00 $^{b}$ | 0.000* |
| Bora Valley | 0.25 ± 0.02 $^{a}$ | 0.21 ± 0.04 $^{a}$ | 0.448 |
| Gogu Valley | Nil | 0.02 ± 0.00 $^{b}$ | |

TABLE 26-continued

T-test for HPLC results showing the virtual tuber (100 g FM)
means of ascorbic acid, chlorogenic acid, caffeic acid, ferulic
acid, and rutin of 5 foreign cultivars analyzed 1 and 7 months
after storage. Values expressed as means ± SE (n =
5). Data arranged based on alphabetical order of cultivars.

| Cultivars | 1 month | 7 months | Significance |
|---|---|---|---|
| Gui Valley | 0.20 ± 0.00 $^b$ | 0.05 ± 0.00 $^b$ | 0.000* |
| Purple Valley | 0.15 ± 0.01 $^c$ | traces $^b$ | 0.000* |
| Mean | 0.19 ± 0.01 | 0.06 ± 0.01 | |
| Ferulic acid (mg/100 g FM) | | | |
| Alwara | 0.07 ± 0.01 $^b$ | traces$^b$ | 0.014* |
| Bora Valley | 0.06 ± 0.02 $^{bc}$ | traces$^b$ | 0.127 |
| Gogu Valley | 0.05 ± 0.01 $^{bc}$ | traces$^b$ | 0.000* |
| Gui Valley | 0.16 ± 0.02 $^a$ | 0.01 ± 0.00 $^a$ | 0.000* |
| Purple Valley | 0.01 ± 0.00 $^c$ | Nil | |
| Mean | 0.07 ± 0.01 | 0.01 ± 0.00 | |
| Rutin (mg/100 g FM) | | | |
| Alwara | 0.97 ± 0.22 $^c$ | 0.09 ± 0.01 $^{bc}$ | 0.004* |
| Bora Valley | 2.96 ± 0.17 $^a$ | 0.19 ± 0.07 $^{ab}$ | 0.000* |
| Gogu Valley | 0.76 ± 0.04 $^c$ | 0.03 ± 0.00 $^c$ | 0.000* |
| Gui Valley | 0.69 ± 0.04 $^c$ | 0.25 ± 0.01 $^a$ | 0.000* |

TABLE 26-continued

T-test for HPLC results showing the virtual tuber (100 g FM)
means of ascorbic acid, chlorogenic acid, caffeic acid, ferulic
acid, and rutin of 5 foreign cultivars analyzed 1 and 7 months
after storage. Values expressed as means ± SE (n =
5). Data arranged based on alphabetical order of cultivars.

| Cultivars | 1 month | 7 months | Significance |
|---|---|---|---|
| Purple Valley | 2.24 ± 0.26 $^b$ | 0.15 ± 0.01 $^b$ | 0.000* |
| Mean | 1.52 ± 0.13 | 0.14 ± 0.01 | |

*T-test significance at $P \leq 0.05$; Values with same superscript in the columns are not significantly different at $P \leq 0.05$.

Significant reduction in quantity of these compounds occurred as storage progressed from 1 to 7 months. While cvs. Bora Valley, Gogu Valley, and Purple Valley retained ascorbic acid content well, cvs. Alwara and Gui Valley showed significant reduction (Table 26). Cultivar Bora Valley stored relatively well in comparison with the other foreign cultivars with no significant reduction in ascorbic acid, caffeic and ferulic acids. Among the phytochemicals analysed, ascorbic and ferulic acid content of tubers showed the least and greatest reduction, respectively, with time in storage (Table 27).

TABLE 27

Virtual tuber (100 g FM) HPLC means of 5 foreign cultivars analyzed
after 1 or 7 months storage. Values expressed as means ± SE
(n = 25). Data arranged based on alphabetical order of antioxidants.

| | 1 month (mg/100 g FM) | 7 months (mg/100 g FM) | (% reduction; from 1 to 7 months storage) |
|---|---|---|---|
| Ascorbic acid | 5.29 ± 0.45 $^a$ | 3.38 ± 0.18 $^b$ | 36.09 |
| Chlorogenic acid | 14.45 ± 1.64 $^a$ | 4.41 ± 0.67 $^b$ | 69.47 |
| Caffeic acid | 0.19 ± 0.01 $^a$ | 0.06 ± 0.01 $^b$ | 68.21 |
| Ferulic acid | 0.07 ± 0.01 $^a$ | 0.01 ± 0.00 $^b$ | 90.94 |
| Rutin | 1.52 ± 0.13 $^a$ | 0.14 ± 0.01 $^b$ | 90.63 |

Values with same superscript in the columns are not significantly different at $P \leq 0.05$.

Significant variation was found in the distribution of phytochemicals in different tuber tissue layers (Table 28). Skin showed significantly greatest polyphenolic concentration, whereas cortex and pith showed no significant differences between tissues in the concentrations of chlorogenic acid, caffeic acid, and rutin. Pith showed significantly greater concentrations of ascorbic acid. The ascorbic acid concentrations did not differ between cortex and skin. Ferulic acid was present only in the skin tissue.

TABLE 28

Tuber tissue (skin, cortex, and pith) concentrations; HPLC means of 5 foreign
cultivars over 1 and 7 months storage. Values expressed as means ± SE (n = 50).

| | Ascorbic acid (mg/g DM) | Chlorogenic acid (mg/g DM) | Caffeic acid (mg/g DM) | Ferulic acid (mg/g DM) | Rutin (mg/g DM) |
|---|---|---|---|---|---|
| Cortex | 0.17 ± 0.01 $^b$ | 0.45 ± 0.04 $^b$ | 0.01 ± 0.00 $^b$ | Nil | 0.04 ± 0.00 $^b$ |
| Pith | 0.22 ± 0.01 $^a$ | 0.40 ± 0.05 $^b$ | 0.01 ± 0.00 $^b$ | Nil | 0.05 ± 0.00 $^b$ |
| Skin | 0.16 ± 0.01 $^b$ | 2.90 ± 0.20 $^a$ | 0.16 ± 0.02 $^a$ | 0.14 ± 0.02 $^a$ | 0.44 ± 0.03 $^a$ |

At 1 month storage, ascorbic acid content was positively and negatively correlated with ferulic acid and rutin, respectively (Table 19). Chlorogenic acid was positively correlated with rutin, and with both FRAP and DPPH AOCs, and negatively correlated with ferulic acid content. Rutin was positively correlated with chlorogenic acid, FRAP and DPPH assays, and was negatively correlated with ferulic acid content.

6.4 Discussion

Figure 5:
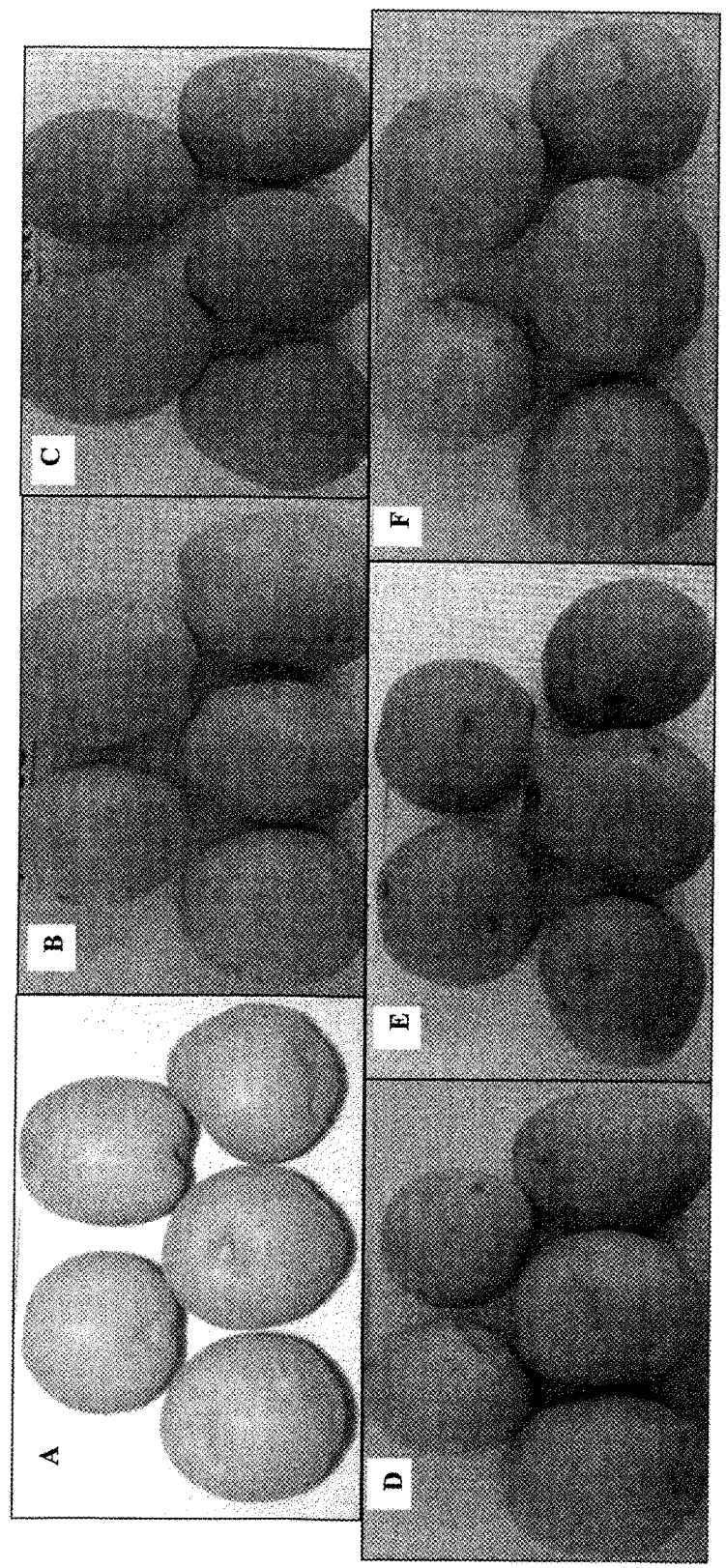
FIG. 5 shows field grown tubers of the 12 Canadian cultivars used in the studies described herein: (A) Atlantic, (B) Green Mountain, (C) Goldrush, (D) Kennebec, (E) Norland, (F) Onaway, (G) Russet Burbank, (H) Red Pontiac, (I) Sebago, (J) Shepody, (K) Superior, and (L) Yukon Gold.
Figure 5:
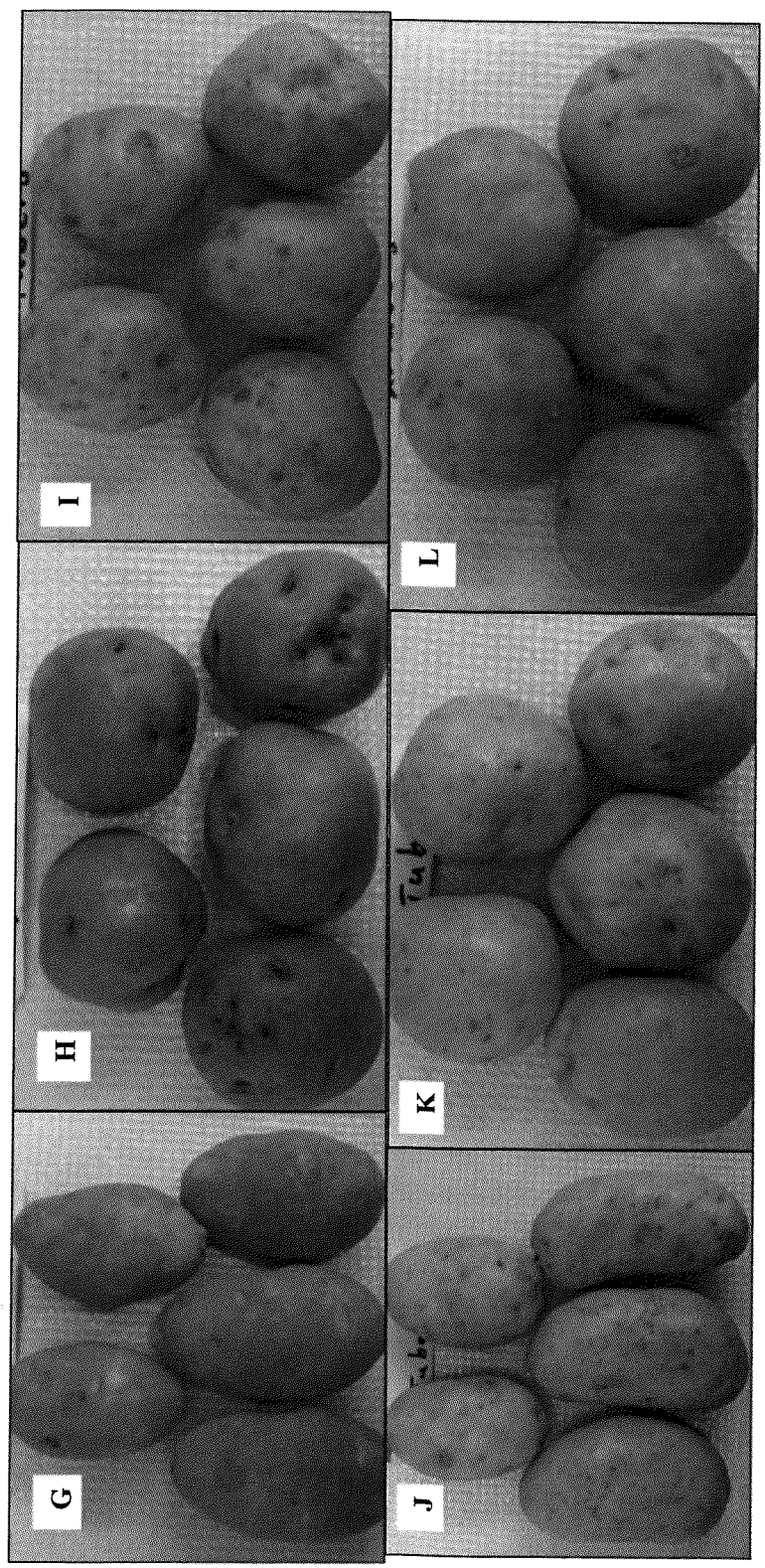

AOC of the potato tubers measured using DPPH and FRAP showed a wide range of variation both in the Canadian-grown and foreign cultivar groups. Six cultivars, Onaway, Red Pontiac, Goldrush, Kennebec, Sebago, and Shepody were consistently greater in AOC than the other six cultivars. These latter results contrast greatly to the findings of Reddivari et al. (2007) who indicated that different cultivars with similar flesh color did not show significant differences in antioxidant capacities, irrespective of skin color. Thus, Onaway with both white skin and flesh had a significantly higher AOC than the cv. Red Pontiac that has red coloured skin and white flesh (FIG. 5). Moreover, the cvs. Yukon Gold and Norland, with the lowest tuber AOC, contained yellow coloured skin and flesh, and red coloured skin and white flesh, respectively. Hence, cultivars with the greatest AOC capacity are not necessarily brightly pigmented in coloured skin or flesh. Among the foreign cultivars, Bora Valley and Purple Valley tubers with purple coloured skin and flesh showed greater AOC, while the red skinned cv. Gogu Valley (FIG. 6) had the least AOC with both DPPH and FRAP assays, which is consistent with the findings of Reddivari et al. (2007).

The DPPH and FRAP assays were highly correlated (Table 16; 17; 19; 20). Although the order of the cultivars (Canadian-grown and foreign) from greater to least tuber AOC was not exactly identical, both the tests showed more or less a similar trend in dividing them into groups with high, medium and low tuber AOC (Tables 14; 21). As the two different tests have different mechanisms, different kinds of antioxidants react differently with DPPH and FRAP reagents. The AOC of the tubers measured using FRAP analysis seemed to show greater values than DPPH analysis among the Canadian-grown cultivars, but little variation for the foreign cultivars. Lesser tuber AOC values for DPPH in comparison to FRAP may be due to the fact that DPPH does not react with free radical intermediates and oxidative chain reaction products (Nair et al., 2007) or measure the antioxidants which quench singlet oxygen (Prior et al., 2005). The six Canadian-grown cultivars Goldrush, Kennebec, Onaway, Red Pontiac, Shepody, and Sebago had the greatest tuber AOC analyzed by DPPH and FRAP at 1 month storage. Onaway, Red Pontiac, and Shepody maintained the greatest AOC at 7 months storage (Tables 14, 21), which would suggest that the latter cultivars would provide the best antioxidant capacities among the tested Canadian cultivars. Among the foreign cvs., Bora Valley had the greatest tuber AOC after 1 month storage, which was maintained as the best AOC over 7 months storage, which indicates that Bora Valley could provide one of the best antioxidant capacities among the tested foreign cultivars.

The skin tissue showed significantly greater AOC both in Canadian-grown and foreign cultivars at two storage time intervals (1 and 7 months) (Table 15). The AOC of the skin was approximately 1.5 to 2 times and 2.5 to 4 times greater than the inner flesh in Canadian and foreign cultivars respectively. This was in accordance with our second hypothesis and previous study (Li et al., 2006) which showed two-fold greater AOC of the skin than inner flesh. Significant differences in tuber AOC were not found between cortex and pith in foreign cultivars, but pith showed greater AOC compared with cortex in Canadian-grown cultivars (Table 15). In most cases, pith occupies a greater total volume of the tuber than cortex and both are significantly greater in volume than the skin.

Wide range was found in the quantities of different phenolic compounds analysed both in Canadian-grown and foreign cultivars. Interestingly, the white skinned cv. Onaway had significantly greater amount of phenolic compounds than red skinned cv. Red Pontiac (Table 23), which is not in accordance with previous studies by Brown (2005) showing that red skinned tubers contained twice the concentration of phenolic acids than white-skinned tubers. Among the foreign cultivars, purple skinned and fleshed Bora Valley and Purple Valley showed 6 to 10 times the concentration of chlorogenic acid compared with the white fleshed cv. Gogu Valley (Table 26). This latter result is indicative of a greater differential than suggested by earlier work whereby tubers with purple or red flesh contained 3 to 4 times the concentration of phenolic acids compared with white-fleshed tubers (Lewis et al. 1998). Chlorogenic acid, the major phenolic compound of potato (80% of total phenolics; Brown, 2005) accounted up to 70% (Canadian cultivars; Table 23) and 98% (foreign cultivars; Table 26) of mean summative values of the three phenolic compounds (chlorogenic acid, caffeic acid and ferulic acid) analysed in our study. The ascorbic acid content of Canadian-grown cultivars (14.39±1.35 to 43.40±3.72 mg/100 g FM) and foreign cultivars (1.32±0.17 to 8.82±0.61 mg/100 g FM) at 1 month storage showed a wide range, similar to the earlier work done on North American cultivars and breeding lines (11.5 to 29.8 mg/100 g FM; Love et al., 2003).

Cultivars with greater tuber AOC when fresh and that show better retention of tuber AOC over longer storage periods would likely provide nutritionally better antioxidant related benefits. In our study, ascorbic acid and phenolic antioxidants were reduced significantly in quantity when storage was extended from 1 to 7 months (Table 24; 27). This contrasts with a previous study (Stushnoff et al., 2008) that showed an increase in total phenolic content in highly pigments cultivars stored for 6-7 months at 5±1° C. The degree of antioxidant reduction varied with the phytonutrient compound. Generally, chlorogenic acid and caffeic acid showed the least and greatest % reduction, respectively, with storage among the 12 Canadian-grown cultivars. Among the 5 foreign cultivars, ascorbic acid and ferulic acid showed the least and greatest % reduction respectively. There was a huge difference in the % reduction of ascorbic acid with storage among Canadian-grown cultivars (80.48%) and foreign cultivars (36.09%) (Table 24; 27). This lower % reduction in foreign cultivars could be due to the presence of a greater concentration of ascorbic acid in relatively less effected inner pith tissue (Table 28) in comparison with skin tissue in the Canadian-grown cultivars (Table 25).

Both the Canadian and foreign cultivars showed significant variation in the distribution of the antioxidant phytonutrients in different tissue layers of the tubers. Skin tissue showed greater AOC than inner flesh, which could be due to greater accumulation of phenolic compounds and pigmentation molecules in the skin compared with inner flesh. Previous work showed that the skin tissues showed 0.9 to 1.6-fold greater phenolics than inner flesh in purple and red-fleshed potatoes (Reyes et al., 2005) and skin may accumulate up to 50% of the total phenolic content (Friedman, 1997). Our study showed a much greater degree of phenolic compound accumulation in the skin than expected as the major potato phenolic compound, chlorogenic acid, had up to 35 to 45 times, and 6 to 7 times greater accumulation in skin than the inner tissues in Canadian-grown cultivars (Table 25) and foreign cultivars (Table 28), respectively. Similar trend was observed for other phenolic antioxidants analysed. While skin showed greater ascorbic acid, chlorogenic acid, caffeic acid, ferulic acid, and rutin in Canadian-grown cultivars, ascorbic acid was uniquely greater in pith of the foreign cultivars.

In the Canadian-grown cultivar group, Goldrush, Kennebec, Onaway, Red Pontiac, Shepody, and Sebago had the greatest tuber AOC and are therefore recommended as healthiest nutritionally in terms of AOC for the Canadian-grown group. Among these, cv. Onaway tubers had relatively great ascorbic acid content and significantly greater chlorogenic acid, caffeic acid, and rutin content, at 1 month storage. For this reason, it is the most outstanding cultivar nutritionally of the tested cultivars, despite its lack of bright pigmentation in skin or flesh. Skin or flesh colour is not necessarily the best indicator of AOC, since of these twelve, only Red Pontiac had deeply pigmented tissue (skin) (FIG. 5). Conversely, cv. Norland tubers also had deeply pigmented red skin, but it was among the group of cultivars with the least AOC. This underlines the potential discrepancies between skin colour and AOC.

Figure 6:
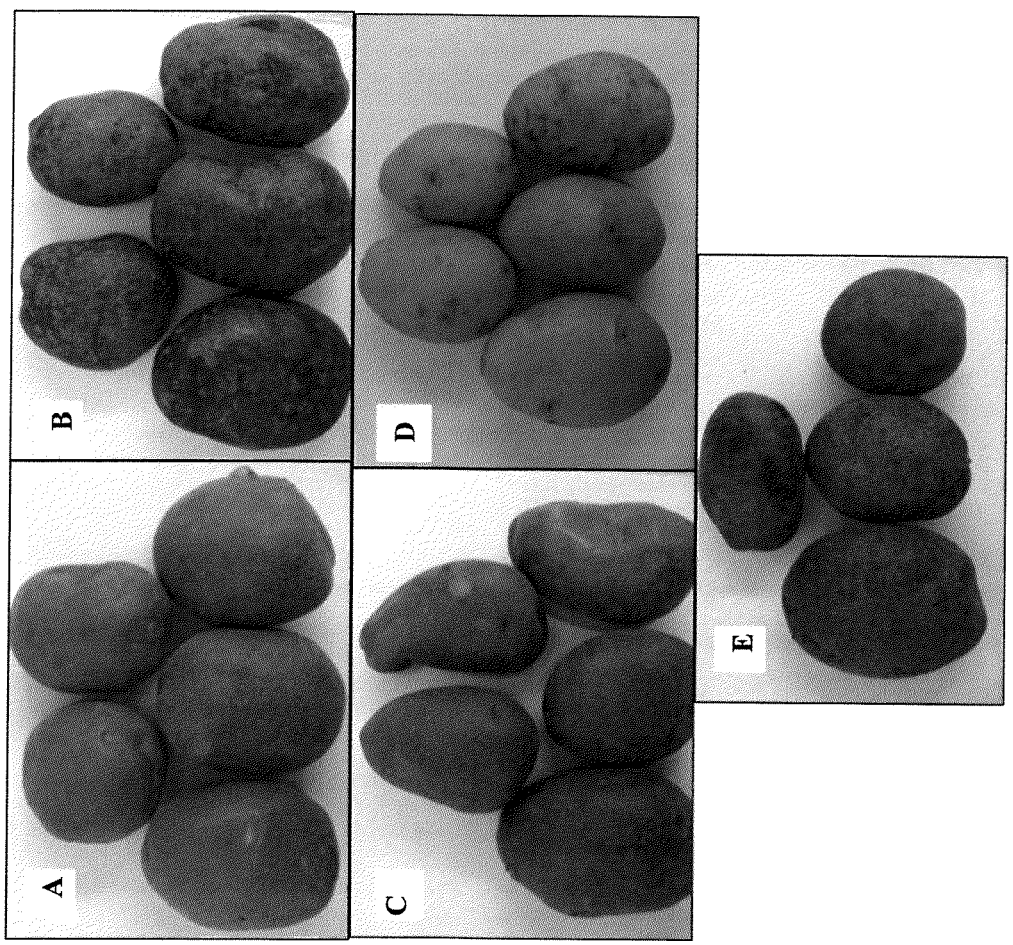
FIG. 6 shows field grown tubers of the 5 foreign cultivars used in the studies described herein: (A) Alwara, (B) Bora Valley, (C) Gogu Valley, (D) Gui Valley, and (E) Purple Valley.

In the foreign cultivar group, cvs. Bora Valley and Purple Valley were greatest for tuber AOC and had deeply purple pigmented skin and flesh (FIG. 6). Cultivar Bora Valley had approximately twice the AOC and ten times the chlorogenic acid content of red skinned and white fleshed cv. Gogu Valley, indicating that cultivars with tubers that have solidly pigmented flesh can have much greater AOC than those with tubers that have coloured skin and white flesh.

The tubers of both Canadian-grown and foreign cultivars had greater accumulation of phenolic antioxidants in the skin than inner flesh of cortex or pith. This underlines the importance of consuming potato skin. Though the skin tissue contributes to only 2% of the tuber volume (Ortiz-Medina et al., 2009), its higher accumulation of phenolic antioxidants makes the skin tissue an important dietary contributor of antioxidants. However, long-term storage (7 months) had a huge negative impact on AOC; fresh tubers should be consumed where possible.

Experiment 3: Chemical ($H_2O_2$) Hormesis Increases Antioxidant Capacity and Major Polyphenols in Potato Microtubers Abiotic stressors can be used, under controlled conditions, to promote the synthesis of phytochemicals with nutraceutical activity (Reyes and Zevallos, 2003; Zevallos, 2003). The use of potentially harmful agents under controlled conditions to obtain beneficial effects is known as hormesis. Hydrogen peroxide ($H_2O_2$) is a predominant reactive oxygen species (ROS) detected in plants, and is believed to have a dual role as an element of oxidative stress causing deleterious effects when accumulated in excess and as an inducer of protective mechanisms against oxidative stress (Kuzniak and Urbanek, 2000; Gechev et al., 2002). Mechanistically, it regulates activation of genes encoding enzymes and other proteins involved in protection from oxidative stress (Mora-Herrera and Lopez-Delgado, 2007).

Until recently (Oh et al., 2010), few studies have utilized hormetic agents to increase antioxidant compounds in growing plants pre-harvest. This shows the need to develop reliable methods to enhance health-benefiting phytochemicals in fresh fruit and vegetable produce prior to harvest or both pre- and post-harvest. The objective of this study was to develop an in vitro model system for studies of pre- and post-harvest hormesis in potato; peroxide was used as a hormetic agent for model development. More specifically, an oxidizing agent peroxide ($H_2O_2$), was applied at 0, 2, and 4 mM, to determine the effects on antioxidant capacity and specific antioxidant phytonutrients, including ascorbic acid and the major phenolic compounds, of in vitro-grown potato tubers (microtubers).

7.1 Materials and Methods

Plantlets of cvs. Onaway and Goldrush were selected for their relatively high concentrations of antioxidants in field-grown tubers. Plantlets were aseptically subcultured, using single-node cuttings, into 25×150 mm culture tubes containing 10 ml/tube MS medium (Murashige and Skoog, 1962). Medium consisted of basal salt solution and organic fraction solidified with 7 g $l^{-1}$ agar (Anachemia, Lachine, QC) adjusted to pH 5.7 before autoclaving at 121° C. for 20 min. Cultures were maintained at 22±2° C. under 85 µmol $m^{-2}s^{-1}$ cool white florescent illuminations with 16:8 h day:night cycle.

Microtubers were produced using the 2-phase layering method of Leclerc et al. (1994). In Phase I, 5 root- and tip-severed plantlets, with 5 nodes each, were layered into 150 ml of liquid medium containing MS basal salt solution and organic fraction plus 20 gm $l^{-1}$ sucrose, 0.4 mgl$^{-1}$ GA$_3$, 0.5 mgl$^{-1}$ BAP, at pH 5.7 in 500 ml plastic containers (Better Plastics, Kissimmee, Fla.). Cultures were placed into a growth chamber adjusted to 20±2° C. under 85 µmol $m^{-2}s^{-1}$ cool white florescent illumination with 16:8 h day:night cycle. Phase I promoted the vegetative growth of plantlets which was luxurious after 4 weeks. In Phase II, the residual medium was drained and replaced with 150 ml of liquid induction medium containing increased sucrose (80 gl$^{-1}$) and no growth regulators. Phase II incubation occurred at cooler temperature (15±2° C.), under reduced illumination (50 mol $m^{-2}s^{-1}$), and reversed (8:16 h) day:night cycle. Microtubers were initiated after 10-14 days, treated at 2- and 3-weeks and harvested at 4-weeks.

Based on a preliminary study, concentrations of 2 and 4 mM $H_2O_2$ and spray volume of ~6 ml were selected for hormetic treatments. Phase II plantlets of cvs. Onaway and Goldrush (at 2- and 3-weeks) were treated with three concentrations (0, 2, 4 mM) of $H_2O_2$ with 5 replicates×4 containers per replicate (20 containers per treatment). Results were analyzed for variance (ANOVA) test using General Linear Model (GLM) of Statistical Analysis System (SAS) (SAS v 9.2, 2010) (SAS Institute Inc., Cary, N.C., USA). Means were compared using Duncan's Multiple Comparison test (P≤0.05).

At harvest, microtubers of cvs. Onaway and Goldrush were weighed, and averaged from 20 separate containers. For each replicate, microtubers were pooled for analysis, for a total of 5 samples per treatment/cultivar. For each sample, microtubers were sliced into small pieces, freeze-dried (FTS Systems, NY, USA for 48 h, ground to a fine powder, and stored at −80° C. until analyzed. The antioxidant capacity of the microtuber samples was estimated using the 2,2 diphenyl-1-picryl hydrazyl (DPPH) assay of Nair et al. (2007). The total phenolic content of microtubers was measured spectrophotometrically by the Folin-Ciocalteu colorimetric method (Singleton and Rossi, 1965; Chirinos et al., 2007; Andre et al., 2009). HPLC (Varian 9012, Varian Chromatography Systems, Walnut Creek, Calif.) was used to identify and quantify ascorbic acid, three polyphenolic acids (chlorogenic acid, caffeic acid, and ferulic acid) and the flavonoid rutin.

7.2 Results

All results are shown in Table 29. Cultivar had a significant influence on microtuber yield. Cv. Goldrush had significantly greater microtuber yield (10.23 g/container); twice the yield of cv. Onaway (5.10 g/container). However, hormetic treatment, at the dosage applied, did not affect yield. This confirmed that the hormetic agent was applied at suitable dosages.

Cultivar influenced antioxidant capacity (DPPH) of microtubers. This was evidenced by cv. Goldrush controls showing 27% greater antioxidant capacity compared with cv. Onaway controls. Antioxidant capacity increased significantly in response to hormetic treatment, although cv. Goldrush microtubers showed proportionally more increase (20-26%), compared with cv. Onaway (12-14%). Cultivar Goldrush showed significantly greater antioxidant capacity in plants treated with 2 mM compared with 4 mM $H_2O_2$, both of which were significantly greater than control (by 26 and 20% increase, respectively). The microtubers of cv. Onaway also showed significantly greater antioxidant capacity in response to $H_2O_2$ treatment with 2 or 4 mM $H_2O_2$, although no significant difference occurred between these two doses.

Cultivar also influenced total polyphenolic concentration. Cv. Goldrush controls showed 59% greater total phenolic value (Folin-Ciocalteu) compared with cv. Onaway controls.

However, total polyphenolic levels were not significantly affected by hormetic treatments in either cultivar.

Peroxide treatment significantly increased the ascorbic acid content in microtubers of cv. Goldrush at both 2 and 4 mM, with an increase of 35 and 34% respectively in comparison to control. In cv. Onaway, treatment effects were not significant, though the trend was positive.

Peroxide treatment at 2 mM significantly increased microtuber chlorogenic acid content of both cultivars; Goldrush (increase of 16.8%) and Onaway (increase of 17.3%). As 4 mM treatment depressed the chlorogenic acid content in cv. Goldrush, it showed a similar effect to that of 2 mM treatment in cv. Onaway. Peroxide treatment at 2 mM showed significant depression of microtuber caffeic acid content of cv. Goldrush, but not cv. Onaway. Although the 4 mM treatment apparently depressed caffeic acid content of microtubers in cv. Onaway, these levels approached the threshold for quantification. Similarly, ferulic acid and rutin were present in trace amounts, but not accurately quantifiable at these levels.

TABLE 29

Effect of $H_2O_2$ spray treatment on microtuber mass, total antioxidant capacity (DPPH), total phenolics (Folin-Ciacalteu), ascorbic acid, chlorogenic acid, and caffeic acid.
Values are expressed as means ± SE where (n = 5).

| Cultivar | Treatment (mM $H_2O_2$) | Mass* (g) | DPPH (mg/g) | Total phenolics (mg/g) | Ascorbic acid (mg/g) | Chlorogenic acid (mg/g) | Caffeic acid (mg/g) |
|---|---|---|---|---|---|---|---|
| Goldrush | 0 | $10.23^a$ | $0.970 \pm 0.03^c$ | $6.569 \pm 0.00^a$ | $0.174 \pm 0.02^b$ | $0.480 \pm 0.01^b$ | $0.013 \pm 0.00^a$ |
|  | 2 | $10.25^a$ | $1.316 \pm 0.02^a$ | $7.076 \pm 0.01^a$ | $0.269 \pm 0.03^a$ | $0.561 \pm 0.02^a$ | $0.008 \pm 0.00^b$ |
|  | 4 | $10.26^a$ | $1.214 \pm 0.04^b$ | $6.354 \pm 0.00^a$ | $0.265 \pm 0.02^b$ | $0.460 \pm 0.02^b$ | $0.011 \pm 0.00^a$ |
| Onaway | 0 | $5.10^a$ | $0.762 \pm 0.02^b$ | $4.119 \pm 0.00^a$ | $0.147 \pm 0.01^a$ | $0.259 \pm 0.01^b$ | $0.002 \pm 0.00^a$ |
|  | 2 | $5.09^a$ | $0.862 \pm 0.02^a$ | $4.376 \pm 0.00^a$ | $0.170 \pm 0.02^a$ | $0.304 \pm 0.02^a$ | $0.002 \pm 0.00^a$ |
|  | 4 | $5.07^a$ | $0.882 \pm 0.04^a$ | $3.789 \pm 0.00^a$ | $0.164 \pm 0.02^a$ | $0.265 \pm 0.04^{ab}$ | $0.001 \pm 0.00^b$ |

Values with similar superscript are not significantly different ($P \le 0.05$)
*Mean of 20 containers per treatment 7.3 Discussion This is the first study to apply any hormetic agent to potato under defined growing conditions to investigate the antioxidant or phytonutrient impact on tubers. Significant positive effects on antioxidant capacity (DPPH) of microtubers occurred in response to the hormetic agent $H_2O_2$.

Although $H_2O_2$ treatment (2 mM) showed positive effect in chlorogenic acid content of the microtubers, it did not show an impact on total phenolic content. The total polyphenolic content was not affected by hormetic treatment, quite possibly due to an interesting inverse relationship between chlorogenic and caffeic acid, in response to hormetic stress. The increased antioxidant capacity observed in response to hormetic treatment could be explained in cv. Goldrush, by increased ascorbic acid (at both 2 and 4 mM dosage) and chlorogenic acid (at 2 mM dosage) while in cv. Onaway it is explained by increased chlorogenic acid (at 2 mM dosage). Additionally, it is also possible that the hormetic response may have also led to an increase in more potent unmeasured phenolics that exert high antioxidant activity despite the unchanged total phenolic content within the tuber.

These findings contribute to the knowledge of plant hormesis, and provide valuable information on potential use of $H_2O_2$ as an abiotic hormetic agent. To the best of our knowledge, this is the first report on the usage of $H_2O_2$ to enhance the phytonutrients (antioxidant capacity, antioxidant chemical components) of potato microtubers (or potatoes, in general). The microtuberization (layering) method appears to be a sensitive and useful model for the effect of hormesis on phytonutrient content in potato, as it was performed under controlled conditions, and can be successfully used year-round. Furthermore, "hormetic activation" of phytonutrients applied pre-harvest could be paired with post-harvest hormesis to maximize antioxidant capacity for human consumption. Hormetic studies with microtubers will need to be validated through cultural experiments on field-grown potato and the antioxidant response pattern(s) established following pre-, post- or combination of pre- and post-harvest application(s).

Experiment 4: Protective Effects of a Potato-Derived Polyphenolic Supplement in a Model of Human Lung Tissue Exposed to Environmental Pollutants Sulphur dioxide ($SO_2$) is a major and common air pollutant and has been proposed to cause severe bronchial symptoms in both humans and animals. Epidemiological evidence has linked $SO_2$ gas exposure with respiratory tract disease and lung cancer and suggests that $SO_2$ might play an important role in the initiation or exacerbation of asthma (Nyberg et al., 2000; Andersson et al., 1998). Inhaled $SO_2$ can easily be hydrated in lung tissue and the respiratory tract to generate sulfurous acid, which can subsequently form bisulfite and sulfite derivatives (1:3 M/M in neutral fluid) that are readily absorbed into blood and other bodily fluids (Shapiro, 1977). Tissue sulfite content increases in lungs and other organs in $SO_2$-exposed mice (Meng et al., 2005a) elevating lung concentrations of TNF-α and interleukin-6 (IL-6) (Meng et al., 2005b). Sodium bisulfite can also increase intracellular and extracellular production of IL-12 and IL-8 in human neutrophil cells and in human epithelial lung A549 cells (Ratthe et al., 2002; Pelletier et al., 2002). IL-8 release plays a critical role in neutrophil recruitment and activation, which is involved in asthma exacerbation (Djukanovic et al., 1990) and IL-8 reaches higher blood concentrations in asthmatic versus control subjects (Tang and Chen, 2000). Sodium sulfite has been shown to cause a dose-dependent increase in IL-8 release in human epithelial lung A549 cells, which was significantly depressed by 4 h pre-treatment with glucocorticoids (Yang et al., 2008).

Previous studies have not examined the potential protective impact of polyphenols on lung cell function and metabolism following exposure to pollutants, including sulfur dioxide or its derivatives. To test the impact of the polyphenolics against lung tissue inflammation and damage induced by exposure to environmental pollutants, the commercially available human epithelial airway culture system, MucilAir™, was used. MucilAir™ is a 3-D model of the human airway epithelium made up of primary human cells isolated from the nasal cavity, trachea, and bronchus. The 3-D format is a high-fidelity model that allows the expression of in vivo tissue complexities that traditional 2-D cultures are unable to approach, including involvement of signals from neighboring and distant cells, soluble factors, physical forces, and other extracellular matrix and microenvironment factors (Bérubé et al., 2010). Isolated cells taken from their native milieu may also display phenotypic instabilities (Khetani and Bhatia, 2006). MucilAir™ tissue cultures, which are in a homeostatic state, are as close as possible to the in vivo situation, and contain no transformed cells as MucilAir™ consists of tissues derived from primary human cells obtained from healthy people. The respiratory epithelia is composed of primary cells (basal, goblets, and ciliated cells) that form morphologically and functionally differentiated tissue equivalent to human in vivo tissue whereby typical ultra-structures that are identical to the in vivo human airway epithelium are observed, including tight junctions, cilia, basal and mucous cells. Once differentiated, MucilAir mimics the morphology and function of the native human airway epithelia, including beating cilia, active ion transport, and tight junctions. The mucocilliary clearance is also fully functional. As MucilAir™ has a similar microanatomy to that of natural respiratory tract tissue, MucilAir™ tissues react to pro-inflammatory mediators (i.e., TNF-α with resulting IL-8 secretion) and a wide variety of environmental toxicants in a physiological manner, including a strong capacity for regeneration after mechanical or chemical injuries. The MucilAir™ system is particularly useful for screening, testing, and validating therapeutic candidates designed to protect against toxin-associated respiratory disorders. The above model contrasts with immortalized cell lines that fail to reproduce the in vivo physiological characteristics of the corresponding human lung tissues.

8.1 Experimental Design:

The polyphenolic composition in terms of the concentration and profile of major polyphenolics identified in the potato extract was re-constituted with pure compounds (Table 30) and tested for protective effects against deleterious effects of exposure to $SO_2$ derivatives in MucilAir™ lung tissue cultures in terms of cellular viability, proliferation, inflammation and reactive oxygen species production. Differentiated MucilAir™ lung tissue cultures were exposed for 4 h in a dose response manner with freshly prepared solutions of 0.01, 0.1 and 1.0 mM $SO_2$ derivatives ($SO_2D$) (bisulfite and sulfite, 1:3 ratio) that were premixed in medium. MucilAir™ lung tissue cultures were also pre-incubated for 4 h prior to exposure to 0.1 mM $SO_2D$ with 20 µM of a polyphenolic mixture that was composed of polyphenolics present at the identical concentrations of chlorogenic acid, caffeic acid, ferulic acid and rutin measured in the cv. Onaway potato extract (Table 30). After 4 h exposure to $SO_2D$ in the presence and absence of polyphenols, cells were harvested to test for cell viability (trypan blue exclusion), cytokine IL-8 release into the medium, and production of reactive oxygen species (ROS).

TABLE 30

Composition of major polyphenolic compounds observed in Onaway potato extract. The same composition using synthetic polyphenolic compounds was tested for protective effects against $SO_2D$ exposure in the MucilAir ™ lung tissue cultures.

| Polyphenol | µM (µmol/L) |
|---|---|
| Chlorogenic acid | 228 |
| Caffeic | 40 |
| Ferulic | 29 |
| Rutin | 10.9 |

8.2 Materials and Methods:

Extract preparation: The powdered extract from Onaway potato cultivar was generated according to the following protocol. The potatoes were soaked, hand washed, and pat-dried. The potatoes were then cut into ⅜" sections and steeped in liquid nitrogen, placed in re-sealable bags and then stored at −80° C. (overnight). The potatoes were then lyophilized for 3-4 days and then resealed in bags for storage at −80° C. Under UV-filtered lights, 35 g of lyophilized potato was ground to a powder with a coffee grinder. Thereafter, 10 g was steeped for 24 hours in 100 ml of 90% ethanol at 0° C. and sealed under nitrogen. The ethanol solution was filtered under vacuum using a Whatman #1 filter paper and the filtrate was concentrated to a final total volume of 30 ml using a Buchi rotory evaporator under UV filtered lights under vacuum and a water cooled condenser with a 50% rotation in a 40° C. water bath. The ethanol concentrate was diluted to a 1:5 ratio with double distilled water in conical tubes and frozen overnight at −80° C. and then subjected to lyophilization to make the final potato extract powder. These freeze-dried potato extract samples were used for further chemical, biochemical, and cell culture characterization after the potato extracts were subjected to in vitro digestion.

HPLC analysis: HPLC analysis was based on the method developed by Shakya and Navarre (2006). Initially, samples (50 mg of freeze-dried powder) were extracted in 0.9 mL of extraction buffer (50% MeOH, 2.5% metaphosphoric acid, 1 mM EDTA) in a 2 mL screw cap tube. Samples were vortexed for 30 sec and centrifuged at 11,070×g for 15 min at 4° C. The supernatant was transferred to a 1.5 mL glass vial. The remaining pellet was re-extracted with 0.6 mL of extraction buffer and centrifuged. The supernatants were combined and concentrated in a Speed Vac (Thermo Savant SC 210A, Waltham, Mass.). The concentrated samples were solubilised with 500 mL of extraction buffer and filtered using 0.45 mm membrane filters (Durapore, PVDF) into 1 mL HPLC glass vials. Samples were kept chilled at all times and shielded from bright light. Samples were analyzed using a Varian HPLC system with a quaternary gradient pump, a single wavelength UV/VIS detector, and an autosampler with refrigerated sample compartment (Varian Canada Inc, Mississauga, ON). Samples were eluted using an Onyx reverse-phase HPLC column (100×4.5 mm) (Phenomenex, Netherlands), a solvent flow rate of 2 mL/min and a solvent gradient of 0-1 min 100% buffer A (10 mM formic acid, pH 3.5, with $NH_4OH$), 1-5 min 0-30% buffer B (100% methanol with 5 mM ammonium formate), 5-6.5 min 40-0% buffer B, 6.5-8.5 min 70-100% buffer B. The phenolic acids in the samples were analyzed qualitatively and quantitatively using standards.

Cell Culture: Normal MucilAir™ lung cells were obtained from Epithelix, Switzerland, EU. The cells were attached onto inserts inside 24-well plates and transferred immediately to a new plate containing FBS free media and maintained at 37° C. with 5% $CO_2$ for two weeks according to Epithelix protocol, which involved with changing the 500 µL media every 48 h with FBS free media supplied from Epithelix. MucilAir™ lung cells were treated in the absence or presence of 0.01, 0.1 and 1.0 mM of $SO_2D$ for 4 h or cells were pre-incubated at 37° C. with 5% $CO_2$ for 4 h with polyphenols at 20 µM and exposed to 0.1 mM of $SO_2D$. After 4 h exposure to $SO_2D$, supernatants from each well were collected and stored at −80° C. for measurement of IL-8 release into the medium. Apical and basal sides of inserts were washed with pre-warmed PBS twice, which were collected for any dissociated cells. The effects of $SO_2D$ and polyphenolic treatments on MucilAir™ lung cellular viability was determined by the trypan blue exclusion assay. Cells were trypsinized with 500 µL pre-warmed trypsin solution and incubated at 37° C. for 15 min. 500 µL pre-warmed fresh media was added to dissociate the cells and to which was added the above collected PBS wash solution for cell counting. The total numbers of cells, viable cells and dead cells were counted with a Beckman commercial VI cell counter that adds trypan blue solution and cell suspension media for automatic cell counting.

Reactive oxygen species (ROS) characterization: Intracellular ROS were quantified using a fluorescent probe, 5-(and 6-)carboxy-2'7'-dichlorodihydrofluorescein diacetate (carboxy-$H_2$DCF-DA) (Wang and Joseph, 1999). Carboxy-$H_2$DCF-DA diffuses through the cell membrane and then is enzymatically hydrolyzed by intracellular esterases to form non-fluorescent derivative, carboxy-$H_2$DCF that is oxidized by reactive oxygen species to form fluorescent DCF by ROS. The DCF fluorescence intensity is proportional to intracellular reactive oxygen species production. A carboxy-$H_2$DCF-DA (Molecular Probes, Carlsbad, Calif., USA) stock solution was prepared and cells were incubated for 30 min at 37° C. with 5 µM of carboxy-$H_2$DCF-DA solution in FBS free media and fluorescence was measured with fluorescence plate reader using KC4 data reduction software at excitation of 485 nm and emission at 530 nm.

IL-8 quantitation: IL-8 levels were quantified using a commercial enzyme immunoassay (BD OptEIA Set for human IL-8, BD Biosciences) according to manufacturer's instructions. An immunoassay flat-bottomed 96-well plate was coated with primary capture antibody and incubated at 4° C. overnight. The plate was washed the next day and blocked with assay diluent for 1 h at room temperature. After addition of samples and standards into the wells, the plates were incubated at room temperature for 2 h. After washing, detection antibody and avidin-horseradish peroxidase were added into the wells and incubated at room temperature for 1 h. After the plates were washed, substrate was added and the plate was incubated at room temperature for 30 min. A 2 N HCl stop solution was added to each well and the plates were read at 450 nm. Quantification was performed by calibration against the standards.

8.3 Results:

Cell viability was unaffected by 4 hour exposure to the 0.1M dose of $SO_2$ derivatives bisulfite and sulfite ($SO_2D$) or by prior exposure to the 20 µM polyphenol mixture as the percentage of cell viability of $SO_2D$- and polyphenol-treated was similar to control values (Table 31), which indicates that the exposure of lung cells to $SO_2D$ and polyphenols was not cytotoxic.

TABLE 31

Total cell numbers and cell viability as assessed by trypan blue exclusion

| Treatment | Total cells ($\times 10^6$ per ml) | Viable cells ($\times 10^6$ per ml) | Viability (%) |
| --- | --- | --- | --- |
| Control | 0.65 | 0.46 | 70.7 |
| 0.1 mM $SO_2D$ | 0.66 | 0.47 | 69.8 |
| Polyphenols (20 µM) + 0.1 mM $SO_2D$ | 0.87 | 0.67 | 76.2 |

MucilAir™ lung tissue cultures were loaded with carboxy-$H_2$DCF-DA, which is a ROS-sensitive membrane permeable probe that is rapidly deacetylated intracellularly and fluoresces green upon oxidation by ROS, thus reflecting intracellular oxidative stress. Fluorescence analysis 4 hours after treatment with the 0.1 mM dose of $SO_2D$ showed an increase in oxidized probe, reflecting induction of intracellular oxidative stress (Table 32). In contrast, 4 hour pre-treatment with the 20 µM polyphenol mixture prior to the $SO_2D$ exposure was not associated with increased oxidative stress following 4 hour exposure to $SO_2D$.

TABLE 32

Intracellular ROS measured via the free radical-sensitive probe carboxy-$H_2$DCF-DA

| Treatment | Control | 0.01 mM $SO_2D$ | 0.1 mM $SO_2D$ | Polyphenols (20 µM) + 0.1 mM $SO_2D$ |
| --- | --- | --- | --- | --- |
| 4 h after $SO_2D$ treatment | 6347 | 4490 | 14969 | 2506 |

Figure 7:
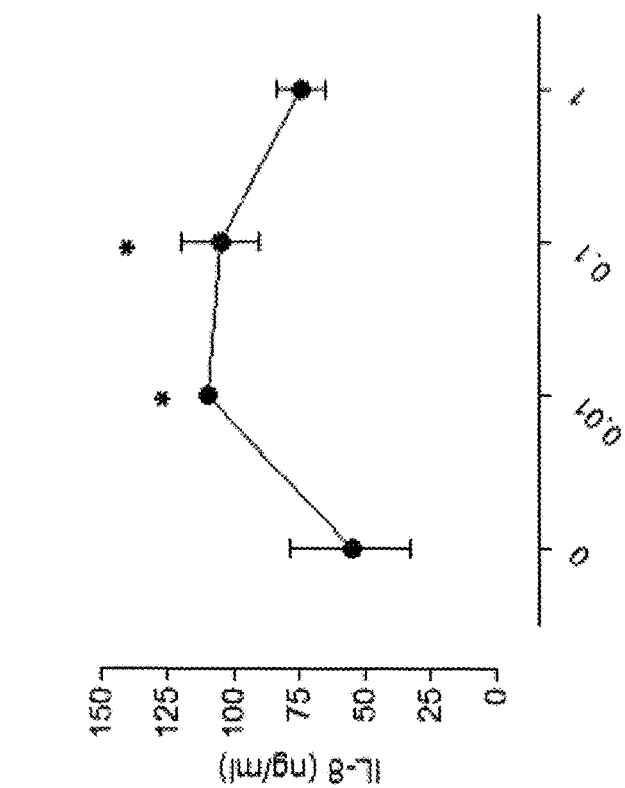
FIG. 7 shows effects of $SO_2$ derivatives ($SO_2D$) (bisulfite and sulfite, 1:3 ratio) on IL-8 production in MucilAir™ lung tissue cultures (n=3) that were incubated for 4 h with buffer or the increasing concentrations of $SO_2D$. The concentration of IL-8 in the supernatant was measured by enzyme-linked immunosorbant assay (ELISA). Results are mean±SD; *p<0.05 (0 µM vs. 0.01 µM and 0 µM vs. 0.01 µM) as tested via one-way analysis of variance and post-hoc Tukey's multiple comparison test.

A significant (p<0.05) increase in the release of IL-8 into the culture media was observed after 4 h of incubation at the non-cytotoxic doses of 0.01 mM and 0.1 mM $SO_2D$ (FIG. 7). The increased release of IL-8 at non-cytotoxic doses of $SO_2D$ is pertinent since suppression of IL-8 release due to cytotoxicity can occur following exposure to environmental toxicants (Newby et al., 2000).

Figure 8:
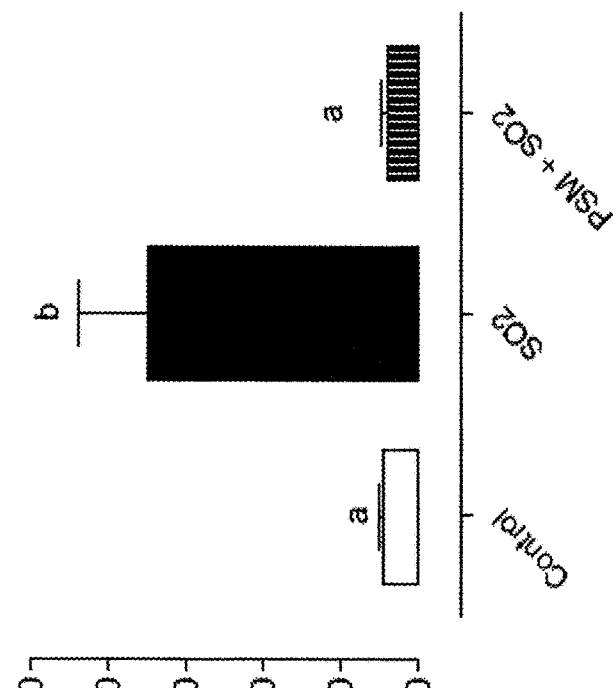
FIG. 8 shows effects of polyphenolic synthetic mixture (PSM) (20 µM) on induction of IL-8 protein production (ng/ml medium) by 0.1 mM $SO_2$ derivatives ($SO_2D$) (bisulfite and sulfite, 1:3 ratio) in MucilAir™ lung tissue cultures (n=3) that were incubated for 4 h with buffer or the increasing concentrations of $SO_2D$. The concentration of IL-8 in the supernatant was measured by enzyme-linked immunosorbant assay (ELISA). Results are mean±SD; columns not sharing the same letter are significantly different (p<0.05) as tested via one-way analysis of variance and post-hoc Tukey's multiple comparison test.
Figure 9:
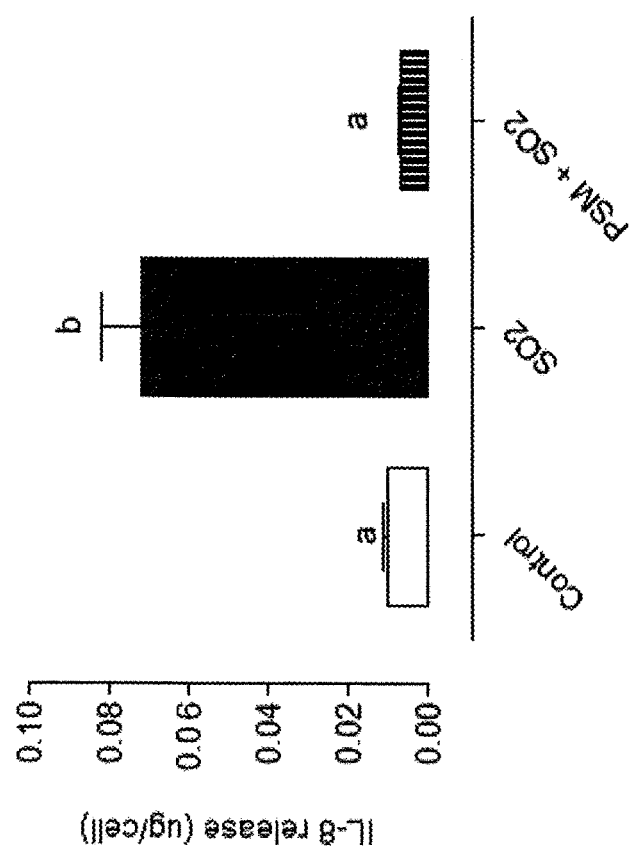
FIG. 9 shows effects of polyphenolic synthetic mixture (PSM) (20 µM) on induction of IL-8 protein production (µg/cell) by 0.1 mM $SO_2$ derivatives ($SO_2D$) (bisulfite and sulfite, 1:3 ratio) in MucilAir™ lung tissue cultures (n=3) that were incubated for 4 h with buffer or the increasing concentrations of $SO_2D$. The concentration of IL-8 in the supernatant was measured by enzyme-linked immunosorbant assay (ELISA). Results are mean±SD; columns not sharing the same letter are significantly different (p<0.05) as tested via one-way analysis of variance and post-hoc Tukey's multiple comparison test.

When expressed either in terms of IL-8 released into the medium or IL-8 release on a per cell basis, 4 h pre-treatment of MucilAir™ lung tissue cultures with the 20 µM polyphenol mixture (PSM) resulted in a significant (p<0.05) reduction in IL-8 release, resulting in IL-8 levels that were comparable to those seen in control cultures (IL-8 release/volume, FIG. 8; IL-8 release/cell, FIG. 9).

The efficacy of the very low polyphenolic concentration of 20 µM used in terms of inhibition of IL-8 release in the present study is unexpected relative to a previous dose ranging study that tested the anti-inflammatory effects of 250-2000 µM chlorogenic acid or caffeic acid in terms of suppressing TNF-α or hydrogen peroxide-mediated induction of IL-8 release in Caco-2 cell cultures (Zhao et al., 2008). The latter study demonstrated that concentrations of chlorogenic acid or caffeic acid ranging from 250 to 1000 µM were required to suppress significantly IL-8 release depending on the stimulus of TNF-α or hydrogen peroxide used. Moreover, doses of 2000 µM of chlorogenic acid or caffeic acid were needed to suppress IL-8 secretion to levels seen in control cultures (Zhao et al., 2008). The potency of the tested polyphenol mixture in the present study (i.e., effective doses of only 15 and 2.6 µM of chlorogenic and caffeic acid, respectively) towards inhibition of IL-8 release to the levels observed in control cell cultures can be attributed to the unique combination of chlorogenic acid, caffeic acid, ferulic acid and rutin as found in cv. Onaway potato extracts, which are likely exerting synergistic effects on IL-8 release. The 20 µM dose is roughly equivalent to glucocorticoid doses used to suppress IL-8 release in human epithelial lung A549 cells following 4 h glucocorticoid pre-treatment prior to sodium sulfite exposure (Yang et al., 2008). The underlying suppression mechanism of IL-8 secretion of the polyphenolic mixture is unclear, but some studies have suggested that chlorogenic acid up-regulates cellular antioxidative enzymes and suppresses ROS-mediated nuclear factor-κB (NF-κB), activator protein-1 (AP-1) and mitogen-activated protein kinases (MAPK) activation as observed in A549 human lung cancer cells (Feng et al., 2009), which is in concert with the potent suppression of intracellular ROS production observed in the present study (Table 32).

An LC-MS analysis was performed on the potato extract in order to further characterize and/or readjust said extract as a standardized product. Said analysis demonstrated the presence of glycoalkaloids α-chaconine and α-solanine in said extract which in combination with the polyphenolic phytochemicals have anti-inflammatory activities (Kenny et al., Life Sciences 92 (2013) 775-782).

Experiment 5: Decrease of Body Weight Gain and Adiposity and Improved Glucose Control in a Mouse Model of Diet-Induced Obesity 9.1. Materials and Methods
9.1.1 Preparation of the Polyphenol-Rich Potato Extract on a Larger Scale Potatoes in general are known to contain a variety of polyphenolic compounds, such as chlorogenic acid (CGA), caffeic acid, ferulic acid (FA) Friedman, J. Agric. Food Chem. 1997, 45, 1523-1540), and rutin. Among these, CGA makes up the majority of the polyphenols in the potato tuber. Cultivars Onaway and Russet Burbank, which consistently showed high amounts of these four polyphenols, were selected as the source of PRPE (prepared by POS Bio-Sciences, SK, Canada). Briefly, 20 kg of potato were diced, freeze-dried and extracted by agitation in 200 L of a 90% (v/v) aqueous ethanol solution for 1 h at room temperature. The extract was separated from the solids by centrifugation at 1,076×g for 10 min. The extract was then concentrated under vacuum at 40-50° C. until ~15 L remained and the ethanol concentration was <10% as measured using a hydrometer. If not, water was added back during evaporation, as needed, until the desired final ethanol concentration was attained. Finally, the extract was freeze-dried to generate powdered PRPE. The PRPE powder was stored at 80° C. until utilization for the feeding trials.

9.1.2. Animal Feeding Study

C57BL/6J mice (8 wk old) were purchased from Jackson Laboratory (Bar Harbor, Me.). The mice were acclimated to vivarium conditions for 2 wk before the start of the controlled diet period. Mice were housed in separate groups and fed a high fat diet (HFD, 60% fat; D12492, Research Diets, New Brunswick, N.J.) or the HFD supplemented with pure CGA (8, 40 and 200 mg/kg HFD), or FA (20, 100 and 500 mg/kg HFD), or with PRPE to a final concentration of 1.93% (w/w) (Batch 1) or 3.5% (w/w) (Batch 2), or a synthetic mixture (SM) of pure CGA and FA at a concentration that matched the amounts of CGA and FA supplied by the PRPE. The PRPE dosages in Batches 1 and 2 corresponded to 200 mg CGA and 6 mg FA per kg of HFD. Batch 2, as compared to Batch 1, provided a higher content of caffeic acid (22.5 mg versus 13.5 mg/kg HFD) and rutin (13.0 versus 9.7 mg/kg HFD). The diets were fed to mice ad libitum for 10 wk (n=5 per group per sex in the SM and PRPE feeding trials; n=3-5 per group per sex in the pure CGA and FA dosing trials). The use of animals in this study was institutionally approved (AUP #5886) by the Animal Care Committee of McGill University in accordance with the policies of the Canadian Council on Animal Care.

9.1.3. Analysis of Mice

Food intake, respirometry, and activity rate were measured over a 24 h period using the Panlab Oxylet System (Barcelona, Spain) in Week-9 of the controlled diet period using PRPE Batch 2. Glucose tolerance of mice was tested by intraperitoneal glucose tolerance test (IPGTT) for mice treated with PRPE Batch 1 and by oral glucose tolerance test (OGTT) for mice treated with PRPE Batch 2. Glucose (2 g/kg body weight) was administered by injection into the peritoneal cavity for IPGTT and by oral gavage for OGTT. Blood samples were taken from the saphenous vein for blood glucose analysis using the OneTouch UltraMini glucometer (LifeScan Inc., Milpitas, Calif., USA). At the end of the diet study, mice were anesthetized with isoflurane and exsanguinated by cardiac puncture. Plasma from mice treated with HFD, HFD+PRPE, and HFD+SM in Batch 2 was separated and analyzed for insulin, ghrelin, gastric inhibitory peptide (GIP), glucagon-like peptide (GLP)-1, glucagon, leptin, plasminogen activator inhibitor (PAI)-1, and resistin using a Bio-Plex Pro Mouse Diabetes 8-Plex Assay kit (Bio-Rad Laboratories, ON), according to the manufacturer's instructions.

9.1.4. Statistical Analysis

Differences between groups were evaluated by one-way analysis of variance with post hoc Holm-Sidak method, Tukey's multiple comparisons test or by Student's t-test where appropriate (GraphPad Prism, La Jolla, Calif.). The differences were considered significant when $P<0.05$.

9.2. Results and Discussion
9.2.1 Chemical Characteristics of PRPE

Two independent batches of PRPE were prepared from two crops of potatoes grown in two different seasons. In both batches, the polyphenols accounted for ~1.1% of the weight of the final powdered extract and were enriched by ~30-fold by weight compared to the raw potato. The amount of protein (28% w/w of PRPE) contributed by the extracts to the HFD at the concentration (2-3.5% w/w) used in this study did not significantly alter the macronutrient composition of the diet.

More specifically, initially the second of the two batches of PRPE that were produced did not have the same effect as the first batch. Batch 1 was generated from cv. Onaway harvested in the 2011 growing season, which had a polyphenolic content of 10.4 mg/g CGA, 0.7 mg/g caffeic acid, 0.3 mg/g FA, and 0.5 mg/g rutin per g dry mass. The initial second batch was generated from cv. Onaway from the following year, the 2012 growing season, Only after the second batch was supplemented with phenolic components from another potato extract, a functional Batch 2. Batch 2 consisted of a 1.38:1 combination of cv. Onaway and cv. Russet Burbank extracts. Batch 2 used the cv. Onaway extract generated from the 2012 growing season (3.51 mg/g CGA, 0.59 mg/g caffeic acid, 0.2 mg/g FA, and 0.27 mg/g rutin per g dry mass) and cv. Russet Burbank extract (8.75 mg/g CGA, 0.71 mg/g caffeic acid, 0.134 mg/g FA, and 0.51 mg/g rutin per g dry mass).

9.2.2. Effect of CGA and FA on Body Weight Gain and Blood Glucose Control of DIO Mice CGA accounted for the bulk of polyphenols in the PRPE (87.7% and 82.8% of total polyphenols in PRPE Batches 1 and 2, respectively). Therefore, to determine the appropriate dose of PRPE to use in the animal feeding trials, we first examined the effect of supplementing the HFD with pure CGA or FA on body weight gain and on blood glucose concentration in C57BL/6J mice with diet-induced obesity. The doses that were selected for analysis ranged from 8-200 mg/kg diet for CGA and 20-500 mg/kg diet for FA. These concentrations span the range of doses used in previously reported animal feeding trials. The body weights of male mice fed the HFD diet without and with supplementation are shown in Table 33.

TABLE 33

Change in body weight and blood glucose

| Group | Body weight gain (g) | Fasting blood glucose (mmol/L) |
|---|---|---|
| Males | | |
| HFD | 18.5 ± 4.4$^{a,b,c}$ | 8.2 ± 1.0$^a$ |
| HFD + 1X CGA | 22.4 ± 0.8$^b$ | 7.3 ± 1.5$^a$ |
| HFD + 5X CGA | 18.2 ± 4.1$^{a,b,c}$ | 7.3 ± 0.3$^a$ |
| HFD + 25X CGA | 8.8 ± 5.3$^c$ | 6.2 ± 0.6$^a$ |
| HFD + 1X FA | 12.4 ± 3.7$^{a,b,c}$ | 5.2 ± 0.6$^b$ |
| HFD + 5X FA | 10.8 ± 2.3$^{a,b,c}$ | 6.1 ± 1.2$^a$ |
| HFD + 25X FA | 11.0 ± 6.5$^{a,b,c}$ | 5.4 ± 0.2$^b$ |
| Females | | |
| HFD | 11.1 ± 4.3$^a$ | 4.4 ± 0.9$^a$ |
| HFD + 1X CGA | 9.7 ± 4.9$^a$ | 6.6 ± 0.1$^a$ |
| HFD + 5X CGA | 7.6 ± 4.1$^a$ | 5.9 ± 0.7$^a$ |
| HFD + 25X CGA | 9.8 ± 3.4$^a$ | 5.4 ± 2.3$^a$ |
| HFD + 1X FA | 9.7 ± 3.4$^a$ | 3.8 ± 0.6$^a$ |
| HFD + 5X FA | 6.3 ± 1.2$^a$ | 6.9 ± 1.1$^a$ |
| HFD + 25X FA | 8.8 ± 5.0$^a$ | 4.7 ± 1.6$^a$ |

1x CGA corresponds to 8 mg/kg HFD;
1x FA corresponds to 20 mg/kg HFD
data shown are mean ± SD (n = 3-5)

For each sex, values displayed in each column that do not share the same superscripts are significantly different (P<0.05) according to one-way ANOVA Surprisingly, pure CGA did not affect body weight gain of male mice although it tended to decrease body weight gain at the highest concentration used (200 mg/kg). In female mice, CGA tended to decrease body weights at lower concentrations but had no statistically significant effect even at the highest concentration used. It has been reported that feeding male mice a high fat diet supplemented with pure CGA at 1 g/kg diet had no effect on body weight gain and caused glucose intolerance as well as enhanced lipid accumulation in the liver (Mubarak et al., J. Agric. Food Chem. (2013) 61, 4371-4378). Our results also suggest a sex dimorphic response to dietary CGA supplementation. Biological sex is now recognized as a significant modifier of metabolic response (Sugiyama and Agellon, Biochem. Cell Biol. (2012) 90, 124-141), and emphasizes the importance of including both sexes in studies that assess efficacy and mechanism of action of biologically active agents. Similarly, FA at the dosages used was also ineffective in suppressing body weight gain in both sexes even at the concentration of 500 mg/kg diet (Table 33). The findings illustrate that the ratio of CGA and FA is an important parameter that dictates the potency of the synthetic mixture. All the mice showed blood glucose concentrations within the normal range at the end of the HFD feeding period (Table 33).

9.2.3. Bioactivity of the PRPE Extract

Figure 10:
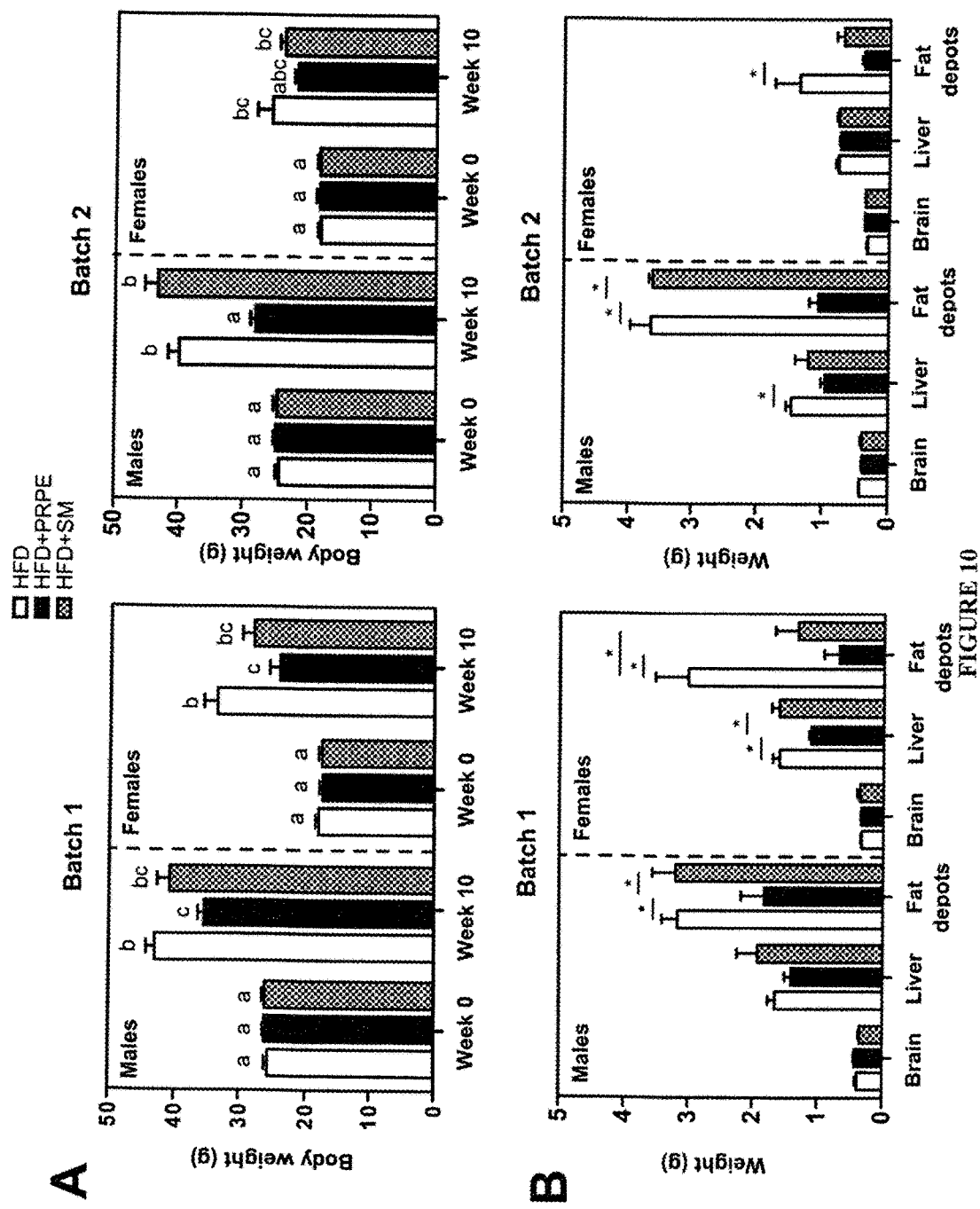
FIG. 10 shows effects of PRPE supplementation on body weight gain and adiposity in DIO mice. (A) Body weights at the start (Week-0) and end (Week-10) of the controlled diet period. (B) Wet weights of organs selected for analysis. The value shown for fat depots is the sum of abdominal, renal and gonadal fat pads. The individual weights of the fat depots are shown in Table 2. Values shown are mean±SD (n=5 per group). *Bars in the same graphs that are not sharing the same letter superscripts are statistically different (P<0.05).

Based on our results obtained with pure CGA and FA (Table 33), concentrations of 19 and 35 g PRPE per kg of HFD were formulated, using Batches 1 and 2 respectively to supply CGA and FA at a ratio of CGA at 200 mg/kg and FA at 6 mg/kg of HFD, for testing in DIO mice. The effect of the HFD diet without and with PRPE or SM supplementation on body weight of mice after 10 wk on the diet is shown in FIG. 10A. Said ratio between CGA and FA of 200:6 was important for the effect of the polyphenolics within the extract. This 33.3:1 weight ratio of CGA (354.0951 g mol-1) to FA (194.0579 g mol-1) comes to a molar ratio of 18.25 moles chlorogenic acid to 1 mole ferulic acid. Ranges of proportions of 25:1 to 35:1 (weight per weight) or 13.7:1 to 19.2:1 (mol per mol) between CGA and FA resulted in the desired bioactivity.

The two different batches of PRPE attenuated body weight gain in both male and female mice. In males, body weight gain was reduced by 47.1% for PRPE Batch 1 and 79.3% for PRPE Batch 2 whereas in females the reduction was 57.2% for PRPE Batch 1 and 54.3% for PRPE Batch 2 (FIG. 10A). These results demonstrate a relatively greater potency in body weight reduction than previously reported for anthocyanin-rich extracts of the purple-fleshed cv. Bora Valley that showed less than 10% body weight reduction in high fat-fed rats (Yoon et al., J. Ethnopharmacol. 2008, 118, 396-404), which could be due to the greater concentration of anti-obesity compounds and/or differential response of the animal model. The corresponding SM, which delivered the equivalent amounts of pure CGA and FA found in the respective PRPEs, showed variable results in males, attenuating body weight gain by 15.7% for SM 1 but enhancing body weight gain by 19.7% for SM (FIG. 10A). Females showed a reduction in body weight gain of 32.2% for SM 1 and 27.1% for SM 2. The body weight gain of males and females fed the SM diet did not differ significantly from the body weight gain of the respective HFD diet controls. The reduction in body weight gain in both sexes of mice treated with PRPE was mostly due to decreased fat deposition (FIG. 10B) in all fat depots examined (Table 34).

TABLE 34

Weights of fat depots

| Group | Abdominal fat (g) | Renal fat (g) | Gonadal fat (g) |
|---|---|---|---|
| PRPE Batch 1 | | | |
| Male HFD | 0.72 ± 0.23$^a$ | 0.47 ± 0.27$^a$ | 1.97 ± 0.39$^a$ |
| Male HFD + PRPE | 0.23 ± 0.13$^b$ | 0.27 ± 0.14$^a$ | 1.32 ± 0.55$^a$ |
| Male HFD + SM | 0.83 ± 0.35$^a$ | 0.55 ± 0.28$^a$ | 1.81 ± 0.30$^a$ |
| Female HFD | 0.62 ± 0.28$^a$ | 0.79 ± 0.45$^a$ | 1.57 ± 0.56$^a$ |
| Female HFD + PRPE | 0.11 ± 0.07$^b$ | 0.15 ± 0.12$^b$ | 0.42 ± 0.35$^b$ |
| Female HFD + SM | 0.17 ± 0.11$^b$ | 0.30 ± 0.19$^b$ | 0.83 ± 0.55$^b$ |
| PRPE Batch 2 | | | |
| Male HFD | 0.84 ± 0.31$^a$ | 0.67 ± 0.17$^a$ | 2.13 ± 0.33$^a$ |
| Male HFD + PRPE | 0.30 ± 0.27$^a$ | 0.14 ± 0.10$^b$ | 0.68 ± 0.15$^b$ |
| Male HFD + SM | 0.85 ± 0.31$^a$ | 0.63 ± 0.06$^a$ | 2.11 ± 0.36$^a$ |
| Female HFD | 0.34 ± 0.15$^a$ | 0.29 ± 0.29$^a$ | 0.71 ± 0.42$^a$ |
| Female HFD + PRPE | 0.16 ± 0.05$^a$ | 0.04 ± 0.02$^a$ | 0.18 ± 0.07$^b$ |
| Female HFD + SM | 0.18 ± 0.11$^a$ | 0.15 ± 0.12$^a$ | 0.35 ± 0.11$^{a,b}$ |

Data shown are mean ± SD (n = 5).

For each sex treated with the same batch of PRPE, values displayed in one column with different superscripts are significantly different (P<0.05) according to one-way ANOVA.

Liver weight was also lower in both male and female mice treated with PRPE Batch 1 but only in male mice treated with PRPE Batch 2 (FIG. 10B). The absence of response by female mice with regard to liver weight was not expected, but could be due to the higher caffeic acid and rutin content of PRPE Batch 2. On the other hand, brain weights of male or female mice were comparable among all the feeding groups.

In both PRPE feeding trials, supplementation of the HFD with a synthetic mixture of CGA and FA with amounts matching those provided by each of the PRPE batches was consistently inferior to supplementing with the PRPE itself. Furthermore, the synthetic mixture had a variable effect on body weight gain of male mice in both trials, although it did decrease body weight gain in female mice but less effectively than PRPE. These results suggest that the constellation of compounds including caffeic acid and rutin present in the PRPE serve to increase its bioactivity of reducing body weight gain and controlling blood glucose as compared to the simple combination of purified CGA and FA. Thus, the most preferred potato extract contains CGA and FA in a weight per weight proportion ranging between 25:1 and 35:1 in synergy with caffeic and rutin. To be more specific, a potato extract containing caffeic acid and rutin but not containing CGA and FA in the proportion ranging between 25:1 and 35:1 does not have the desired bioactivity of reducing body weight gain and controlling blood glucose.

Figure 11:
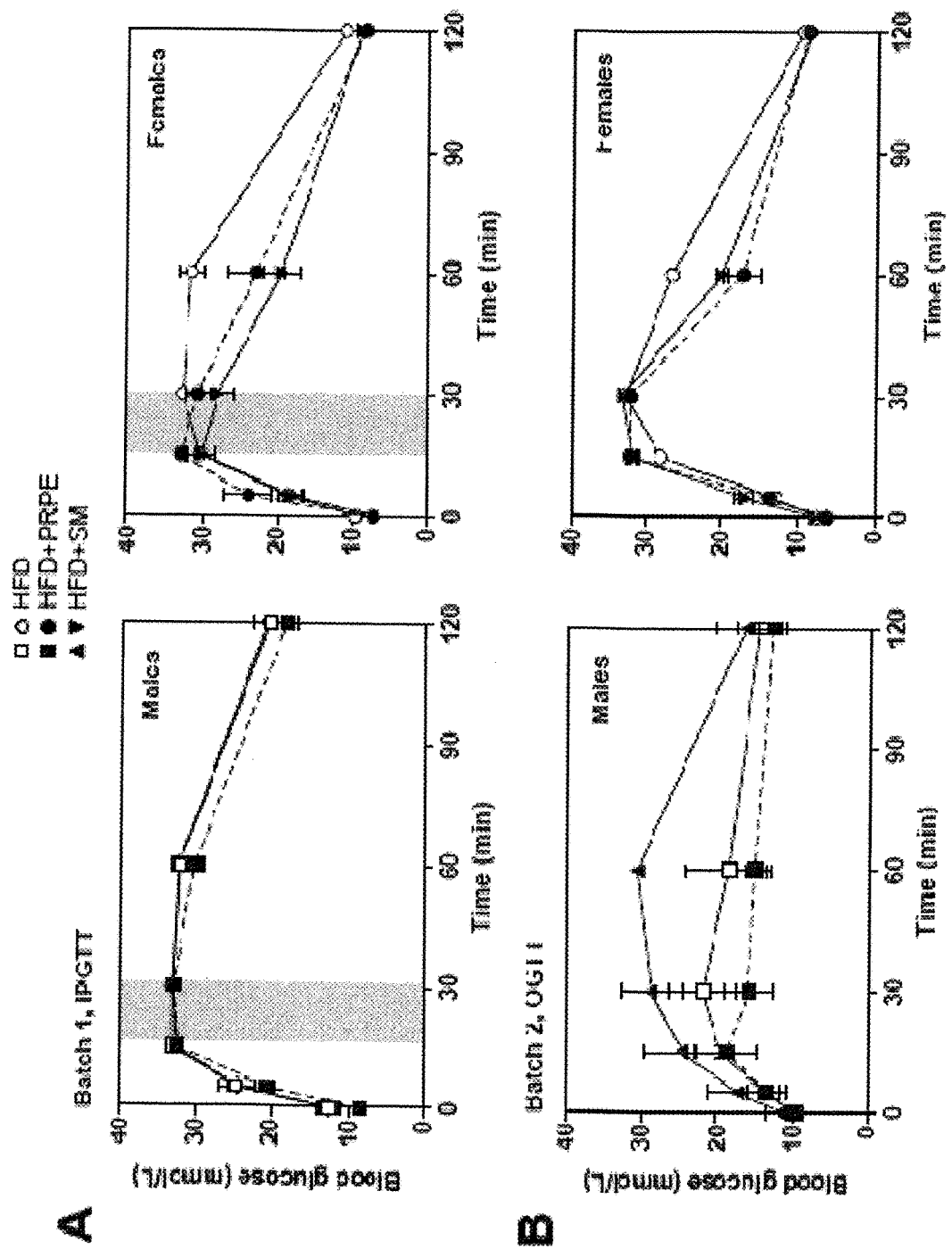
FIG. 11 shows glucose tolerance tests. (A) Glucose was administered by injection into the peritoneal cavity (see Materials and Methods). The shaded area represents a time interval where the rise in glucose concentration was greater than the maximum level detected by the glucometer. (B) Glucose was administered by oral gavage (see Materials and methods). The solid lines represent values for HFD and HFD+SM. The dashed lines represent values for HFD+PRPE.

The HFD used in this study is also known to induce glucose intolerance in C57BL/6J mice (Wang, et al., Methods Mol. Biol. 2012, 821, 421-433). Therefore, blood glucose control was examined by IPGTT in the PRPE Batch 1 trial. In male mice, the HFD diet caused a rise in glucose concentration at 15 and 30 min after glucose treatment that was beyond the detection limit of the glucometer (33 mmol/L) (FIG. 11A). The same result was observed for SM 1 at the 15 min time point. However, the maximum rise in blood glucose concentration in male mice treated with PRPE-Batch 1 was <33 mmol/L. In female mice, blood glucose control was better in mice treated with either PRPE Batch 1 or SM 1 than in female mice receiving the HFD alone (FIG. 11A).

Since differences in the degree of hyperglycemia exhibited by mice in response to different methods of glucose challenge (i.e., IPGTT vs. OGTT) have been noted previously (Andrikopoulos, et al., Am. J. Physiol. Endocrinol. Metab. 2008, 295, E1323-1332), OGTT was used to assess glucose response in the PRPE Batch 2 trial. In this test, the rise in blood glucose concentration after glucose challenge to levels beyond the detection limit of the glucometer did not occur (FIG. 11B). Surprisingly, male mice treated with SM 2 showed significantly higher blood glucose concentrations than male mice receiving the HFD alone, whereas mice treated with PRPE Batch 2 showed better glucose control. In females, mice treated with PRPE Batch 2 and SM 2 showed comparable responses, which was better than mice receiving the HFD alone (FIG. 11B). Thus, both male and female mice receiving the PRPE consistently exhibited improved blood glucose control after 10 wk on the HFD compared to mice fed the HFD alone. Plasma from Batch 2 mice analyzed for insulin showed levels below the limit of detection for all male mice treated with HFD+PRPE. Only two animals from the HFD+SM group had detectable levels of insulin (88.78 pg/ml±9.79), whereas all animals fed HFD alone exhibited much higher levels (527.42 pg/ml±230.5) (Table 35).

None of the females had plasma insulin levels above the limit of detection. The higher plasma levels of insulin seen in the male mice fed HFD alone are commonly seen with obesity and are considered a biomarker of insulin resistance (Tabak et al. Lancet 2012, 379, 2279-2290). As insulin resistance drives increased nutrient uptake into adipocytes, this could enhance the development of adiposity in the male mice. The inhibition of the high insulin levels by PRPE supplementation in male mice could have contributed to its anti-obesity effects.

TABLE 35

| | Plasma concentrations of diabetes and obesity markers | | | | | | | |
|---|---|---|---|---|---|---|---|---|
| Group | Insulin (pg/mL) | Glucagon (pg/mL) | Ghrelin (ng/mL) | GIP (pg/ml) | GLP-I (pg/mL) | Leptin (pg/mL) | PAI-I (pg/mL) | Resistin (ng/mL) |
| Males | | | | | | | | |
| HFD | 527 ± 230 | 36.58 ± 1.87$^a$ | 13.76 ± 1.84$^a$ | 27.86 ± 9.73$^a$ | 2.31 ± 1.07$^a$ | 4611 ± 1010$^a$ | 414 ± 35$^a$ | 20.85 ± 3.85$^a$ |
| HFD + PRPE | <22** | 42.85 ± 2.34$^a$ | 83.61 ± 8.02$^b$ | 47.00 ± 3.60$^a$ | 7.05 ± 2.50$^a$ | 491 ± 298$^b$ | 395 ± 77$^a$ | 23.68 ± 1.55$^a$ |
| HFD + SM | 89 ± 9 | 56.44 ± 23.41$^a$ | 31.15 ± 10.00$^b$ | 26.61 ± 7.07$^a$ | 3.80 ± 1.34$^a$ | 4666 ± 1024a | 440 ± 115$^a$ | 17.94 ± 3.59$^a$ |
| Females | | | | | | | | |
| HFD | <22** | 55.91 ± 9.64$^a$ | 40.49 ± 9.07$^a$ | 63.06 ± 11.53$^a$ | 3.79 ± 0.59$^a$ | 1264 ± 490$^a$ | 443 ± 64$^a$ | 27.97 ± 3.77$^a$ |
| HFD + PRPE | <22** | 42.04 ± 2.54$^a$ | 63.02 ± 6.01$^{a,b}$ | 10.14 ± 2.37$^b$ | 4.23 ± 0.43$^a$ | 106 ± 33$^b$ | 352 ± 76$^a$ | 13.94 ± 2.36$^b$ |
| HFD + SM | ND | 65.26 ± 9.98$^a$ | 71.86 ± 4.71$^b$ | 42.27 ± 8.98$^{a,b}$ | 2.94 ± 0.31$^a$ | 307 ± 110$^{a,b}$ | 424 ± 60$^a$ | 22.38 ± 3.22$^{a,b}$ |

Data shown are mean ± SE (n = 4-5); ND, not detected by the assay.
**Limit of detection of the Bio-Plex Pro Mouse Diabetes 8-Plex assay.
For each sex, values displayed in one column with different superscripts are significantly different ($P < 0.05$) according to one-way ANOVA (multiple comparisons by Holm-Sidak method or Tukey test where appropriate).

Figure 12:
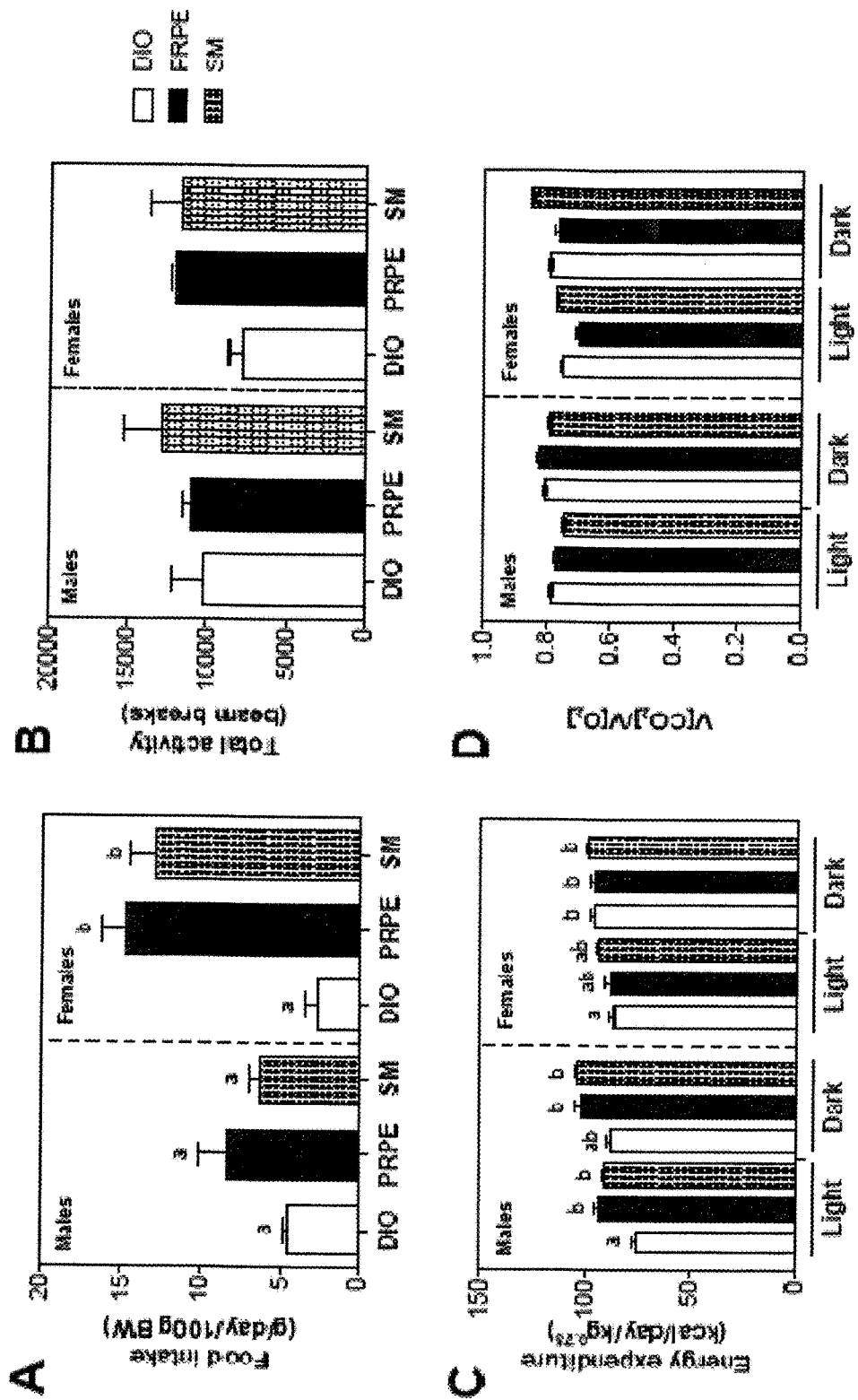
FIG. 12 shows food intake, respirometry and activity level. (A) Food intake, (B) Activity level, (C) Energy expenditure, and (D) respiratory quotient. *Bars in the same panel that are not sharing the same letter superscripts are statistically different (P<0.05).
Figure 13:
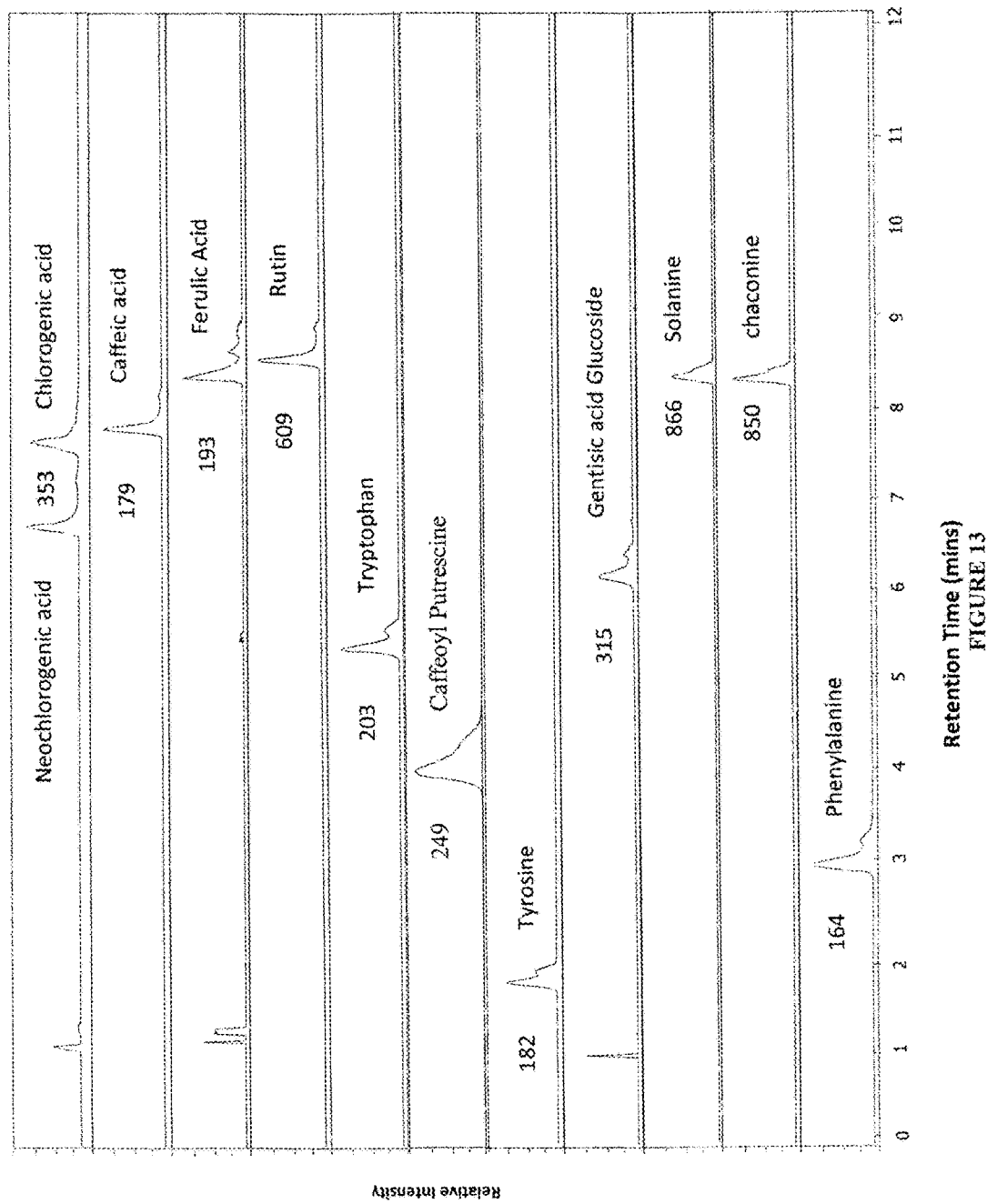
FIG. 13 shows the identified compounds in Onaway-Russet Burbank potato extract as analyzed by liquid chromatography time-of-flight mass spectrometry (LC-TOF-MS).

Analysis of food intake revealed that both male and female mice receiving the PRPE or SM consumed more food than mice receiving the HFD alone, and this effect was more pronounced in female mice (Table 36 and FIG. 12). The activity rate was not altered by PRPE or SM supplementation (Table 36 and FIG. 12). In contrast, both the PRPE and SM increased energy expenditure in male mice compared to the HFD group whereas no change was observed for female mice (FIG. 12). The respiratory quotients observed were consistent with the use of mixed substrates as energy sources (FIG. 12). The differing responses exhibited by male and female mice suggest that attenuation of weight gain occurs via different mechanisms in the two sexes, and requires further study.

TABLE 36

Metabolic parameters

| Group | Food intake (g/100 bw/24 h) | Activity (beam breaks/24 h) |
|---|---|---|
| PRPE Batch 1 | | |
| Male HFD | 4.6 ± 0.3$^a$ | 10247 ± 3428$^a$ |
| Male HFD + PRPE | 8.4 ± 2.9$^b$ | 11019 ± 776$^a$ |
| Male HFD + SM | 6.3 ± 1.1$^b$ | 12948 ± 4049$^a$ |
| Female HFD | 2.7 ± 1.2$^a$ | 7829 ± 1531$^a$ |
| Female HFD + PRPE | 14.7 ± 2.8$^c$ | 12071 ± 554$^a$ |
| Female HFD + SM | 12.9 ± 2.7$^c$ | 11664 ± 4102$^a$ |
| PRPE Batch 2 | | |
| Male HFD | 8.9 ± 3.9$^a$ | 12802 ± 1372$^a$ |
| Male HFD + PRPE | 12.4 ± 3.0$^a$ | 12083 ± 2718$^a$ |
| Male HFD + SM | 9.1 ± 5.0$^a$ | 10728 ± 1337$^a$ |
| Female HFD | 11.3 ± 3.3$^a$ | 12125 ± 1146$^a$ |
| Female HFD + PRPE | 18.9 ± 4.2$^b$ | 9517 ± 1358$^a$ |
| Female HFD + SM | 16.8 ± 0.3$^a$ | 8973 ± 2028$^a$ |

Activity is expressed as total number of beam breaks in the x, y and z axes.
Data shown are mean ± SD (n = 3-4).
Values displayed in one column with different superscripts for each batch are significantly different (P < 0.05) according to one-way ANOVA.

Male mice supplemented with PRPE or SM exhibited significantly higher plasma ghrelin levels than males fed HFD (Table 35). Similarly, female mice supplemented with SM had significantly higher plasma ghrelin levels than those fed HFD alone and female mice fed HFD+PRPE tended to have higher plasma ghrelin levels than HFD-fed females. Previous work has noted that plasma ghrelin levels are reduced in obese rodents fed high fat diets (Gomez et al. Regul. Pept. 2012, 173, 60-63). The higher plasma ghrelin levels in male mice supplemented with PRPE or SM could be related to their relatively lower plasma insulin levels relative to the HFD-fed mice as hyperinsulinemia is inversely correlated with plasma ghrelin in rodents and humans (McCowen et al. J. Endocrinol. 2002, 175, R7-11; McLaughlin et al., J. Clin. Endocrinol. Metab. 2004, 89, 1630-1635). The relatively higher plasma ghrelin levels seen in the PRPE and SM female mice could be partly due to their improved glucose control since elevated systemic glucose levels appear to play a role in the inhibitory effects of HFD and obesity on ghrelin production and secretion. Plasma leptin levels were lowest among mice of both sexes supplemented with PRPE (Table 35). The lowered plasma leptin levels in the PRPE-fed mice can be related to their lower fat mass and body weight as there is a positive correlation of plasma leptin levels with percent body fat in mice (Frederich et al., Nat. Med. 1995, 1, 1311-1314) and in humans (Considine et al., N. Engl. J. Med. 1996, 334, 292-295). Female mice supplemented with PRPE exhibited significantly lower levels of plasma resistin and GIP than those fed HFD alone (Table 35). The lowered plasma GIP levels could partly account for the anti-obesity efficacy of PRPE in females as GIP supports efficient storage of dietary fat and elevated plasma levels of GIP are linked with high dietary fat-induced obesity (Miyawaki et al. Nat. Med. 2002, 8, 738-742). The lower levels of resistin in the female mice given the PRPE could have contributed to their improved glucose tolerance as elevated plasma resistin levels from high fat diet feeding in mice is associated with hyperinsulinemia (Yang et al., Diabetol. Metab. Syndr. 2012, 4, 32). There were no significant differences in plasma resistin or GIP among males. There were no significant differences between groups in terms of glucagon, GLP-1, or PAI-1 (Table 36).

Thus a standardized preparation of a polyphenol-enriched extract from cv. Onaway and Russet Burbank stem tubers that contains amounts of CGA and FA in a proportion ranging from 25:1 to 35:1 on a weight per weight basis as well as caffeic acid and rutin This standardized extract shows potent activity in attenuating weight gain, adiposity, hyperinsulinemia, and glucose intolerance in the DIO mouse model. The present study also found that the biomarkers of obesity and insulin resistance were affected differently by PRPE supplementation in male and female mice, indicating sex differences in the mechanisms of action. In addition, the PRPE showed greater bioactivity compared to that exhibited by a synthetic mixture of pure CGA and FA in amounts equivalent to that found in the PRPE, indicating that additional bioactive components present in PRPE, or the combination of nutrients and other phytochemicals that make up the PRPE as a whole, are needed in order to express its full beneficial effects on metabolism. The calculated effective PRPE dose, which is equivalent to 35.4 g of PRPE (Batch 2) per 70 kg person, contains the polyphenol content provided by approximately 43 servings of fresh potatoes based on the standard 148 g serving size. Hence, it is not practical to obtain the amount of polyphenols needed for the anti-obesity effects by ingesting the potato tuber itself and so the use of the PRPE as a dietary supplement is a more realistic approach. Failure of the individual polyphenols, or a mixture of pure polyphenols, to match the anti-obesity and improved glucose control of the PRPE is consistent with findings seen with other fruit and vegetable extracts. For example, polyphenolic concentrates of cranberry juice showed improved bioactivity relative to isolated anthocyanin and proanthocyanidin fractions in terms of antiproliferative activity on HepG2 human liver cancer cells [35]. In humans, a dose of 1 to 2 g per day of pure resveratrol, a polyphenol originally identified in the skin of red grapes, is needed to show improvements in postprandial plasma glucose concentrations and insulin sensitivity [36]. Moreover, the feeding of pure polyphenols may have detrimental effects, such as in the case of pure CGA at 1 g/kg diet which exacerbated the negative effects of the high fat diet [24].

In conclusion, the results of the present study suggest that an extract of white-fleshed potatoes that contains a rich content of a specified mixture of polyphenols may be useful for improving blood glucose control and can control body weight gain, primarily by suppressing fat deposition. It remains to be described by which mechanisms the potato extract regulates these processes that also appear to be affected by sex differences.

The invention will be further described by the following numbered paragraphs:

1. A composition enriched in ferulic acid, caffeic acid, chlorogenic acids, anthocyanins, ascorbic acid, and rutin, or an isomer or derivative thereof having antioxidant and/or anti-inflammatory activity, said composition comprising an extract or fraction of at least one potato cultivar wherein the extract or fraction comprises said chlorogenic acids and said ferulic acid in a proportion ranging between 25:1 and 35:1 by weight.
2. The composition of paragraph 1, wherein said composition comprises an extract or fraction of at least one of an Onaway, Bora Valley or Purple Valley potato cultivar, or a combination thereof.
3. The composition of paragraph 2, wherein said composition further comprises an extract or fraction of a Russet Burbank potato cultivar.

4. The composition of any one of paragraphs 1 to 3, prepared as an oral supplement, a functional food, or a food/feed additive.
5. The composition of any one of paragraphs 1 to 4, wherein said extract or fraction is derived from the potato skin, pith, or cortex, or a combination thereof.
6. The composition of any one of paragraphs 1 to 5, formulated as a pharmaceutical or nutraceutical composition and further comprising one or more acceptable carriers or excipients.
7. The composition of any one of paragraphs 1 to 6, wherein the extract or fraction is obtained from a fresh source of the at least one potato cultivar.
8. The composition of any one of paragraphs 1 to 7, wherein the extract or fraction is obtained from the source of the at least one potato cultivar within 2 months post-harvest.
9. The composition of any one of paragraphs 1 to 7, wherein the extract or fraction is obtained from the source of the at least one potato cultivar within 1 month post-harvest.
10. The composition of any one of paragraphs 1 to 9, wherein the source of at least one potato cultivar has been treated to induce hormesis before or after harvesting, or during the storage interval of the source of the potato cultivar, and the treatment increases the level of one or more of ferulic acid, caffeic acid, chlorogenic acids, anthocyanins, ascorbic acid, rutin, or isomers or derivatives thereof having antioxidant and/or anti-inflammatory activity in the source of the potato cultivar.
11. The composition of paragraph 10, wherein the treatment to induce hormesis is selected from the group consisting of: treatment with relatively high or low temperature air or water; treatment with an excess of one or more minerals; partial to severe starvation of one or more minerals; treatment with ionizing radiation, treatment with one or more oxidizing agents; wounding; and treatment with one or more phytochemicals.
12. The composition of any one of paragraphs 1 to 11, wherein said composition comprises an extract or fraction of at least an Onaway potato cultivar.
13. The composition of paragraph 12, wherein said composition further comprises an extract or fraction of a Russet Burbank potato cultivar.
14. A functional food comprising a food enriched with a composition according to any one of paragraphs 1 to 13.
15. A method of treating or preventing an oxidative stress-related disease or disorder, said method comprising administering a composition as defined in any one of paragraphs 1 to 13 to a subject in need thereof in an amount sufficient to ameliorate or prevent said oxidative stress-related disease or disorder.
16. A method of treating or preventing a chronic inflammatory disease or disorder, said method comprising administering a composition as defined in any one of paragraphs 1 to 13 to a subject in need thereof in an amount sufficient to ameliorate or prevent said chronic inflammatory disease or disorder.
17. The method of paragraph 16, wherein said chronic inflammatory disease or disorder is Inflammatory Bowel Disease.
18. A method of improving insulin sensitivity and/or glucose tolerance, said method comprising administering a composition as defined in any one of paragraphs 1 to 13 to a subject in need thereof in an amount sufficient to improve insulin sensitivity and/or glucose tolerance in said subject.
19. A method of reducing adiposity, said method comprising administering a composition as defined in any one of paragraphs 1 to 13 to a subject in need thereof in an amount sufficient to reduce adiposity in said subject.
20. A method of treating or preventing diabetes and/or obesity, said method comprising administering a composition as defined in any one of paragraphs 1 to 13 to a subject in need thereof in an amount sufficient to ameliorate or prevent the diabetes and/or obesity in said subject.
21. The method of paragraph 20, wherein said diabetes is diabetes mellitus (type-1 or type-2).
22. A method of treating a chronic inflammatory disease that is aggravated by particulates or pollution, or both, said method comprising administering a composition as defined in any one of paragraphs 1 to 13 to a subject in need thereof in an amount sufficient to ameliorate said chronic inflammatory disease in said subject.
23. The method according to paragraph 22, wherein said chronic inflammatory disease that is aggravated by particulates or pollution, or both, is selected from asthma, complications related to heart disease, hypertension and respiratory disorders.
24. A method of treating or protecting against an environmentally induced health disorder, said method comprising administering a composition as defined in any one of paragraphs 1 to 13 to a subject in need thereof in an amount sufficient to ameliorate or protect against said environmentally induced health disorder in said subject.
25. A method of treating or protecting against the development of immune dysregulation and lower IQ associated with chronic pollutant exposures, said method comprising administering a composition as defined in any one of paragraphs 1 to 13 to a subject in need thereof in an amount sufficient to ameliorate said chronic inflammatory disease in said subject.
26. A process for preparing a composition enriched in ferulic acid, caffeic acid, chlorogenic acid, rutin, ascorbic acid and anthocyanins, or an isomer or derivative thereof having antioxidant and/or anti-inflammatory activity, said process comprising:
  obtaining a source of at least one potato cultivar,
  treating the source of at least one potato cultivar to induce hormesis before or after harvesting or during storage of the source of the potato cultivar, or combinations thereof, wherein the treatment increases the level of one or more of ferulic acid, caffeic acid, chlorogenic acids, anthocyanins, ascorbic acid, rutin, or isomers or derivatives thereof having antioxidant and/or anti-inflammatory activity in the source of at least one potato cultivar.
  extracting or fractionating said source of at least at least one potato cultivar within 2 months post-harvest, and
  formulating said extracted or fractionated material into a composition enriched in ferulic acid, caffeic acid, chlorogenic acid, rutin, ascorbic acid, and anthocyanins, or an isomer or derivative thereof wherein the extract or fraction comprises said chlorogenic acids and said ferulic acid in a proportion ranging between 25:1 and 35:1 by weight.
27. The process of paragraph 26, wherein the source of at least one potato cultivar further comprises a source of at least one of an Onaway, Bora Valley or Purple Valley potato cultivar or a combination thereof.
28. The composition of paragraph 27, wherein the source of at least one potato cultivar further comprises a source of a Russet Burbank potato cultivar.
29. The process of paragraph 26, wherein the source of the potato cultivar is a fresh source.

30. The process of paragraph 26, wherein the source of the potato cultivar is obtained and/or extracted or fractionated within 1 month post-harvest.

31. The process of paragraph 26, wherein the treatment to induce hormesis is selected from the group consisting of: treatment with relatively high or low temperature air or water; treatment with an excess of one or more minerals; partial to severe starvation of one or more minerals; treatment with ionizing radiation; treatment with one or more oxidizing agents; wounding; and treatment with one or more phytochemicals.

One or more currently preferred embodiments have been described by way of example. It will be apparent to persons skilled in the art that a number of variations and modifications can be made without departing from the scope of the invention as defined in the claims.

REFERENCES CITED

1. Benzie I F F and Strain J J (1996) Analytical Biochemistry 239:70-76.
2. Lachman, J. et al., Food Chem (2009) 114:836-843.
3. Lang S 1992. http://www.geocities.com/willboyne/nosurrender/PeelsBad.html.
4. Lewis C E, J R L Walker, and J E Lancaster (1999) J Sci Food Agric 79:311-316.
5. Lim et al., 2008. USA The healthy and functional foods for the obesity patients using purple-colored potato.) EP1949792
6. Manach C et al., Am J Clin Nutr (2004) 79:727-47.
7. McCune L M and Johns T, J. Ethnopharmacol. (2002) 82:197-205
8. Morton L W et al., Clin Exp Pharmacol Physiol (2000) 27:152-59.
9. Ortiz-Medina E Sosle V Raghavan V. and Donnelly D J (2009) J Food Science 74:S177-S181.
10. Paynter et al., Am J Epid (2006) 164(11):1075-1084.
11. Remington's Pharmaceutical Sciences (1985) Mack Publishing Co., Easton, Pa.,
12. Rodriguez-Saona L et al., J Food Sci (1999) 64:445-450.
13. Rommens, Caius (2008) High Level Antioxidant-Containing Foods. Jan. 10, 2008; PCT/US2007/015437
14. Romieu I, Castro-Giner F, Kunzli N, Sunyer J., Eur Respir J (2008) 31(1):179-97.
15. Sellappan S, Akoh C C, Krewer G., J Agricultural Food Chem (2002) 50:2432-2438.
16. Selloum et al., Experimental and Toxicologic Pathology (2003) 54(4):313-318.
17. Shakya R, Navarre D A, J Agric Food Chem (2006) 54:5253-5260.
18. Shimoda et al. BMC Complementary and Alternative Medicine (2006), 6:1-9.
19. Srinivasan M et al., J Clin Biochem Nutr. (2007) 40(2): 92-100.
20. Umamaheswari S, Prince P S M, Acta Pol Pharm (2007) 64:53-61.
21. Wolfgang et al. PNAS (2006) 103:7282-7287.
22. Zhao J et al., J Agric Food Chem (1994) 42: 2570-73.
23. Andre, C. M., Oufir, M., Guignard, C., Hoffmann, L., Hausman, J. F., Evers, D., and Larondelle, Y., Journal of Agricultural and Food Chemistry (2007) 55:10839-10849.
24. Andre, C. M., Oufir, M., Hoffmann, L., Hausman, J. F., Rogez, H., Larondelle, Y., and Evers, D., Journal of Food Composition and Analysis (2009) 22:517-524.
25. Brown, C., American Journal of Potato Research (2005) 82:163-172.
26. Chirinos, R., Rogez, H., Campos, D., Pedreschi, R., and Larondelle, Y., Separation and Purification Technology (2007) 55:217-225.
27. Friedman, M., Journal of Agricultural and Food Chemistry (1997) 45:1523-1540.
28. Gechev, T., Gadjev, I., Van Breusegem, F., Inze, D., Dukiandjiev, S., Toneva, V., and Minkov, I., Cellular and Molecular Life Sciences (2002) 59:708-714.
29. Gopal, J. and Minocha, J. L., Plant Breeding (1997) 116:293-295.
30. Kuzniak, E. and Urbanek, H., Acta Physiologiae Plantarum (2000) 22:195-203.
31. Leclerc, Y., Donnelly, D. J., and Seabrook, J. E. A., Plant Cell Tissue and Organ Culture (1994) 37:113-120.
32. Lewis, C. E., Walker, J. R. L., Lancaster, J. E., and Conner, A. J., Australian Journal of Plant Physiology (1998a) 25:915-922.
33. Lewis, C. E., Walker, J. R. L., Lancaster, J. E., and Sutton, K. H., L. Journal of the Science of Food and Agriculture (1998b) 77:45-57.
34. Li. K., Park E., Lee H., Khu D., Love S L., and Lim H., Journal of the Korean Society for Horticultural Science (2006) 47:126-131.
35. Love S L, T Salaiz, B Shafii, W J Price, A R Mosley, and R E Thornton Acta Horticulturae (2003) 619:87-93.
36. Mora-Herrera, M. and López-Delgado, H., American Journal of Potato Research (2007) 84:467-475.
37. Murashige, T. and Skoog, F., Physiologia Plantarum (1962) 15:473-497.
38. Nollet, L. M. L., HPLC. In: Food analysis by HPLC. Siouffi, A. M. (ed). Marcel Dekker, New York. (1992) Pp 1-52.
39. Oh, M.-M., Carey, E. E., and Rajashekar, C. B., Journal of the American Society for Horticultural Sciences, (2010) 135:223-229.
40. Prior, R. L., Wu, X., and Schaich, K., Journal of Agricultural and Food Chemistry (2005) 53:4290-4302.
41. Reddivari, L., Hale, A., and Miller, J., American Journal of Potato Research (2007) 84:275-282.
42. Reyes, L. F. and Cisneros-Zevallos, L., Journal of Agricultural and Food Chemistry (2003) 51:5296-5300.
43. Reyes, L., Miller, J., and Cisneros-Zevallos, L., American Journal of Potato Research (2005) 82:271-277.
44. Singleton, V. L. and Rossi, J. A., Jr., American Journal of Enology and Viticulture (1965) 16:144-158.
45. Stushnoff, C., Holm, D., Thompson, M., Jiang, W., Thompson, H., Joyce, N., and Wilson, P., American Journal of Potato Research (2008) 85:267-276.
46. Andersson, E., Nilsson, T., Persson, B., Wingren, G., and K. Toren, Scand. J. Work Environ. Health (1998) 24:12-17.
47. Andre, C. M., Oufir, M., Hoffmann, L., Hausman, J. F., Rogez, H., Larondelle, Y., and Evers, D., Journal of Food Composition and Analysis (2009) 22:517-524.
48. Bermuidez-Soto M. J., Tomas-Barberan F. A. and M. T. Garcia-Conesa, Food Chem. (2007a) 102:865-874.
49. Bermúdez-Soto M. J., Larrosa M., García-Cantalejo J., Espin J. C., Tomas-Barberan F. A. and M. T. García-Conesa, Genes Nutr. (2007b) 2:111-113.
50. Bérubé K, Prytherch Z., Job C. and T. Hughes, Toxicology (2010) 278:311-8.
51. Chirinos, R., Rogez, H., Campos, D., Pedreschi, R., and Larondelle, Y., Separation and Purification Technology (2007) 55:217-225.
52. Djukanovic R., Roche W. R., Wilson J. W., Beasley C. R., Twentyman O. P., Howarth R. H. and S. T. Holgate, Am. Rev. Respir. Dis. (1990) 142:434-457.

53. Khetani, S. R. and S. N. Bhatia, Current Opinion Biotech. (2006) 17:524-531.
54. Mahe, S., Roos, N., Benamouzig, R., Sick, H., Baglieri, A., Huneau, J. F. and D. Tome, J. Nutr. (1994) 124:548-555.
55. Meng, Z., Li, R. and X. Zhang, Inhal. Toxicol. (2005a) 17:309-313.
56. Meng Z., Liu Y. and D. Wu, Inhal. Toxicol. (2005b) 17:303-307.
57. Nyberg, F., Gustavsson, P., Jarup, L., Bellander, T., Berglind, N., Jakobsson, R. and G., Epidemiology (2000) 11:487.
58. Pelletier, M., Lavastre, V. and D. Girard, Toxicol. Sci. (2002) 69:210-216.
59. Ratthe, C., Pelletier, M., Roberge, C. J. and D. Girard, Clin. Immunol. (2002) 105:169-175.
60. Shakya R, Navarre D A., J Agric Food Chem (2006) 54: 5253-5260.
61. Shapiro, R. Nutat. Res. (1977) 38:149-176.
62. Singleton, V. L. and Rossi, J. A., Jr., American Journal of Enology and Viticulture (1965) 16:144-158.
63. Tang R. B. and J. S. J. Chen, J. Asthma. (2000) 37:409-413.
64. Vilela, R. M., Lands, L. C., Chan, H. M., Azadi, B. and S. Kubow, Mol. Nutr. Food Res. (2006) 50:1013-1029.
65. Wang H. and J. A. Joseph, Free Radic. Biol. Med. (1999) 27:612-616.
66. Yang Y. F., Hsu J. Y., Fu L. S., Weng Y. S. and J. J. Chu, J. Asthma. (2009) 46:238-43.
67. Ogden, C. L., Yanovski, S. Z., Carroll, M. D., Flegal, K. M., The epidemiology of obesity. Gastroenterology 2007, 132, 2087-2102.
68. Liu, Q., Chen, L., Hu, L., Guo, Y., Shen, X., Small molecules from natural sources, targeting signaling pathways in diabetes. Biochim. Biophys. Acta 2010, 1799, 854-865.
69. Shehzad, A., Ha, T., Subhan, F., Lee, Y. S., New mechanisms and the anti-inflammatory role of curcumin in obesity and obesity-related metabolic diseases. Eur. J. Nutr. 2011, 50, 151-161.
70. Hwang, J. T., Kwon, D. Y., Yoon, S. H., AMP-activated protein kinase: a potential target for the diseases prevention by natural occurring polyphenols. N Biotechnol 2009, 26, 17-22.
71. Biesalski, H. K., Polyphenols and inflammation: basic interactions. Curr. Opin. Clin. Nutr. Metab. Care 2007, 10, 724-728.
72. Barone, E., Calabrese, V., Mancuso, C., Ferulic acid and its therapeutic potential as a hormetin for age-related diseases. Biogerontology 2009, 10, 97-108.
73. Hanhineva, K., Torronen, R., Bondia-Pons, I., Pekkinen, J., et al., Impact of dietary polyphenols on carbohydrate metabolism. Int. J. Mol. Sci. 2010, 11, 1365-1402.
74. Jacobs, D. R., Jr., Gross, M. D., Tapsell, L. C., Food synergy: an operational concept for understanding nutrition. Am. J. Clin. Nutr. 2009, 89, 1543S-1548S.
75. Andallu, B., Varadacharyulu, N., Antioxidant role of mulberry (*Morus indica* L. cv. *Anantha*) leaves in streptozotocin-diabetic rats. Clin. Chim. Acta 2003, 338, 3-10.
76. Kamalakkannan, N., Prince, P. S., Hypoglycaemic effect of water extracts of Aegle marmelos fruits in streptozotocin diabetic rats. J. Ethnopharmacol. 2003, 87, 207-210.
77. Bolkent, S., Yanardag, R., Tabakoglu-Oguz, A., Ozsoy-Sacan, O., Effects of chard (*Beta vulgaris* L. var. *Cicla*) extract on pancreatic B cells in streptozotocin-diabetic rats: a morphological and biochemical study. J. Ethnopharmacol. 2000, 73, 251-259.
78. Bravo, L., Polyphenols: chemistry, dietary sources, metabolism, and nutritional significance. Nutr. Rev. 1998, 56, 317-333.
79. Thompson, L. U., Yoon, J. H., Jenkins, D. J., Wolever, T. M., Jenkins, A. L., Relationship between polyphenol intake and blood glucose response of normal and diabetic individuals. Am. J. Clin. Nutr. 1984, 39, 745-751.
80. Camire, M. E., Kubow, S., Donnelly, D. J., Potatoes and human health. Crit. Rev. Food Sci. Nutr. 2009, 49, 823-840.
81. Singh, N., Kamath, V., Rajini, P. S., Protective effect of potato peel powder in ameliorating oxidative stress in streptozotocin diabetic rats. Plant Foods Hum. Nutr. 2005, 60, 49-54.
82. Yoon, S. S., Rhee, Y. H., Lee, H. J., Lee, E. O., et al., Uncoupled protein 3 and p38 signal pathways are involved in anti-obesity activity of *Solanum tuberosum* L. cv. Bora Valley. J. Ethnopharmacol. 2008, 118, 396-404.
83. Wang, C. Y., Liao, J. K., A mouse model of diet-induced obesity and insulin resistance. Methods Mol. Biol. 2012, 821, 421-433.
84. Friedman, M., Chemistry, Biochemistry, and Dietary Role of Potato Polyphenols. A Review. J. Agric. Food Chem. 1997, 45, 1523-1540.
85. Cho, A. S., Jeon, S. M., Kim, M. J., Yeo, J., et al., Chlorogenic acid exhibits anti-obesity property and improves lipid metabolism in high-fat diet-induced-obese mice. Food Chem. Toxicol. 2010, 48, 937-943.
86. Jin Son, M., C, W. R., Hyun Nam, S., Young Kang, M., Influence of oryzanol and ferulic Acid on the lipid metabolism and antioxidative status in high fat-fed mice. J. Clin. Biochem. Nutr. 2010, 46, 150-156.
87. Tunnicliffe, J. M., Eller, L. K., Reimer, R. A., Hittel, D. S., Shearer, J., Chlorogenic acid differentially affects postprandial glucose and glucose-dependent insulinotropic polypeptide response in rats. Appl. Physiol. Nutr. Metab. 2011, 36, 650-659.
88. Ohnishi, M., Matuo, T., Tsuno, T., Hosoda, A., et al., Antioxidant activity and hypoglycemic effect of ferulic acid in STZ-induced diabetic mice and KK-Ay mice. Biofactors 2004, 21, 315-319.
89. Shimoda, H., Seki, E., Aitani, M., Inhibitory effect of green coffee bean extract on fat accumulation and body weight gain in mice. BMC Complement Altern. Med. 2006, 6, 9.
90. Mubarak, A., Hodgson, J. M., Considine, M. J., Croft, K. D., Matthews, V. B., Supplementation of a high-fat diet with chlorogenic Acid is associated with insulin resistance and hepatic lipid accumulation in mice. J. Agric. Food Chem. 2013, 61, 4371-4378.
91. Sugiyama, M. G., Agellon, L. B., Sex differences in lipid metabolism and metabolic disease risk. Biochem. Cell Biol. 2012, 90, 124-141.
92. Andrikopoulos, S., Blair, A. R., Deluca, N., Fam, B. C., Proietto, J., Evaluating the glucose tolerance test in mice. Am. J. Physiol. Endocrinol. Metab. 2008, 295, E1323-1332.
93. Tabak, A. G., Herder, C., Rathmann, W., Brunner, E. J., Kivimaki, M., Prediabetes: a high-risk state for diabetes development. Lancet 2012, 379, 2279-2290.
94. Gomez, G., Han, S., Englander, E. W., Greeley, G. H., Jr., Influence of a long-term high-fat diet on ghrelin secretion and ghrelin-induced food intake in rats. Regul. Pept. 2012, 173, 60-63.
95. McCowen, K. C., Maykel, J. A., Bistrian, B. R., Ling, P. R., Circulating ghrelin concentrations are lowered by intravenous glucose or hyperinsulinemic euglycemic conditions in rodents. J. Endocrinol. 2002, 175, R7-11.
96. McLaughlin, T., Abbasi, F., Lamendola, C., Frayo, R. S., Cummings, D. E., Plasma ghrelin concentrations are decreased in insulin-resistant obese adults relative to equally obese insulin-sensitive controls. J. Clin. Endocrinol. Metab. 2004, 89, 1630-1635.
97. Frederich, R. C., Hamann, A., Anderson, S., Lollmann, B., et al., Leptin levels reflect body lipid content in mice: evidence for diet-induced resistance to leptin action. Nat. Med. 1995, 1, 1311-1314.
98. Considine, R. V., Sinha, M. K., Heiman, M. L., Kriauciunas, A., et al., Serum immunoreactive-leptin concentrations in normal-weight and obese humans. N. Engl. J. Med. 1996, 334, 292-295.
99. Miyawaki, K., Yamada, Y., Ban, N., Ihara, Y., et al., Inhibition of gastric inhibitory polypeptide signaling prevents obesity. Nat. Med. 2002, 8, 738-742.
100. Yang, Z. H., Miyahara, H., Takeo, J., Katayama, M., Diet high in fat and sucrose induces rapid onset of obesity-related metabolic syndrome partly through rapid response of genes involved in lipogenesis, insulin signalling and inflammation in mice. Diabetol. Metab. Syndr. 2012, 4, 32.
101. Seeram, N. P., Adams, L. S., Hardy, M. L., Heber, D., Total cranberry extract versus its phytochemical constituents: antiproliferative and synergistic effects against human tumor cell lines. J. Agric. Food Chem. 2004, 52, 2512-2517.
102. Crandall, J. P., Oram, V., Trandafirescu, G., Reid, M., et al., Pilot study of resveratrol in older adults with impaired glucose tolerance. J. Gerontol. A. Biol. Sci. Med. Sci. 2012, 67, 1307-1312.

What is claimed is:

1. A dietary supplement or additive for reducing body weight gain and/or controlling blood glucose levels comprising a composition enriched in ferulic acid, caffeic acid, chlorogenic acids, anthocyanins, ascorbic acid, and rutin, or an isomer or derivative thereof having antioxidant and/or anti-inflammatory activity, said composition comprising an extract or fraction of an Onaway potato cultivar and a Russet Burbank potato cultivar wherein the extract or fraction comprises said chlorogenic acids and said ferulic acid in a proportion ranging between 25:1 and 35:1 by weight.

2. The dietary supplement or additive of claim 1, wherein said composition further comprises an extract or fraction of at least one of a Bora Valley or Purple Valley potato cultivar, or a combination thereof.

3. The dietary supplement or additive of claim 1, prepared as an oral supplement, a functional food, or a food/feed additive.

4. The dietary supplement or additive of claim 1, wherein said extract or fraction is derived from the potato skin, pith, or cortex, or a combination thereof.

5. The dietary supplement or additive of claim 1, formulated as a pharmaceutical or nutraceutical composition and further comprising one or more acceptable carriers or excipients.

6. The dietary supplement or additive of claim 1, wherein the extract or fraction is obtained from a fresh source of at least one potato cultivar.

7. The dietary supplement or additive of claim 1, wherein the extract or fraction is obtained from the source of at least one potato cultivar within 2 months post-harvest.

8. The dietary supplement or additive of claim 1, wherein the extract or fraction is obtained from the source of the potato cultivar within 1 month post-harvest.

9. The dietary supplement or additive of claim 1, wherein the source of the potato cultivar has been treated to induce hormesis before or after harvesting, or during the storage interval of the source of at least one potato cultivar, and the treatment increases the level of one or more of ferulic acid, caffeic acid, chlorogenic acids, anthocyanins, ascorbic acid, rutin, or isomers or derivatives thereof having antioxidant and/or anti-inflammatory activity in the source of at least one potato cultivar.

10. The dietary supplement or additive of claim 9, wherein the treatment to induce hormesis is selected from the group consisting of: treatment with relatively high or low temperature air or water; treatment with an excess of one or more minerals; partial to severe starvation of one or more minerals; treatment with ionizing radiation; treatment with one or more oxidizing agents; wounding; and treatment with one or more phytochemicals.

11. A functional food comprising a food enriched with a dietary supplement or additive according to claim 1.

* * * * *